US012582527B1

(12) United States Patent
Miller et al.

(10) Patent No.: US 12,582,527 B1
(45) Date of Patent: *Mar. 24, 2026

(54) SHEET BASED TRIPLY PERIODIC MINIMAL SURFACE IMPLANTS FOR PROMOTING OSSEOINTEGRATION AND METHODS FOR PRODUCING SAME

(71) Applicants:restor3d, Inc., Durham, NC (US); Duke University, Durham, NC (US)

(72) Inventors: Andrew Todd Miller, Durham, NC (US); Matthew Rexrode, Durham, NC (US); Cambre Kelly, Durham, NC (US); Ken Gall, Durham, NC (US)

(73) Assignees: RESTOR3D, INC., Durham, NC (US); DUKE UNIVERSITY, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/938,248

(22) Filed: Oct. 5, 2022

Related U.S. Application Data

(63) Continuation of application No. 17/314,357, filed on May 7, 2021, now Pat. No. 11,484,413, which is a
(Continued)

(51) Int. Cl.
*A61F 2/44* (2006.01)
*A61F 2/30* (2006.01)

(52) U.S. Cl.
CPC .......... *A61F 2/3094* (2013.01); *A61F 2/4455* (2013.01); *A61F 2002/30736* (2013.01);
(Continued)

(58) Field of Classification Search
CPC .... A61F 2002/3092; A61F 2002/30942; A61F 2002/30943; A61F 2002/30952;
(Continued)

(56) References Cited

U.S. PATENT DOCUMENTS

| | | | |
|---|---|---|---|
| 1,428,247 A | 9/1922 | Morris | |
| D220,184 S | 3/1971 | Boone | |

(Continued)

FOREIGN PATENT DOCUMENTS

| | | |
|---|---|---|
| CN | 109567913 A | 4/2019 |
| CN | 109622958 A | 4/2019 |

(Continued)

OTHER PUBLICATIONS

Yan et al., Microstructure and mechanical properties of aluminum alloy cellular lattice structures manufactured by direct metal laser sintering, Jan. 31, 2015, Materials Science and Engineering A 628 (2015) 238-246 (Year: 2015).*

(Continued)

*Primary Examiner* — Lynnsy M Summitt
(74) *Attorney, Agent, or Firm* — Husch Blackwell LLP; Bryan D. Stewart

(57) ABSTRACT

Provided herein are implants and methods for producing implants. In at least one embodiment, the implants include sheet-based, triply periodic, minimal surface (TPMS) portions. According to one embodiment, the TPMS portions include a gyroid architecture that provides for improved osseointegration and mechanical performance over previous implants due to novel ratios of porosity to compressive strength, among other features. In one or more embodiments, the gyroid architecture is organized into unit cells that demonstrate anisotropic mechanical performance along an insertion direction. In various embodiments, the present methods include novel selective laser melting (SLM) techniques for forming the TPMS portions of implants in a manner that reduces defect formation, thereby improving compressive performance and other implant properties.

23 Claims, 38 Drawing Sheets

Related U.S. Application Data continuation of application No. 16/991,638, filed on Aug. 12, 2020, now Pat. No. 11,026,798, which is a continuation of application No. 16/737,341, filed on Jan. 8, 2020, now Pat. No. 10,772,732.

(52) U.S. Cl.
CPC .............. *A61F 2002/30784* (2013.01); *A61F 2002/30985* (2013.01); *A61F 2310/00023* (2013.01)

(58) Field of Classification Search
CPC .. A61F 2002/30985; A61F 2002/30962; A61F 2002/30978
See application file for complete search history.

(56) References Cited

U.S. PATENT DOCUMENTS

| | | | |
|---|---|---|---|
| 3,872,519 A | | 3/1975 | Giannestras |
| D265,288 S | | 7/1982 | McLean |
| 4,440,835 A | | 4/1984 | Mgnaud |
| 4,588,574 A | | 5/1986 | Felder et al. |
| 4,829,152 A | * | 5/1989 | Rostoker ................ B23K 11/20 |
| | | | 219/117.1 |
| D309,185 S | | 7/1990 | Lockawich |
| D336,517 S | | 6/1993 | Mckeown |
| 5,238,613 A | | 8/1993 | Anderson |
| 5,248,456 A | | 9/1993 | Evans, Jr. et al. |
| D358,211 S | | 5/1995 | Cohen |
| D358,647 S | | 5/1995 | Cohen et al. |
| 5,497,785 A | | 3/1996 | Viera |
| 5,497,786 A | | 3/1996 | Urick |
| 5,591,191 A | | 1/1997 | Kieturakis |
| 5,766,259 A | | 6/1998 | Sammarco |
| 5,947,965 A | | 9/1999 | Bryan |
| 6,183,519 B1 | | 2/2001 | Bonnin |
| 6,419,491 B1 | * | 7/2002 | Ricci ................... A61F 2/30771 |
| | | | 433/173 |
| 6,461,358 B1 | | 10/2002 | Faccioli |
| D490,901 S | | 6/2004 | Schulter et al. |
| D493,890 S | | 8/2004 | Schulter et al. |
| 6,989,003 B2 | | 1/2006 | Wing et al. |
| 7,001,672 B2 | | 2/2006 | Justin et al. |
| D521,642 S | | 5/2006 | Dorahy |
| 7,048,741 B2 | | 5/2006 | Swanson |
| 7,125,423 B2 | | 10/2006 | Hazebrouck |
| D539,426 S | | 3/2007 | Callaghan |
| 7,468,075 B2 | | 12/2008 | Lang et al. |
| D593,202 S | | 5/2009 | Petersen |
| 7,534,246 B2 | | 5/2009 | Reiley |
| 7,534,263 B2 | | 5/2009 | Burdulis, Jr. et al. |
| 7,534,270 B2 | | 5/2009 | Ball |
| D595,853 S | | 7/2009 | Hanson |
| D598,094 S | | 8/2009 | Alber |
| D604,153 S | | 11/2009 | Wantz |
| 7,618,451 B2 | | 11/2009 | Berez et al. |
| 7,632,575 B2 | | 12/2009 | Justin et al. |
| 7,634,119 B2 | | 12/2009 | Tsougarakis et al. |
| 7,666,522 B2 | | 2/2010 | Justin et al. |
| D611,147 S | | 3/2010 | Hanson et al. |
| 7,717,956 B2 | | 5/2010 | Lang |
| D618,800 S | | 6/2010 | Mayon et al. |
| D620,111 S | | 7/2010 | Courtney et al. |
| D623,749 S | | 9/2010 | Horton |
| 7,796,791 B2 | | 9/2010 | Tsougarakis et al. |
| 7,799,077 B2 | | 9/2010 | Lang et al. |
| 7,819,614 B2 | | 10/2010 | Versino et al. |
| D628,344 S | | 11/2010 | Raviv |
| 7,981,158 B2 | | 7/2011 | Fitz et al. |
| 8,062,302 B2 | | 11/2011 | Lang et al. |
| 8,066,708 B2 | | 11/2011 | Lang et al. |
| 8,077,950 B2 | | 12/2011 | Tsougarakis et al. |
| 8,083,745 B2 | | 12/2011 | Lang et al. |
| 8,094,900 B2 | | 1/2012 | Steines et al. |
| 8,105,330 B2 | | 1/2012 | Fitz et al. |
| D653,756 S | | 2/2012 | Courtney et al. |
| 8,122,582 B2 | | 2/2012 | Burdulis, Jr. et al. |
| 8,128,580 B2 | | 3/2012 | Fujimagari et al. |
| 8,142,886 B2 | | 3/2012 | Noble et al. |
| D660,432 S | | 5/2012 | Braido |
| D660,966 S | | 5/2012 | Sheild |
| 8,234,097 B2 | | 7/2012 | Steines et al. |
| D666,298 S | | 8/2012 | Sibhatu et al. |
| 8,262,589 B2 | | 9/2012 | Lupton |
| 8,337,501 B2 | | 12/2012 | Fitz et al. |
| 8,337,507 B2 | | 12/2012 | Lang et al. |
| D675,320 S | | 1/2013 | Oi |
| 8,343,218 B2 | | 1/2013 | Lang et al. |
| 8,366,771 B2 | | 2/2013 | Burdulis, Jr. et al. |
| 8,377,129 B2 | | 2/2013 | Fitz et al. |
| 8,382,755 B2 | | 2/2013 | Austin |
| D681,204 S | | 4/2013 | Farris et al. |
| 8,430,930 B2 | | 4/2013 | Hunt |
| 8,439,926 B2 | | 5/2013 | Bojarski et al. |
| D683,856 S | | 6/2013 | Chin et al. |
| 8,457,930 B2 | | 6/2013 | Schroeder |
| 8,460,304 B2 | | 6/2013 | Fitz et al. |
| 8,480,754 B2 | | 7/2013 | Bojarski et al. |
| 8,485,820 B1 | | 7/2013 | Ali |
| 8,500,740 B2 | | 8/2013 | Bojarski et al. |
| 8,529,568 B2 | | 9/2013 | Bouadi |
| 8,529,630 B2 | | 9/2013 | Bojarski et al. |
| D692,136 S | | 10/2013 | Tyber |
| 8,545,569 B2 | | 10/2013 | Fitz et al. |
| 8,551,099 B2 | | 10/2013 | Lang et al. |
| 8,551,102 B2 | | 10/2013 | Fitz et al. |
| 8,551,103 B2 | | 10/2013 | Fitz et al. |
| 8,551,169 B2 | | 10/2013 | Fitz et al. |
| 8,551,173 B2 | | 10/2013 | Lechmann et al. |
| 8,556,906 B2 | | 10/2013 | Fitz et al. |
| 8,556,907 B2 | | 10/2013 | Fitz et al. |
| 8,556,971 B2 | | 10/2013 | Lang |
| 8,556,983 B2 | | 10/2013 | Bojarski et al. |
| 8,561,278 B2 | | 10/2013 | Fitz et al. |
| 8,562,611 B2 | | 10/2013 | Fitz et al. |
| 8,562,618 B2 | | 10/2013 | Fitz et al. |
| 8,568,479 B2 | | 10/2013 | Fitz et al. |
| 8,568,480 B2 | | 10/2013 | Fitz et al. |
| 8,585,708 B2 | | 11/2013 | Fitz et al. |
| 8,617,172 B2 | | 12/2013 | Fitz et al. |
| 8,617,242 B2 | | 12/2013 | Philipp et al. |
| 8,623,026 B2 | | 1/2014 | Wong et al. |
| 8,634,617 B2 | | 1/2014 | Tsougarakis et al. |
| 8,638,998 B2 | | 1/2014 | Steines et al. |
| 8,641,716 B2 | | 2/2014 | Fitz et al. |
| 8,657,827 B2 | | 2/2014 | Fitz et al. |
| D700,700 S | | 3/2014 | Efinger |
| 8,682,052 B2 | | 3/2014 | Fitz et al. |
| 8,690,945 B2 | | 4/2014 | Fitz et al. |
| 8,709,089 B2 | | 4/2014 | Lang et al. |
| 8,715,362 B2 | | 5/2014 | Reiley |
| 8,735,773 B2 | | 5/2014 | Lang |
| D708,747 S | | 7/2014 | Curran et al. |
| 8,768,028 B2 | | 7/2014 | Lang et al. |
| 8,771,365 B2 | | 7/2014 | Bojarski et al. |
| 8,775,133 B2 | | 7/2014 | Schroeder |
| 8,828,311 B2 | | 9/2014 | Medina et al. |
| 8,843,229 B2 | | 9/2014 | Vanasse et al. |
| 8,882,847 B2 | | 11/2014 | Burdulis, Jr. et al. |
| 8,888,485 B2 | | 11/2014 | Ali |
| 8,906,107 B2 | | 12/2014 | Bojarski et al. |
| 8,926,706 B2 | | 1/2015 | Bojarski et al. |
| 8,932,363 B2 | | 1/2015 | Tsougarakis et al. |
| D722,693 S | | 2/2015 | Kaufmann et al. |
| 8,945,230 B2 | | 2/2015 | Lang et al. |
| 8,951,259 B2 | | 2/2015 | Fitz et al. |
| 8,951,260 B2 | | 2/2015 | Lang et al. |
| 8,965,088 B2 | | 2/2015 | Tsougarakis et al. |
| D724,213 S | | 3/2015 | Tyber |
| 8,974,539 B2 | | 3/2015 | Bojarski et al. |
| 8,998,915 B2 | | 4/2015 | Fitz et al. |
| 9,020,788 B2 | | 4/2015 | Lang et al. |
| 9,023,050 B2 | | 5/2015 | Lang et al. |

(56)  References Cited

U.S. PATENT DOCUMENTS

| | | | |
|---|---|---|---|
| 9,034,237 B2 | 5/2015 | Sperry et al. |
| 9,055,953 B2 | 6/2015 | Lang et al. |
| 9,066,728 B2 | 6/2015 | Burdulis, Jr. et al. |
| D734,460 S | 7/2015 | Froidevaux |
| 9,072,531 B2 | 7/2015 | Fitz et al. |
| 9,084,617 B2 | 7/2015 | Lang et al. |
| D735,860 S | 8/2015 | Palinchik |
| D736,384 S | 8/2015 | Palinchik |
| 9,095,353 B2 | 8/2015 | Burdulis, Jr. et al. |
| 9,095,439 B2 | 8/2015 | Lian |
| 9,107,679 B2 | 8/2015 | Lang et al. |
| 9,107,680 B2 | 8/2015 | Fitz et al. |
| 9,113,921 B2 | 8/2015 | Lang et al. |
| 9,125,672 B2 | 9/2015 | Fitz et al. |
| 9,125,673 B2 | 9/2015 | Fitz et al. |
| 9,144,500 B2 | 9/2015 | Harding |
| 9,180,015 B2 | 11/2015 | Fitz et al. |
| 9,180,029 B2 | 11/2015 | Hollister et al. |
| 9,186,161 B2 | 11/2015 | Lang et al. |
| 9,186,254 B2 | 11/2015 | Fitz et al. |
| 9,186,257 B2 | 11/2015 | Geisler et al. |
| D745,159 S | 12/2015 | Lin |
| 9,216,025 B2 | 12/2015 | Fitz et al. |
| 9,220,516 B2 | 12/2015 | Lang et al. |
| 9,220,517 B2 | 12/2015 | Lang et al. |
| D747,485 S | 1/2016 | Oi |
| 9,241,724 B2 | 1/2016 | Lang et al. |
| 9,241,725 B2 | 1/2016 | Lang et al. |
| 9,271,845 B2 | 3/2016 | Hunt et al. |
| 9,295,481 B2 | 3/2016 | Fitz et al. |
| 9,295,482 B2 | 3/2016 | Fitz et al. |
| 9,295,554 B2 | 3/2016 | Gillard et al. |
| 9,295,562 B2 | 3/2016 | Lechmann et al. |
| 9,308,005 B2 | 4/2016 | Fitz et al. |
| 9,308,053 B2 | 4/2016 | Bojarski et al. |
| 9,308,060 B2 | 4/2016 | Ali |
| 9,308,091 B2 | 4/2016 | Lang |
| 9,314,256 B2 | 4/2016 | Fitz et al. |
| 9,320,620 B2 | 4/2016 | Bojarski et al. |
| 9,326,780 B2 | 5/2016 | Wong et al. |
| 9,333,058 B1 | 5/2016 | Krastev |
| 9,339,279 B2 | 5/2016 | Dubois et al. |
| 9,358,018 B2 | 6/2016 | Fitz et al. |
| 9,364,896 B2 | 6/2016 | Christensen et al. |
| 9,370,426 B2 * | 6/2016 | Gabbrielli ............... B22F 7/004 |
| 9,375,222 B2 | 6/2016 | Fitz et al. |
| 9,381,025 B2 | 7/2016 | Fitz et al. |
| 9,387,079 B2 | 7/2016 | Bojarski et al. |
| 9,402,726 B2 | 8/2016 | Linderman et al. |
| 9,408,615 B2 | 8/2016 | Fitz et al. |
| 9,408,686 B1 | 8/2016 | Miller et al. |
| 9,415,137 B2 | 8/2016 | Meridew |
| 9,421,108 B2 | 8/2016 | Hunt |
| D767,137 S | 9/2016 | Lin |
| 9,433,510 B2 | 9/2016 | Lechmann et al. |
| 9,433,707 B2 | 9/2016 | Swords et al. |
| 9,439,767 B2 | 9/2016 | Bojarski et al. |
| 9,486,226 B2 | 11/2016 | Chao |
| 9,495,483 B2 | 11/2016 | Steines et al. |
| 9,517,134 B2 | 12/2016 | Lang |
| 9,545,317 B2 | 1/2017 | Hunt |
| 9,549,823 B2 | 1/2017 | Hunt et al. |
| 9,561,115 B2 | 2/2017 | Elahinia et al. |
| 9,572,669 B2 | 2/2017 | Hunt et al. |
| 9,579,110 B2 | 2/2017 | Bojarski et al. |
| 9,597,130 B2 | 3/2017 | Pappalardo et al. |
| 9,597,197 B2 | 3/2017 | Lechmann et al. |
| 9,603,711 B2 | 3/2017 | Bojarski et al. |
| 9,610,168 B2 | 4/2017 | Terrill |
| 9,636,226 B2 | 5/2017 | Hunt |
| 9,636,229 B2 | 5/2017 | Lang et al. |
| 9,649,178 B2 | 5/2017 | Ali |
| 9,662,157 B2 | 5/2017 | Schneider et al. |
| 9,662,226 B2 | 5/2017 | Wickham |
| 9,668,863 B2 | 6/2017 | Sharp et al. |
| 9,675,465 B2 | 6/2017 | Padovani et al. |
| 9,675,471 B2 | 6/2017 | Bojarski et al. |
| 9,681,956 B2 | 6/2017 | Al Hares et al. |
| 9,687,945 B2 | 6/2017 | Steines et al. |
| 9,688,026 B2 | 6/2017 | Ho et al. |
| 9,694,541 B2 | 7/2017 | Pruett et al. |
| 9,700,420 B2 | 7/2017 | Fitz et al. |
| 9,700,424 B2 | 7/2017 | Sanders et al. |
| 9,700,971 B2 | 7/2017 | Lang |
| 9,715,563 B1 | 7/2017 | Schroeder |
| 9,737,367 B2 | 8/2017 | Steines et al. |
| 9,750,613 B2 | 9/2017 | Petteys |
| 9,757,235 B2 | 9/2017 | Hunt et al. |
| 9,757,245 B2 | 9/2017 | O'Neil et al. |
| 9,775,680 B2 | 10/2017 | Bojarski et al. |
| 9,782,270 B2 | 10/2017 | Wickham |
| 9,788,972 B2 | 10/2017 | Flickinger et al. |
| 9,848,929 B2 | 12/2017 | Dacosta |
| 9,849,019 B2 | 12/2017 | Miller et al. |
| 9,872,773 B2 | 1/2018 | Lang et al. |
| 9,877,790 B2 | 1/2018 | Bojarski et al. |
| D809,661 S | 2/2018 | Mueller et al. |
| D813,394 S | 3/2018 | Dacosta et al. |
| D814,037 S | 3/2018 | Dacosta et al. |
| 9,907,670 B2 | 3/2018 | Deridder et al. |
| 9,910,935 B2 | 3/2018 | Golway et al. |
| 9,913,723 B2 | 3/2018 | Fitz et al. |
| 9,918,849 B2 | 3/2018 | Morris et al. |
| 9,925,054 B2 | 3/2018 | Siegler |
| D814,634 S | 4/2018 | Dacosta et al. |
| 9,943,370 B2 | 4/2018 | Asseln et al. |
| 9,943,627 B2 | 4/2018 | Zhou et al. |
| 9,949,839 B2 | 4/2018 | Sander |
| 9,956,047 B2 | 5/2018 | Bojarski et al. |
| 9,956,048 B2 | 5/2018 | Bojarski et al. |
| 9,962,209 B2 | 5/2018 | Dacosta et al. |
| 10,016,811 B2 | 7/2018 | Neal |
| D829,909 S | 10/2018 | Horton |
| D832,441 S | 10/2018 | Dacosta et al. |
| 10,085,839 B2 | 10/2018 | Wong et al. |
| D835,276 S | 12/2018 | Humphrey |
| D835,277 S | 12/2018 | Gottlieb |
| D835,278 S | 12/2018 | Gottlieb |
| D835,788 S | 12/2018 | Jones et al. |
| D835,977 S | 12/2018 | Pastorino et al. |
| 10,183,442 B1 | 1/2019 | Miller |
| D841,168 S | 2/2019 | Dacosta et al. |
| 10,245,152 B2 | 4/2019 | Kloss |
| 10,265,189 B2 | 4/2019 | Melkent et al. |
| D849,944 S | 5/2019 | Dacosta |
| 10,278,823 B1 * | 5/2019 | Xue ...................... A61F 2/3662 |
| D850,620 S | 6/2019 | Tyber |
| D855,184 S | 7/2019 | Predick |
| 10,357,377 B2 * | 7/2019 | Nyahay .................. A61F 2/447 |
| D857,201 S | 8/2019 | Predick et al. |
| D858,769 S | 9/2019 | Barela et al. |
| 10,449,051 B2 * | 10/2019 | Hamzey .................. A61F 2/447 |
| D870,288 S | 12/2019 | Dang et al. |
| 10,492,686 B2 | 12/2019 | Hunter |
| D873,031 S | 1/2020 | Martensson |
| D875,939 S | 2/2020 | Dacosta et al. |
| D877,907 S | 3/2020 | Linder et al. |
| D878,589 S | 3/2020 | Linder |
| D878,590 S | 3/2020 | Inder et al. |
| D879,295 S | 3/2020 | Abbasi |
| D879,961 S | 3/2020 | Inder et al. |
| 10,575,965 B2 | 3/2020 | Kim et al. |
| D881,665 S | 4/2020 | Zemel et al. |
| 10,624,746 B2 | 4/2020 | Jones et al. |
| 10,667,924 B2 * | 6/2020 | Nyahay ................. A61F 2/4455 |
| 10,675,158 B2 | 6/2020 | Unger et al. |
| 10,744,001 B2 * | 8/2020 | Sack ...................... A61F 2/4455 |
| 10,772,732 B1 | 9/2020 | Miller et al. |
| D898,197 S | 10/2020 | Cain |
| D899,900 S | 10/2020 | Blanco |
| 10,898,206 B2 | 1/2021 | Dacosta et al. |
| 10,940,015 B2 * | 3/2021 | Sack ...................... A61F 2/4455 |
| 10,940,019 B2 | 3/2021 | Vishnubhotla et al. |
| D917,697 S | 4/2021 | Reed et al. |

(56) References Cited

U.S. PATENT DOCUMENTS

| | | | |
|---|---|---|---|
| D920,515 S | 5/2021 | Miller | |
| D920,516 S | 5/2021 | Miller | |
| D920,517 S | 5/2021 | Miller | |
| 11,026,798 B1 | 6/2021 | Miller | |
| 11,033,394 B2 * | 6/2021 | Hamzey | A61F 2/4081 |
| 11,135,771 B1 * | 10/2021 | Reith | B33Y 40/00 |
| 11,147,682 B2 | 10/2021 | Trudeau et al. | |
| D938,033 S | 12/2021 | Dang | |
| D942,011 S | 1/2022 | Cain | |
| D942,623 S | 2/2022 | Cain | |
| D942,624 S | 2/2022 | Cain | |
| D944,400 S | 2/2022 | Cain | |
| 11,273,048 B2 | 3/2022 | Cain et al. | |
| 11,273,051 B2 | 3/2022 | Neary | |
| 11,324,525 B1 | 5/2022 | Garvey | |
| 11,353,277 B2 * | 6/2022 | Muceus | B22F 5/106 |
| 11,439,726 B2 * | 9/2022 | Spence | A61F 2/30771 |
| D967,960 S | 10/2022 | Wang et al. | |
| 11,471,203 B2 * | 10/2022 | Sutika | A61B 17/8635 |
| D968,614 S | 11/2022 | Cain | |
| 11,534,307 B2 | 12/2022 | Struck et al. | |
| D986,728 S | 5/2023 | Jou et al. | |
| 11,648,125 B2 | 5/2023 | Ng | |
| 11,666,367 B2 | 6/2023 | Goradia | |
| 11,666,452 B2 | 6/2023 | Melkent et al. | |
| D992,116 S | 7/2023 | Miller et al. | |
| 11,744,716 B2 | 9/2023 | Jebsen et al. | |
| 11,850,144 B1 | 12/2023 | Garrigues | |
| D1,013,875 S | 2/2024 | Miller et al. | |
| D1,013,876 S | 2/2024 | Miller et al. | |
| 11,950,822 B2 | 4/2024 | Champagne et al. | |
| 11,960,266 B1 | 4/2024 | Kelly et al. | |
| D1,030,046 S | 6/2024 | Boey et al. | |
| 2001/0031966 A1 | 10/2001 | Tormala et al. | |
| 2003/0045834 A1 | 3/2003 | Wing et al. | |
| 2004/0049284 A1 | 3/2004 | German et al. | |
| 2004/0049285 A1 | 3/2004 | Haas | |
| 2004/0148032 A1 | 7/2004 | Rutter et al. | |
| 2004/0230313 A1 | 11/2004 | Saunders | |
| 2005/0010302 A1 | 1/2005 | Dietz et al. | |
| 2006/0074492 A1 | 4/2006 | Frey | |
| 2006/0178748 A1 | 8/2006 | Dinger, III et al. | |
| 2006/0229730 A1 | 10/2006 | Railey et al. | |
| 2006/0249875 A1 | 11/2006 | Robb et al. | |
| 2007/0055251 A1 | 3/2007 | Huebner et al. | |
| 2007/0100346 A1 | 5/2007 | Wyss | |
| 2007/0118243 A1 | 5/2007 | Schroeder et al. | |
| 2007/0244563 A1 | 10/2007 | Roche et al. | |
| 2008/0091271 A1 | 4/2008 | Bonitati et al. | |
| 2008/0206297 A1 | 8/2008 | Roeder et al. | |
| 2009/0093668 A1 | 4/2009 | Marten et al. | |
| 2009/0182430 A1 | 7/2009 | Tyber et al. | |
| 2010/0055644 A1 | 3/2010 | Arni | |
| 2010/0137990 A1 | 6/2010 | Apatsidis et al. | |
| 2010/0168798 A1 | 7/2010 | Clineff et al. | |
| 2010/0286791 A1 | 11/2010 | Goldsmith | |
| 2011/0054611 A1 | 3/2011 | Wu et al. | |
| 2011/0071802 A1 | 3/2011 | Bojarski et al. | |
| 2011/0144752 A1 | 6/2011 | Defelice et al. | |
| 2011/0190898 A1 | 8/2011 | Lenz | |
| 2011/0190899 A1 | 8/2011 | Pierce et al. | |
| 2011/0224796 A1 | 9/2011 | Weiland et al. | |
| 2011/0230974 A1 | 9/2011 | Musani | |
| 2012/0064288 A1 | 3/2012 | Nakano et al. | |
| 2012/0215310 A1 | 8/2012 | Sharp et al. | |
| 2012/0239152 A1 | 9/2012 | Ullrich, Jr. et al. | |
| 2012/0257507 A1 | 10/2012 | Sato et al. | |
| 2012/0259419 A1 | 10/2012 | Brown et al. | |
| 2013/0046313 A1 | 2/2013 | Lian | |
| 2013/0068968 A1 | 3/2013 | Daniel | |
| 2013/0123935 A1 | 5/2013 | Hunt et al. | |
| 2013/0158651 A1 | 6/2013 | Hollister et al. | |
| 2013/0184820 A1 | 7/2013 | Schwartz et al. | |
| 2013/0197657 A1 | 8/2013 | Anca et al. | |
| 2013/0218282 A1 | 8/2013 | Hunt | |
| 2013/0274890 A1 | 10/2013 | McKay | |
| 2013/0296874 A1 | 11/2013 | Chao | |
| 2014/0100779 A1 | 4/2014 | Tuke | |
| 2014/0107785 A1 | 4/2014 | Geisler et al. | |
| 2014/0107786 A1 | 4/2014 | Geisler et al. | |
| 2014/0236299 A1 | 8/2014 | Roeder et al. | |
| 2014/0277443 A1 | 9/2014 | Fleury et al. | |
| 2014/0277452 A1 | 9/2014 | Skaer | |
| 2014/0277538 A1 | 9/2014 | Sander | |
| 2014/0288650 A1 | 9/2014 | Hunt | |
| 2014/0336680 A1 | 11/2014 | Medina et al. | |
| 2014/0350688 A1 | 11/2014 | Michel | |
| 2014/0371863 A1 | 12/2014 | Vanasse et al. | |
| 2015/0025666 A1 | 1/2015 | Olivieri et al. | |
| 2015/0045839 A1 | 2/2015 | Dacosta et al. | |
| 2015/0105858 A1 | 4/2015 | Papay et al. | |
| 2015/0282945 A1 | 10/2015 | Hunt | |
| 2015/0282946 A1 | 10/2015 | Hunt | |
| 2015/0320461 A1 | 11/2015 | Ehmke | |
| 2015/0335434 A1 | 11/2015 | Patterson et al. | |
| 2015/0343709 A1 | 12/2015 | Gerstle et al. | |
| 2015/0351915 A1 | 12/2015 | Defelice et al. | |
| 2015/0374411 A1 | 12/2015 | Ehmke et al. | |
| 2016/0008139 A1 | 1/2016 | Siegler | |
| 2016/0051371 A1 | 2/2016 | Defelice et al. | |
| 2016/0089138 A1 | 3/2016 | Early et al. | |
| 2016/0151833 A1 | 6/2016 | Tsao | |
| 2016/0166392 A1 | 6/2016 | Vanasse et al. | |
| 2016/0193055 A1 | 7/2016 | Ries | |
| 2016/0199193 A1 | 7/2016 | Willis et al. | |
| 2016/0213485 A1 | 7/2016 | Schaufler et al. | |
| 2016/0213486 A1 | 7/2016 | Nunley et al. | |
| 2016/0213487 A1 | 7/2016 | Wilson et al. | |
| 2016/0213488 A1 | 7/2016 | Moore et al. | |
| 2016/0220288 A1 | 8/2016 | Dubois et al. | |
| 2016/0228255 A1 | 8/2016 | Samuelson et al. | |
| 2016/0256279 A1 | 9/2016 | Sanders et al. | |
| 2016/0256610 A1 | 9/2016 | Zhou et al. | |
| 2016/0270931 A1 | 9/2016 | Trieu | |
| 2016/0287388 A1 | 10/2016 | Hunt et al. | |
| 2016/0303793 A1 | 10/2016 | Ermoshkin et al. | |
| 2016/0310189 A1 | 10/2016 | Dacosta et al. | |
| 2016/0333152 A1 | 11/2016 | Cook et al. | |
| 2016/0374829 A1 | 12/2016 | Vogt et al. | |
| 2017/0014169 A1 * | 1/2017 | Dean | A61B 17/8071 |
| 2017/0018919 A1 | 1/2017 | Chen et al. | |
| 2017/0020685 A1 | 1/2017 | Geisler et al. | |
| 2017/0036403 A1 | 2/2017 | Ruff et al. | |
| 2017/0042697 A1 | 2/2017 | Mcshane, III et al. | |
| 2017/0056178 A1 | 3/2017 | Sharp et al. | |
| 2017/0056179 A1 | 3/2017 | Lorio | |
| 2017/0066873 A1 | 3/2017 | Gardet | |
| 2017/0105844 A1 | 4/2017 | Kuyler et al. | |
| 2017/0156880 A1 | 6/2017 | Verson et al. | |
| 2017/0165085 A1 | 6/2017 | Lechmann et al. | |
| 2017/0165790 A1 | 6/2017 | McCarthy et al. | |
| 2017/0172758 A1 | 6/2017 | Field et al. | |
| 2017/0182222 A1 | 6/2017 | Paddock et al. | |
| 2017/0209274 A1 | 7/2017 | Beerens et al. | |
| 2017/0216035 A1 | 8/2017 | Hunt | |
| 2017/0216036 A1 | 8/2017 | Cordaro | |
| 2017/0239054 A1 | 8/2017 | Engstrand et al. | |
| 2017/0239064 A1 | 8/2017 | Cordaro | |
| 2017/0245998 A1 | 8/2017 | Padovani et al. | |
| 2017/0252165 A1 | 9/2017 | Sharp et al. | |
| 2017/0258606 A1 | 9/2017 | Afzal | |
| 2017/0282455 A1 | 10/2017 | Defelice et al. | |
| 2017/0296244 A1 | 10/2017 | Schneider et al. | |
| 2017/0319344 A1 | 11/2017 | Hunt | |
| 2017/0323037 A1 | 11/2017 | Schroeder | |
| 2017/0333205 A1 | 11/2017 | Joly et al. | |
| 2017/0354510 A1 | 12/2017 | O'Neil et al. | |
| 2017/0354513 A1 | 12/2017 | Maglaras et al. | |
| 2017/0355815 A1 | 12/2017 | Becker et al. | |
| 2017/0360488 A1 | 12/2017 | Kowalczyk et al. | |
| 2017/0360563 A1 | 12/2017 | Hunt et al. | |
| 2017/0360578 A1 | 12/2017 | Shin et al. | |
| 2017/0367843 A1 | 12/2017 | Eisen et al. | |
| 2017/0367844 A1 | 12/2017 | Eisen et al. | |

(56) References Cited

U.S. PATENT DOCUMENTS

| | | | |
|---|---|---|---|
| 2017/0367845 A1 | 12/2017 | Eisen et al. | |
| 2018/0008419 A1 | 1/2018 | Tyber et al. | |
| 2018/0012517 A1 | 1/2018 | Ropelato et al. | |
| 2018/0022017 A1 | 1/2018 | Fukumoto et al. | |
| 2018/0064540 A1 | 3/2018 | Hunt | |
| 2018/0085230 A1 | 3/2018 | Hunt | |
| 2018/0098858 A1 | 4/2018 | Valderraband | |
| 2018/0104063 A1 | 4/2018 | Asaad | |
| 2018/0110593 A1 | 4/2018 | Khalil | |
| 2018/0110626 A1 | 4/2018 | McShane, III et al. | |
| 2018/0110627 A1 | 4/2018 | Sack | |
| 2018/0117219 A1 | 5/2018 | Yang et al. | |
| 2018/0147319 A1 | 5/2018 | Colucci-Mizenko et al. | |
| 2018/0185547 A1 | 7/2018 | Grayson et al. | |
| 2018/0196920 A1 | 7/2018 | Liang et al. | |
| 2018/0243094 A1 | 8/2018 | Jones et al. | |
| 2018/0256336 A1 | 9/2018 | Mueller et al. | |
| 2018/0280140 A1 | 10/2018 | Jones | |
| 2018/0289380 A1 | 10/2018 | Mauldin | |
| 2018/0289515 A1 | 10/2018 | Nemes et al. | |
| 2019/0076258 A1 | 3/2019 | Black et al. | |
| 2019/0091027 A1 | 3/2019 | Asaad et al. | |
| 2019/0117410 A1 | 4/2019 | Parry et al. | |
| 2019/0167433 A1* | 6/2019 | Allen | A61F 2/30721 |
| 2019/0262101 A1* | 8/2019 | Shanjani | A61C 7/08 |
| 2019/0269527 A1 | 9/2019 | Moore | |
| 2019/0302736 A1 | 10/2019 | Chanin | |
| 2019/0343652 A1 | 11/2019 | Petersheim et al. | |
| 2020/0000595 A1* | 1/2020 | Jones | A61B 90/96 |
| 2020/0030102 A1 | 1/2020 | Mullens et al. | |
| 2020/0030108 A1 | 1/2020 | Orphanos et al. | |
| 2020/0046512 A1 | 2/2020 | Newman et al. | |
| 2020/0085452 A1 | 3/2020 | Siegler | |
| 2020/0085585 A1 | 3/2020 | Siegler | |
| 2020/0155321 A1* | 5/2020 | Dikovsky | B29C 64/112 |
| 2020/0171752 A1* | 6/2020 | Rogren | G03G 15/50 |
| 2020/0171753 A1* | 6/2020 | Satko | B29C 64/386 |
| 2020/0197565 A1 | 6/2020 | Suh et al. | |
| 2020/0222191 A1 | 7/2020 | Arnone | |
| 2020/0253649 A1 | 8/2020 | Langdale et al. | |
| 2020/0281737 A1 | 9/2020 | Stebbins et al. | |
| 2020/0289714 A1 | 9/2020 | Snell et al. | |
| 2020/0367910 A1 | 11/2020 | Hafez et al. | |
| 2021/0000588 A1 | 1/2021 | Cain | |
| 2021/0077276 A1 | 3/2021 | Garvey et al. | |
| 2021/0085483 A1 | 3/2021 | MacMillan et al. | |
| 2021/0093461 A1 | 4/2021 | Kowalczyk et al. | |
| 2021/0110605 A1 | 4/2021 | Haslam et al. | |
| 2021/0113222 A1 | 4/2021 | Khatibi et al. | |
| 2021/0121298 A1 | 4/2021 | Walker et al. | |
| 2021/0216683 A1* | 7/2021 | Rai | B29C 64/386 |
| 2021/0298908 A1* | 9/2021 | Holmes | B33Y 70/00 |
| 2021/0307765 A1 | 10/2021 | Dumpe et al. | |
| 2021/0316367 A1 | 10/2021 | Padilla et al. | |
| 2021/0340334 A1* | 11/2021 | Portela | C23C 16/01 |
| 2022/0023048 A1* | 1/2022 | Nolens | A61F 2/30767 |
| 2022/0087670 A1* | 3/2022 | Selmoune | A61B 17/0401 |
| 2022/0134639 A1* | 5/2022 | Allen | B33Y 40/20 |
| | | | 264/401 |
| 2022/0142783 A1* | 5/2022 | Ahmadi | A61F 2/3094 |
| 2022/0160519 A1 | 5/2022 | Northcutt et al. | |
| 2022/0168109 A1* | 6/2022 | Giordano | A61F 2/30767 |
| 2022/0226094 A1 | 7/2022 | Chotkowski et al. | |
| 2022/0296386 A1* | 9/2022 | Fang | A61F 2/4455 |
| 2022/0401138 A1 | 12/2022 | Finley et al. | |
| 2023/0122922 A1 | 4/2023 | Daudet | |
| 2023/0190492 A1 | 6/2023 | Marks et al. | |
| 2024/0033092 A1 | 2/2024 | Parthasarathy et al. | |
| 2024/0065767 A1 | 2/2024 | Cordonnier et al. | |

FOREIGN PATENT DOCUMENTS

| | | | |
|---|---|---|---|
| CN | 110090096 | | 8/2019 |
| CN | 110179570 | A | 8/2019 |
| DE | 69806985 | | 6/2003 |
| EP | 1180989 | | 4/2006 |
| EP | 2832321 | | 2/2015 |
| EP | 2635239 | | 7/2017 |
| EP | 2913030 | | 3/2018 |
| EP | 3536354 | A1 | 9/2019 |
| EP | 3586800 | | 1/2020 |
| FR | 3071400 | | 3/2019 |
| JP | 4840886 | | 12/2011 |
| KR | 301007894 | | 5/2019 |
| WO | 2013131066 | A1 | 9/2013 |
| WO | 2014020562 | | 2/2014 |
| WO | 2015054070 | A1 | 4/2015 |
| WO | 2020123295 | A1 | 6/2020 |
| WO | 2023183793 | A2 | 11/2023 |

OTHER PUBLICATIONS

Yan et al., Ti—6Al—4V triply periodic minimal surface structures for bone implants fabricated via selective laser melting, Jul. 9, 2015, Journal of the mechanical behavior of biomedical materials (2015) 61-73 (Year: 2015).*

Yan et al. (Ti-6Al—4V triply periodic minimal surface structures for bone implants fabricated via selective laser melting (Year: 2015).*

Extended European Search Report dated Feb. 12, 2021 for European Patent Application No. EP20196410.3.

Larraona et al., "Radiopaque material for 3D printing scaffolds", XXXV Confreso Anual de la Sociedad Espanola de Ingenieria Biomedica. Bilbao, Nov. 29-Dec. 1, 2017, p. 451-454 (Year: 2017).

Rozema et al., The effects of different steam-sterilization programs on material properties of poly(l-lactide), Journal of Applied Biomaterials, vol. 2, 23-28 (1991) (Year: 1991).

Alt, Sami. "Design for Sterilization Part 1: Steam Sterilization." Material, Material Technology Blog, Jun. 3, 2016, www.material-technology.com/single-post/2016/05/24/Design-for-Sterilization-part-1-Steam-Sterilization.

Ducheyne, Paul. "Comprehensive Biomaterials." Comprehensive Biomaterials, vol. 1, Elsevier, 2011, pp. 135-135.

Anat Ratnovsky et al., Mechanical Properties of Different Airway Stents, Med. Eng'g. Physics, Mar. 2011, at 408., http://www.medengphys.com/article/S1350-4533(15)00042-9/fulltext.

Andrew T. Miller et al., Fatigue of Injection Molded and 30 Printed Polycarbonate Urethane in Solution, 108 Polymer 121 (2017).

Andrew T. Miller et al., Deformation and Fatigue of Tough 30 Printed Elastomer Scaffolds Processed by Fused 3 Deposition Modeling and Continuous Liquid Interface Production, 75 J. Mechanical Behavior Biomedical Materials 1 (2017).

Ortho Spine News, "SeaSpine Announces 25,000th NanoMetalene Implantation", first available Dec. 18, 2019. (https://orthospinenews.com/2019/12/18/seaspine-announces-25000th-nanometalene-implantation/) (Year: 2019).

Restor3d, "Products", first available Sep. 28, 2020. (https://web.archive.org/web/20200928123335/https:/restor3d.com/products) (Year: 2020).

Ortho Spine News, "Nvision Biomedical Technologies: First FDA Clearance for Osteotomy Wedge System", first available Oct. 28, 2020. (https://orthospinenews.com/2020/10/28/nvision-biomedical-technologies-first-fda-clearance-for-osteotomy-wedge-system-made-of-peek-optima-ha-enhanced/) (Year: 2020).

Sina, "Application logic of triple periodic minimum surface", first available Oct. 24, 2020. (https://k.sina.com.cn/article_2422410454_90630cd6001 OOtlbm.html?from=science) (Year: 2020).

3D Adept Media, "Johnson & Johnson Medical", first available Sep. 17, 2018. (https://3dadept.com/johnson-johnson-medical-has-acquired-3d-printed-spmplants-special ist-emerging-implant-technologies/) (Year: 2018).

Additive Orthopaedics, "Additive Orthopaedics 3d Printed Cotton Bone Segment", first available Sep. 19, 2020. (https://web.archive.org/web/20200919145251/https:/www.additiveorthopaedics.com/our-products/cotton/) (Year: 2020).

Indiamart, "Anterior Cervical Fusion Cage for Spine Surgery", first accessed Dec. 9, 2020. (https://www.indiamart.com/proddetail/ anterior-cervical-fusion-cage-12402896897 .html) (Year: 2020).

(56)  References Cited

OTHER PUBLICATIONS

Instagram, "restor3d", first available Jul. 21, 2020. (https://www.instagram.com/p/CC6dztOAKcM/?utm_source=ig_web_link) (Year: 2020).

Cera-Metal orthopedic implant coating, ifdesign.com, Published 2006 , Accessed Jul. 24, 2024, https://ifdesign.com/en/wi nner-ranking/projecUcera-metal/27188.

Does 3D Printing Add Value In Orthopedics?, publication date Apr. 1, 2019, https://www.odtmag.com/issues/2019-04-01 /view_features/does-3d-printing-add-value-in-orthopedics/.

[MTP Hemiarthroplasty Implant Featuring TIDAL Technology ™], cdn.prod.website-files.com, Posted: Mar. 2023 [online], site visited: [Jul. 25, 2024], URL: <https://cdn.prod. website-files.com/65d612f03cc5c490660ab482/65d612f03cc5c490660ab 7 aa_restor3d-MTP-Sales-Sheet. pdf>. (Year: 2023).

3D printing implants: A complete guide, publication date Feb. 1, 2023, https://www.ntop.com/resources/blog/3d-printing-implants-a-complete-guide/.

Cotton Wedge Portfolio, cdn.prod.website-files.com, Published Jun. 1, 2023, Accessed Jul. 25, 2024, URL: https://cdn.prod.website-files.com/65d612f03cc5c490660ab482/65d612f03cc5c490660ab7bd_MKG-010%20 REV01% 20JUN2023%20Wedge%20Portfolio% 20Brochure.pdf (Year: 2023).

3D Printing for Orthopedic Implant, https://www.eplus3d.com/3d-printing-for-orthopedic-implant.html, Accessed Jan. 8, 2025.

Al-Ketan, et al., "Topology-Mechanical Property Relationship of 3D Printed Strut, Skeletal, and Sheet Based Periodic Metallic Cellular Materials", Additive Manufacturing, vol. 19, Dec. 17, 2017, pp. 167-183.

* cited by examiner

1300

1307

1301     1309            1327B 1327A                    1325

1305A                    1317

1318

1305B 1323A                    1323B

1327D 1327C                    1315

1303      1313   1311

1319

2700

3001

3003

3005

2700

SHEET BASED TRIPLY PERIODIC MINIMAL SURFACE IMPLANTS FOR PROMOTING OSSEOINTEGRATION AND METHODS FOR PRODUCING SAME

CROSS REFERENCE TO RELATED APPLICATION

This application is a continuation of U.S. patent application Ser. No. 17/314,357, filed May 7, 2021, entitled "SHEET BASED TRIPLY PERIODIC MINIMAL SURFACE IMPLANTS FOR PROMOTING OSSEOINTEGRATION AND METHODS FOR PRODUCING SAME," which is a continuation of U.S. patent application Ser. No. 16/991,638, filed Aug. 12, 2020, now U.S. Pat. No. 11,026,798, entitled "SHEET BASED TRIPLY PERIODIC MINIMAL SURFACE IMPLANTS FOR PROMOTING OSSEOINTEGRATION AND METHODS FOR PRODUCING SAME", which is a continuation of U.S. patent application Ser. No. 16/737,341, filed Jan. 8, 2020, now U.S. Pat. No. 10,772,732, entitled "SHEET BASED TRIPLY PERIODIC MINIMAL SURFACE IMPLANTS FOR PROMOTING OSSEOINTEGRATION AND METHODS FOR PRODUCING SAME," which are incorporated herein by reference in their entireties.

BACKGROUND

Osseointegration, or growth of bone into an implant, is desirable in many medical implants, and is typically achieved by the use of pores and voids machined into an implant surface. Sufficient stiffness moduli and compressive strength are also desirable in the many medical devices, and are typically achieved by the use of solid-body or node- and/or strut-based structures. However, the previous approaches to providing osseointegration and mechanical performance in an implant may require the compromise of reduced osseointegration to achieve improved mechanical performance, or vice versa.

For example, in previous medical implants, to achieve sufficient compressive strength, the processes include forming the medical implants from substantially solid, non-porous structures, thereby reducing osseointegration capabilities thereof. As another example, in previous medical implants, to achieve sufficient osseointegration, the processes include forming many pores or voids in the structures of the medical implants, thereby increasing a portion of stress concentrations therein and decreasing mechanical performance.

In addition, previous medical implants typically demonstrate isotropic mechanical performances that are unsuitable, for example, in instances where an implant requires a particular stiffness in a first direction and a reduced stiffness in a second direction. Finally, previous processes for producing medical implants via powder bed manufacturing techniques utilize un-refined lasing parameters that cause defect formation throughout the medical implants. The defects, such as void and lack-of fusion defects, can reduce mechanical performance by serving as nucleation sites for cracks and other deforming features leading towards mechanical failure.

As such, there is a long-felt, but unsolved need for a system and/or process of creating less defective medical devices of suitable mechanical performance and osseointegration capacity.

BRIEF SUMMARY OF THE DISCLOSURE

Briefly described, and according to one embodiment, aspects of the present disclosure generally relate to osseointegration-optimized implants and processes for producing the same.

In one or more embodiments, the implants described herein advantageously promote osseointegration. As described herein, osseointegration generally refers to a desirable in-growth of bone into an implanted structure, such as, for example, an implanted cervical cage. In various embodiments, the present implants include sheet-based triply periodic, minimal surfaces (TPMS) and advantageously demonstrate one or more of: 1) stiffness similar to cortical or trabecular bone stiffness; 2) porosity-compressive strength ratios that allow for implant macrostructures that maintain compressive strength sufficient to perform implant functions while providing sufficient porosity for achieving osseointegration; 3) selective anisotropy, thereby allowing for direction-specific mechanical performances; 4) high surface area-volume ratios, thereby allowing for reduced implant sizes/ weight without sacrificing porosity; and 5) zero mean curvature, thereby allowing for reduced stress concentrations, self-support during fabrication, and curved implant surfaces of constant cross-section. In at least one embodiment, the present disclosure includes processes and techniques for fabricating TPMS implants described herein. According to one embodiment, the present processes and techniques provide for TPMS implants that are substantially devoid of defects (e.g., in contrast to previous implants) and that demonstrate novel ratios of porosity and compressive strength, among other desirable mechanical properties.

According to a first aspect, a 3D-printed implant comprising: A) a top surface and a bottom surface; B) a titanium frame comprising: 1) a perimeter portion; and 2) an interior portion bisecting the titanium frame, wherein the perimeter portion and the interior portion define a first void area and a second void area; and C) a titanium sheet-based triply periodic minimal surface (TPMS) portion integrally formed with the titanium frame via SLM 3D printing extending from the top surface through the first void area and the second void area of the titanium frame to the bottom surface, the TPMS portion comprising: 1) a gyroid architecture; 2) a wall density greater than 99%; 3) unit cells with x and y sides of a first length and a z side of a second length; 4) a stiffness modulus of about 3-14 GPa; 5) a porosity of about 55-85%; and 6) an ultimate compression strength of about 50-230 MPa.

According to a second aspect, the 3D-printed implant of the first aspect or any other aspect, wherein the TPMS portion is free of nodes.

According to a third aspect, the 3D-printed implant of the second aspect or any other aspect, further comprising one or more teeth extending from the top surface or bottom surface.

According to a fourth aspect, the 3D-printed implant of the third aspect or any other aspect, wherein the one or more teeth extend from the top or bottom surface along a surface of the titanium frame.

According to a fifth aspect, the 3D-printed implant of the second aspect or any other aspect, wherein the interior portion defines a third void area free of TPMS structures.

According to a sixth aspect, the 3D-printed implant of the fifth aspect or any other aspect, wherein: A) the TPMS portion comprises a wall thickness of about 0.25 mm; B) the stiffness modulus is about 3 GPa; C) the porosity is about 85%; and D) the ultimate compression strength is about 50 MPa.

According to a seventh aspect, the 3D-printed implant of the fifth aspect or any other aspect, wherein: A) the TPMS portion comprises a wall thickness of about 1.00 mm; B) the stiffness modulus is about 14 GPa; C) the porosity is about 55%; and D) the ultimate compression strength is about 227 MPa.

According to an eighth aspect, the 3D-printed implant of the fifth aspect or any other aspect, wherein the second length is equal to the first length.

According to a ninth aspect, the 3D-printed implant of the fifth aspect or any other aspect, wherein the second length is smaller than the first length.

According to a tenth aspect, the 3D-printed implant of the ninth aspect or any other aspect, wherein: A) the x and y sides are approximately 6.0 mm; and B) the z side is approximately 3.0 mm.

According to an eleventh aspect, the 3D-printed implant of the tenth aspect or any other aspect, wherein the 3D-printed implant is anisotropic in an insertion direction.

According to a twelfth aspect, the 3D-printed implant of the eleventh aspect or any other aspect, wherein the 3D-printed implant is a spinal cage.

According to a thirteenth aspect, the 3D-printed implant of the eleventh aspect or any other aspect, wherein the 3D-printed implant is an osteotomy wedge.

According to a fourteenth aspect, a 3D-printed implant comprising: A) a top surface and a bottom surface; B) two titanium sheet based triply periodic minimal surface (TPMS) portions integrally formed with, and bounded by, a titanium frame extending from the top surface to the bottom surface and comprising: 1) a wall density greater than 99%; 2) unit cells with x and y sides of a first length and a z side of a second length; 3) a stiffness modulus of about 3-14 GPa; 4) a porosity of about 55-85%; and 5) an ultimate compression strength of about 50-230 MPa.

According to a fifteenth aspect, the 3D-printed implant of the fourteenth aspect or any other aspect, wherein the titanium frame comprises: A) a perimeter portion; and B) an interior portion bisecting the titanium frame, wherein the perimeter portion and the interior portion define areas comprising the two titanium TPMS portions.

According to a sixteenth aspect, the 3D-printed implant of the fifteenth aspect or any other aspect, wherein the two titanium TPMS portions comprise a gyroid architecture.

According to a seventeenth aspect, the 3D-printed implant of the sixteenth aspect or any other aspect, wherein the two titanium TPMS portions are free of nodes.

According to an eighteenth aspect, the 3D-printed implant of the seventeenth aspect or any other aspect, wherein the interior portion defines a third void area free of TPMS structures.

According to a nineteenth aspect, the 3D-printed implant of the eighteenth aspect or any other aspect, further comprising one or more teeth extending from the top surface or the bottom surface.

According to a twentieth aspect, the 3D-printed implant of the nineteenth aspect or any other aspect, wherein the second is length smaller than the first length and the 3D-printed implant is anisotropic in an insertion direction.

According to a twenty-first aspect, the 3D-printed implant of the nineteenth aspect or any other aspect, wherein the second length is equal to the first length.

According to a twenty-second aspect, the 3D-printed implant of the twenty-first aspect or any other aspect, wherein the two titanium TPMS portions comprise a wall density of greater than 99%.

These and other aspects, features, and benefits of the claimed implants and processes will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE FIGURES

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

Figures 1A, 1B, 1C:
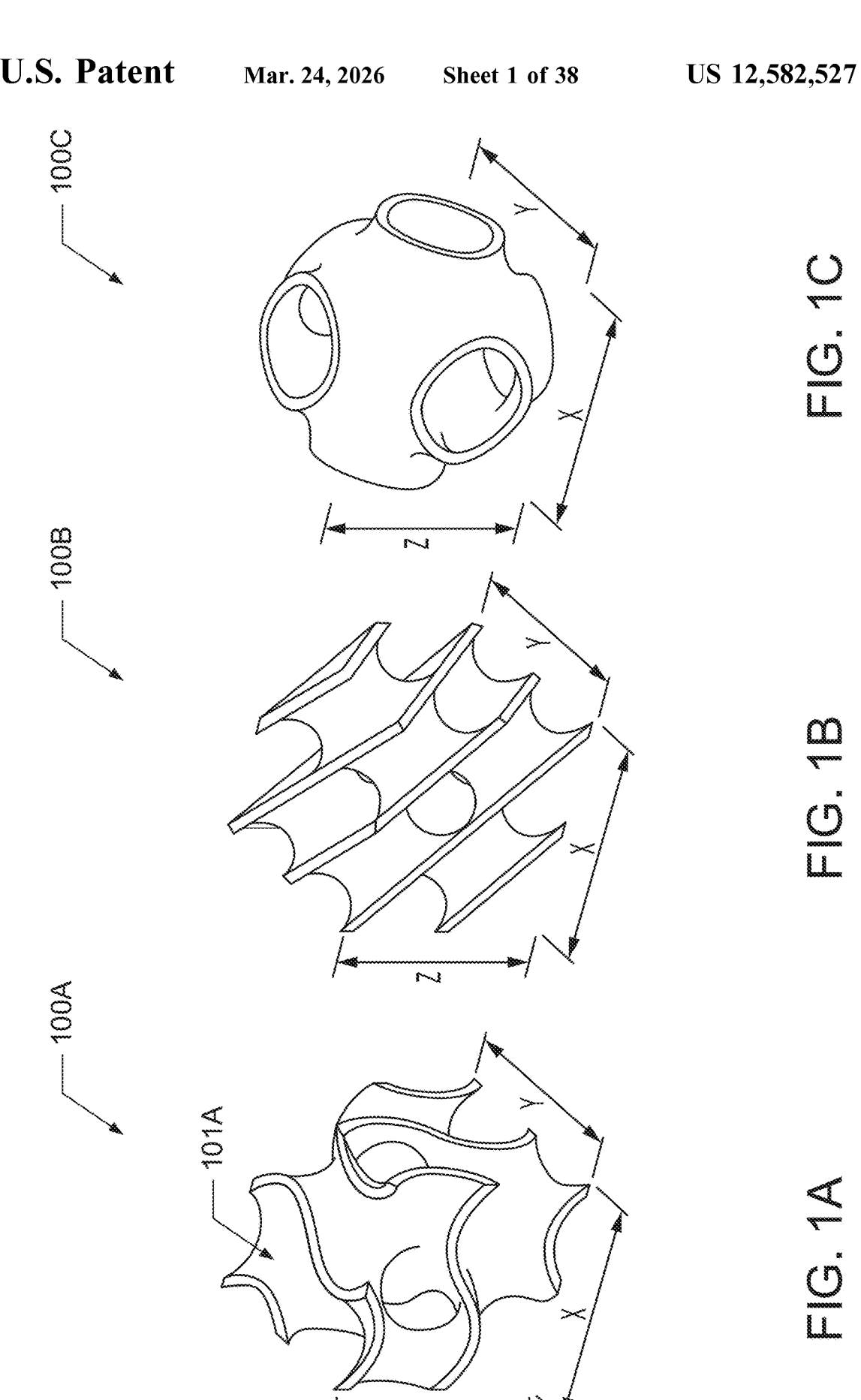
FIGS. 1A-C illustrate exemplary triply periodic, minimal surface (TPMS) structures, according to one embodiment of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

Aspects of the present disclosure generally relate to sheet-based triply periodic, minimal surface (TPMS) implants (and methods for producing the same) that promote osseointegration.

In various embodiments, triply periodic, minimal surface (TPMS) structures generally refer to function-based architectures that demonstrate zero mean curvature, among other properties. As described herein, in at least one embodiment, TPMS structures may be ideal for tissue engineering applications due to, capability for a high surface area to volume ratio, permeability (e.g., porosity), and related weight (e.g., as compared to a bulk material).

In one or more embodiments, the TPMS structures described herein provide for novel ratios of porosity and compressive strength (e.g., high porosity and high compressive strength). In at least one embodiment, the implants described herein demonstrate higher porosity and higher compressive strength than previous implants of equivalent purpose. In one or more embodiments, due to the increased porosity and compressive strength, the implants described herein include reduced weights and/or footprints as compared to weights and footprints of previous implants.

In various embodiments, the present implants include programmed anisotropic properties that allow the present implants to demonstrate varied mechanical properties that are direction dependent. In at least one embodiment, the present anisotropic implants demonstrate an increased compressive strength along an insertion direction and a reduced stiffness along a loading direction.

In at least one embodiment, the present implants include one or more TPMS structures including, but not limited to: 1) gyroid structures, approximated by Equation 1; 2) Schwarz diamond structures, approximated by Equation 2; 3) Schwarz primitive structures, approximated by Equation 3; and 4) other TPMS structures.

$$\cos x \sin y + \cos y \sin z + \cos z \sin x = 0 \qquad \text{(Equation 1)}$$

$$\sin x \sin y \sin z + \sin x \cos y \cos z + \cos x \cos y \sin z = 0 \qquad \text{(Equation 2)}$$

$$\cos x + \cos y + \cos z = 0 \qquad \text{(Equation 3)}$$

Generally, previous implant structures are based on node and/or strut constructs that result in stress concentrations, which may undesirably introduce structural weaknesses or failure points. In contrast, according to one embodiment, an implant including a sheet-based TPMS structure, such as a gyroid, does not demonstrate the stress concentrations of the previous implants, thereby resulting in a stronger implant structure.

In at least one embodiment, the present sheet-based TPMS structures are produced by additive manufacturing methods, such as, for example, laser powder bed fusion, including, but not limited to, selective laser melting (SLM) processes. As described herein, a laser powder bed fusion process refers to a technique of iteratively lasing and melting a (typically metal) powder material into stacked patterns to create a layered, three-dimensional structure. As described herein, previous SLM process parameters typically result in defective structures that may undesirably deform or otherwise fail to demonstrate expected theoretical parameters (such as an expected porosity or strength). For example, sheet-based TPMS implants produced using default SLM parameters exhibit internal void defects that serve as sites for crack initiation, which may lead to structural failure. In at least one embodiment, to generate ideal sheet-based TPMS structures, one or more sets of refined SLM parameters (identified by the inventors and described herein) may be utilized.

According to one embodiment, an SLM process includes melting a layer of powder into a predetermined pattern (e.g., a "slice" of a desired three-dimensional structure). To melt the layer, a laser may execute a first "contour" scan to melt contours (e.g., walls or an outline) of a pattern and a second "infill" scan to melt powder within the contours. Previous approaches to SLM processes utilize default and, in some approaches, identical laser parameters between the contour scan and the infill scan. However, as described herein, use of identical and default laser parameters between the contour and infill scans may result in a defective sheet-based TPMS implant due to the introduction of void defects within the walls of the structure that reduce a density of the walls to suboptimal levels.

In at least one embodiment, to prevent or reduce introduction of void defects, a novel SLM process may be utilized. According to one embodiment, in contrast to previous approaches, the novel SLM process utilizes non-default and non-matching laser parameters for the contour and infill scans. For example, a previous SLM process performs a contour scan and an infill scan under laser parameters of 100 Watts (W), 2800 mm/s scanning speed, and 50 μm focus. In a contrasting example, an embodiment of the present SLM process performs a contour scan under laser parameters of 100 W, 2800 mm/s scanning speed, and 50 μm focus, and performs an infill scan under laser parameters of 145 W, 1000 mm/s scanning speed, and 50 μm focus.

Exemplary Embodiments

Referring now to the figures, for the purposes of example and explanation of the fundamental processes and components of the disclosed implants and methods, reference is made to the figures, which describe one or more embodiments and/or aspects of the present implants and processes. As will be understood and appreciated, the embodiments and aspects discussed herein may not represent every embodiment of the present implants and processes, and additional embodiments will become apparent to those skilled in the art to which the claimed implants and methods pertain without departing from their spirit and scope.

TPMS Structures

FIGS. 1A-C show exemplary gyroid lattice 100A (FIG. 1A), Schwarz-diamond lattice 100B (FIG. 1B), and Schwarz-primitive lattice 100C (FIG. 1C). In various embodiments, the lattices 100A-C demonstrate features further described herein including, but not limited to, zero mean curvature, high ratio of surface area to volume, and high ratio of porosity to compressive strength. In one or more embodiments, the lattices 100A-C can be fabricated according to one or more additive manufacturing processes. According to one embodiment, the lattices 100A-C are entirely self-supporting structures and, thus, can be manufactured without inclusion of support structures, such as, for example, raftering, thereby potentially reducing materials required to fabricate the lattices 100A-C.

According to one embodiment, in contrast to strut- and/or node-based lattice structures, the lattice 100A does not include any substantial regions or points of stress concentration, because the lattice 100A includes only sinusoidal, curved, non-planar surfaces. In at least one embodiment, the lack of substantial stress concentrations in the lattice 100A provides for improved compressive resistance to fatigue (e.g., in comparison to the strut- and/or node-based structures), because stress may be equitably distributed across the lattice 100A.

In one or more embodiments, the lattice 100A includes triply periodic, minimal surface (TPMS) structures 101A. According to one embodiment, the TPMS structures 101A demonstrate a fractal-like behavior in response to being divided or portioned. In at least one embodiment, the fractal-like behavior generally refers to a quality of the TPMS structure 101A where, upon being divided into two, secondary TPMS structures 101A, each secondary structure 101A demonstrates surfaces and curvatures substantially identical to the primary TPMS structure 101A. In other words, in at least one embodiment, the TPMS structure 101A does not appear truncated when "cropped" (e.g., sliced programmatically) into a desired geometry, such as a curved geometry. In one or more embodiments, because the TPMS structure 101A demonstrates the fractal-like behavior, a plurality of the lattice 100A may be readily arranged and sliced (e.g., programmatically in software) into spheres, ellipsoids, and other curved shapes without disrupting the TPMS structures 101A of which the plurality of lattices 100A are composed and without introducing stress concentrations. In at least embodiment, no matter how a TPMS structure is sliced, such as the structure shown at 101A, the resulting substructures have substantially similar properties as the original structure.

In at least one embodiment, the lattices 100A-C include sheet-based TPMS sheets described herein. According to one embodiment, a plurality of the lattices 100A, 100B, or 100C are arranged (e.g., integrally formed in an additive manufacturing process) to create a TPMS architecture, and a plurality of the TPMS unit cells are integrally formed to create a sheet-based TPMS structure, such as, for example, a medical implant. In one or more embodiments, the sheet-based TPMS structure includes only non-planar surfaces (e.g., the TPMS structure excludes nodes).

FIG. 1B shows an exemplary Schwarz-diamond (Schwarz-D) lattice 100B.

FIG. 1C shows an exemplary Schwarz-primitive (Schwarz-P) lattice 100C.

Figure 2A:
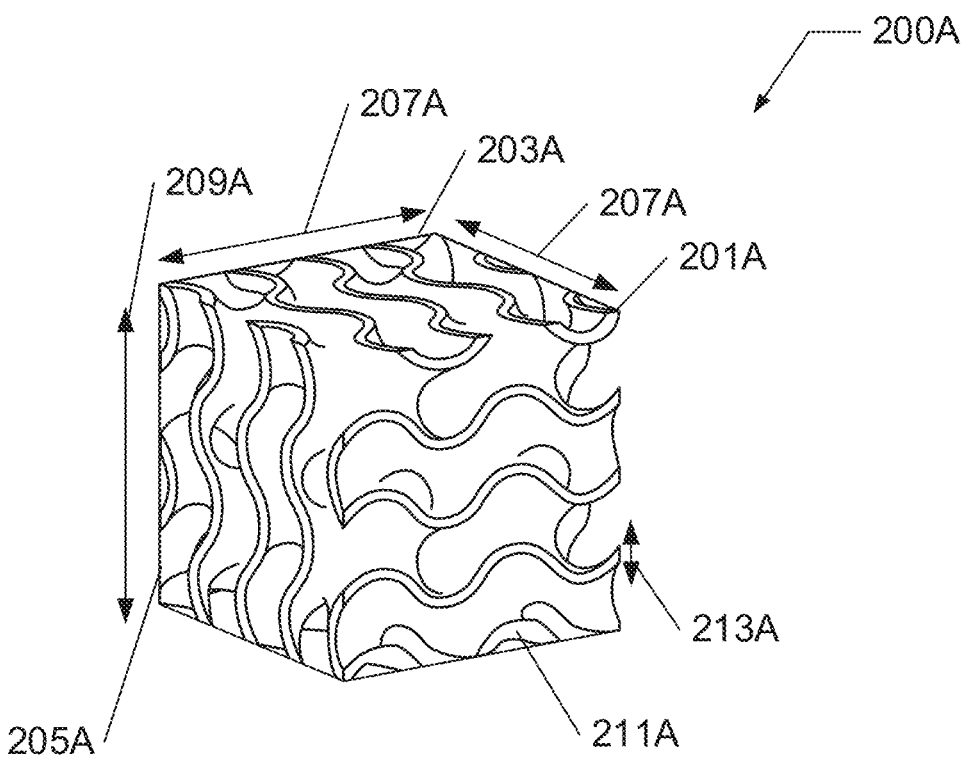
FIGS. 2A-C illustrate exemplary isotropic TPMS unit cells, according to one embodiment of the present disclosure.
Figure 13:
FIG. 13 illustrates a perspective view of a triply periodic, minimal surface (TPMS) implant, according to one embodiment of the present disclosure.

FIG. 2A shows an exemplary unit cell 200A. As used herein, "unit cell" refers generally to a base geometry defined by one iteration of a sinusoidal equation (e.g., such as any of the Equations 1-3 described herein). In one or more embodiments, a unit cell can be repeated in x-, y-, and z-dimensions to conform to one or more void areas defined by a frame of an implant (or other suitable area). In various embodiments, a unit cell is repeated to fill, as shown in FIG. 13, one or more void areas 1315 defined by a frame 1307. According to one embodiment, as further discussed herein, a side length of the unit cell is adjusted to vary one or more physical and/or mechanical properties.

In various embodiments, the unit cell 200A includes one or more integrally formed gyroid lattices 100A described herein. In one or more embodiments, a plurality of the unit cells 200A are arranged to form an implant. In at least one embodiment, because of the continuous and connected curvature of the gyroid lattices, the implant demonstrates an increased surface area-volume ratio as compared to previous implants that include a node- or strut-based or solid-body structure. In one or more embodiments, the increased surface area-volume ratio also permits the implant to be of a reduced mass as compared to a mass of the previous implants that is required to achieve the same surface area-volume ratio. Thus, according to one embodiment, the unit cells 200A are of advantageously reduced mass, increased surface area-volume ratio, and increased porosity as compared to the unit cells (or equivalent composite structure) of previous implants.

In various embodiments, the unit cell 200A includes an x-side 201A, a y-side 203A, and a z-side 205A. In various embodiments the x-side 201A, the y-side 203A, and the z-side 205A are of equal length, thereby defining an isotropic quality of the unit cell 200A. According to one embodiment, as used herein, isotropic generally refers to a quality of a structure where the side lengths of a unit cell (e.g., x-side, y-side, and z-side) are of equal lengths. In various embodiments, the x-side 201A, y-side 203A, and z-side 205A are of equal length, thereby providing for substantially equal material density in the unit cell 200A in all directions and thus providing the isotropic quality of the unit cell 200A.

In at least one embodiment, the unit cell 200A includes more material in an insertion direction (e.g., a direction running from a proximal end to a distal end of one or more implants described herein) and less material in a loading direction oriented perpendicular to the insertion axis. In one or more embodiments, because of the disparate material densities, the unit cell 200A demonstrates a greater stiffness along the insertion axis than along the loading axis (e.g., the implant is anisotropic, at least with respect to certain properties). In at least one embodiment, as used herein, anisotropic generally refers to a quality of a structure that is directionally dependent. In at least one embodiment, some implant properties are changed by varying a unit cell length.

In one or more embodiments, one or more of the x-side 201A, y-side 203A, and z-side 205A may deviate in length, resulting in the unit cell 200A demonstrating increased material density and stiffness in the insertion direction and reduced material density and stiffness in the loading direction, and thereby providing the anisotropic quality of the unit cell 200A. In various embodiments, when the unit cell 200A is anisotropic, the x-side 201A and y-side 203A are of a first length 207A, and the z-side 205A is of a second length 209A measuring less than the first length 207A.

According to one embodiment, the unit cell 200A (and other unit cells described herein) includes an anisotropic quality for purposes including, but not limited to: 1) increasing a stiffness modulus in an insertion direction or a loading direction; 2) increasing a radiolucent property of a particular plane of an implant (formed in part from a plurality of the unit cell 200A) for improved resolution in radiography techniques, such as X-ray; and 3) other purposes. In one example, the unit cell 200A demonstrates an anisotropic quality that includes an increased compressive strength in a loading direction (e.g., as a result of increased material density therein) compared to a compressive strength in an imaging plane (e.g., a plane with respect to which the unit cell 200A or an implant formed therefrom is imaged via X-ray). In the same example, the unit cell 200A demonstrates reduced material density in the imaging plane, thereby causing the unit cell 200A to be more radiolucent in the imaging plane and thus resulting in improved imaging resolution when the unit cell 200A is X-rayed along the imaging plane.

In one or more embodiments, the first length 207A measures about 4.0-6.0 mm, or about 3.5-4.0 mm, or about 4.0-4.5 mm, or about 4.5-5.0 mm, or about 5.5-6.0 mm, or about 6.0-6.5 mm. In various embodiments, the second length 209A measures about 3.0-6.0, or about 2.5-3.0 mm, or about 3.0-3.5 mm, or about 3.5-4.0 mm, or about 4.0-4.5 mm, or about 4.5-5.0 mm, or about 5.5-6.0 mm, or about 6.0-6.5 mm. In one example, to achieve the anisotropic quality of the unit cell 200A, the first length 207A measures about 6.0 mm and the second length 209A measures about 3.0 mm.

In at least one embodiment, when the unit cell 200A is anisotropic in the insertion direction, the unit cell 200A can include more material along an insertion axis aligned with the insertion direction and less material along a loading axis oriented perpendicular to the insertion axis. In one or more embodiments, because of the disparate material distribution, the unit cell 200A (or a gyroid architecture 1325, FIG. 13, including a plurality of the unit cell 200A) demonstrates a greater stiffness along the insertion axis than a stiffness along the loading axis. According to one embodiment, the stiffness along the loading axis can be within the range of cortical bone, thereby providing for improved osseointegration in implants including a plurality of the unit cell 200A (e.g., in gyroid architectures 1325 thereof).

In various embodiments, the unit cell 200A includes walls 211A that form gyroid lattices 100A (FIG. 1) that form the unit cell 200A. In various embodiments, the walls 211A include a wall thickness 213A measuring between about 0.2-1.0 mm, or about 0.25 mm, or about 0.1-0.2 mm, or about 0.2-0.3 mm, or about 0.3-0.4 mm, or about 0.4-0.5 mm, or about 0.5-0.6 mm, or about 0.6-0.7 mm, or about 0.7-0.8 mm or about 0.8-0.9 mm, or about 0.9-1.0 mm, or about 1.0-1.1 mm. In one or more embodiments, the walls 211A include a wall density measuring greater than about 99%, greater than about 98%, or greater than about 97%. In at least one embodiment, the unit cell 200A includes a porosity of about 55-85%, or about 55%, or about 85%, or about 50-55%, or about 55-60%, or about 65-70%, or about 75-80%, or about 80-85%, or about 85-90%. In various embodiments, the unit cell 200A demonstrates a stiffness modulus measuring about 3.0-14.0 GPa, or about 2.5-3.0 GPa, or about 3.0-4.0 GPa, or about 4.0-5.0 GPa, or about 5.0-6.0 GPa, or about 6.0-7.0 GPa, or about 7.0-8.0 GPa, or about 8.0-9.0 GPa, or about 9.0-10.0 GPa, or about 10.0-11.0 GPa or about 12.0-13.0 GPa, or about 13.0-14.0 GPa, or about 14.0-14.5 GPa. In one or more embodiments, the unit cell 200A demonstrates an compressive strength measuring about 50.0-227.0 MPa, or about 45.0-50.0 MPa, or about 50.0-75.0 MPa, or about 75.0-100.0 MPa, or about 100.0-125.0 MPa, or about 125.0-150.0 MPa, or about 150.0-175.0 MPa, or about 175.0-200.0 MPa, or about 200.0-227.0 MPa, or about 227.0-230.0 MPa. According to one embodiment, the unit cell 200A demonstrates a compressive strength in the range of cortical bone or trabecular bone.

According to one embodiment, one or more of the first length 207A, second length 209A, and wall thickness 213A provides a particular porosity, particular stiffness modulus, and/or particular compressive strength. In one example, to achieve a porosity of about 85%, a stiffness modulus of about 3.0 GPa and a compressive strength of about 50.0 MPa, the first length 207A and second length 209A are about 6.0 mm and the wall thickness 213 is about 0.25 mm. In another example, to achieve a porosity of about 55%, an effective modulus of about 14.0 GPa, and a compressive strength of about 227.0 MPA, the first length 207A and second length 209A are about 6.0 mm and the wall thickness 213 is about 1.0 mm. In another example, to achieve a porosity of about 85%, the first length 207A and second length 209A are about 4.0 mm and the wall thickness 213 is about 1.0 mm.

Figure 2B:
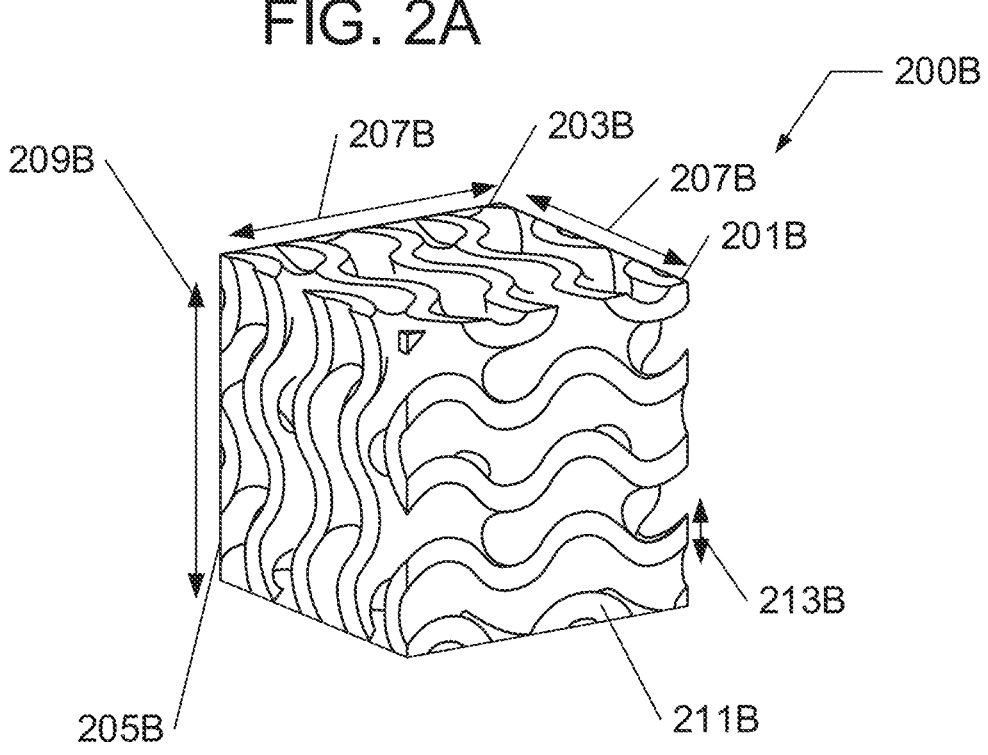

FIG. 2B, shows an exemplary unit cell 200B. In one or more embodiments, the unit cell 200B includes walls 211B that form the one or more gyroid lattices 100A. According to one embodiment, the walls 211B include a wall thickness 213B measuring about 1.0 mm and the unit cell 200B demonstrates a porosity of about 55%, an effective modulus of about 14.0 GPa, and a compressive strength of about 227.0 MPa. In at least one embodiment, the unit cell 200B includes an x-side 201B and a y-side 203B of a first length 207B, and includes a z-side 205B of a second length 209B. In various embodiments, the first length 207B and second length 209B measure about 6.0 mm.

Figure 2C:
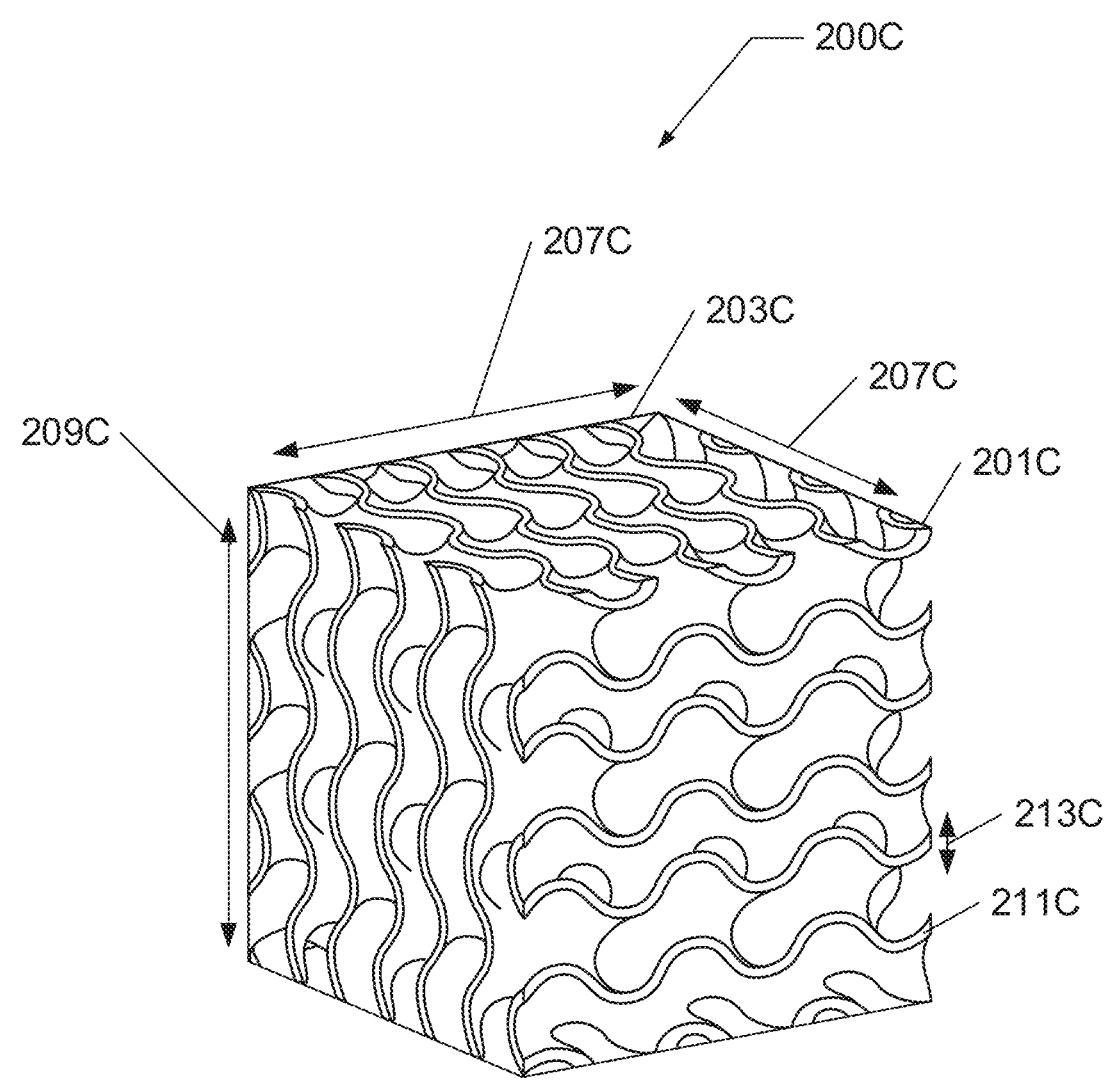

FIG. 2C shows an exemplary unit cell 200C. In one or more embodiments, the unit cell 200C includes walls 211C that form the one or more gyroid lattices 100A that form the unit cell 200C. According to one embodiment, the walls 211C include a wall thickness 213C measuring about 1.0 mm and the unit cell 200C demonstrates a porosity of about 85%. In at least one embodiment, the unit cell 200C includes an x-side 201C and a y-side 203C of a first length 207C, and includes a z-side 205C of a second length 209C. In one or more embodiments, the first length 207B and second length 209B measure about 4.0 mm. In one or more embodiments, the unit cell 200C demonstrates a surface area and a pore size greater than a surface area and pore size demonstrated by the unit cells 200A-B described herein.

Figures 3A, 3B:
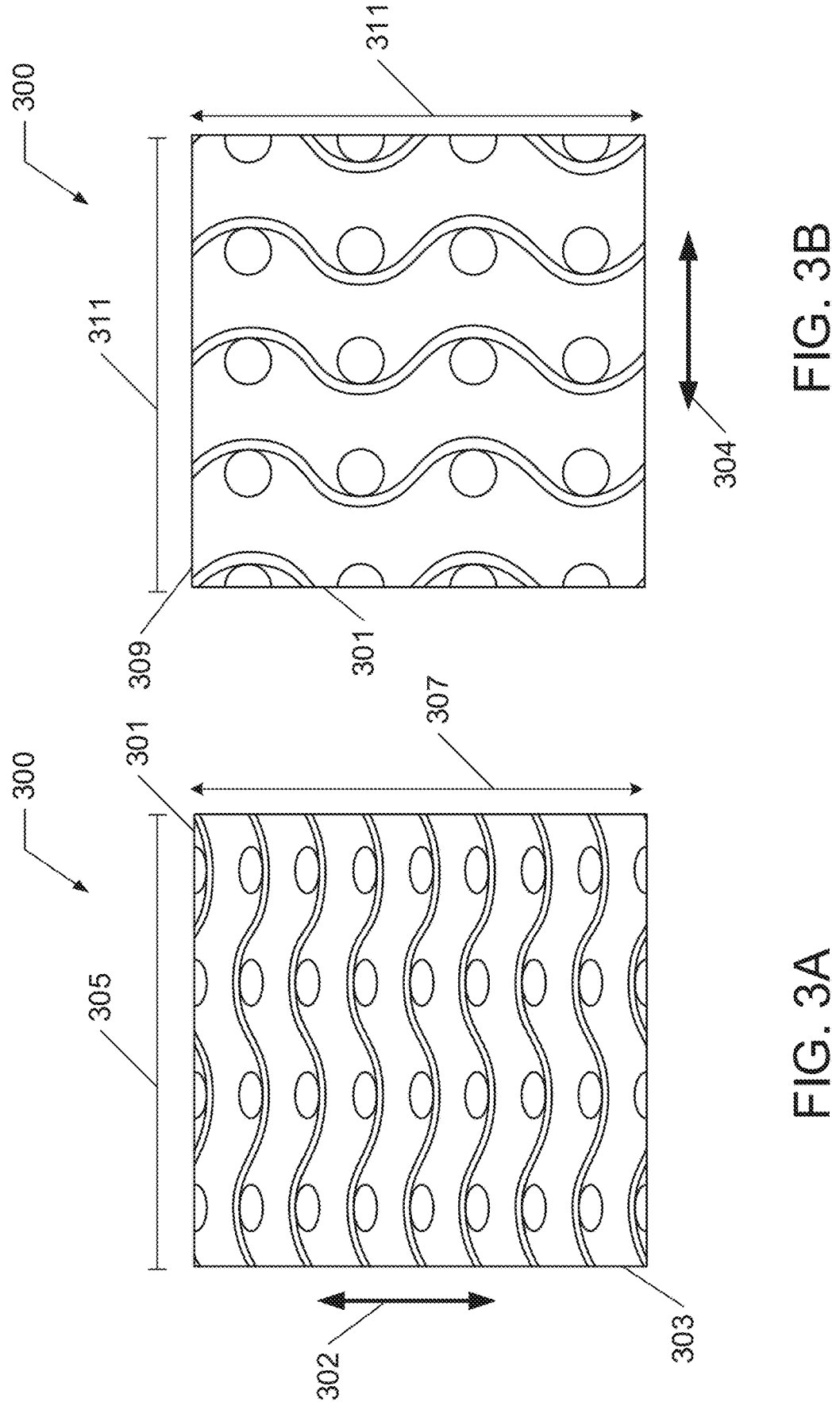
FIGS. 3A-B illustrate exemplary anisotropic and isotropic TPMS structures, according to one embodiment of the present disclosure.

FIG. 3A shows a view in an x-z plane of a sheet-based, TPMS structure 300. According to one embodiment, the structure 300 is anisotropic and demonstrates increased stiffness in an insertion direction and decreased stiffness in a loading direction. In one or more embodiments, the anisotropic quality is provide by varying dimensions of unit cells (such as unit cells 200A-C, FIG. 2) and wall thickness of the structure 300. In at least one embodiment, the aniso-tropic quality provides for direction-specific mechanical performance, such as, for example, increased stiffness in the structure 300 along an insertion direction and a reduced stiffness in the structure 300 along a loading direction.

In at least one embodiment, the structure 300 includes an x-side 301 and a z-side 303. According to one embodiment, the x-side 301 includes an x-length 305 of about 6.0 mm and the z-side 303 includes a z-length 307 of about 3.0 mm. In one or more embodiments, the reduced z-length 307 results in the increased material density in the insertion direction along the insertion axis 302. In at least one embodiment, the increased material density renders the structure 300 aniso-tropic along the z-side 303 and causes the structure 300 to demonstrate an increased stiffness in the insertion direction as compared to a stiffness in other directions, such as, for example in a loading direction along the loading axis 304 (FIG. 3B).

FIG. 3B shows a view in an x-y plane of the structure 300. According to one embodiment, the structure 300 includes the x-side 301 and a y-side 309. In one or more embodi-ments, the structure 300 demonstrates lower stiffness modu-lus in the loading direction along the loading axis 304, as compared to the stiffness modulus along axis 302 of the x-z plane, shown in FIG. 3A. In one or more embodiments, the structure 300 demonstrates lower material density in the loading direction along the loading axis 304 as compared to the material density along axis 302 of the x-z plane, shown in FIG. 3A.

According to one embodiment, the loading direction refers generally to a direction of force applied to the struc-ture 300, for example, when an implant is implanted into a target site. In one or more embodiments, the stiffness in the loading direction is substantially similar in magnitude to a stiffness of trabecular or cortical bone. In at least one embodiment, stiffness substantially matching that of trabe-cular or cortical bone advantageously promotes osseointe-gration of bone into the structure 300.

Figure 4A:
FIGS. 4A-B illustrate exemplary isotropic and anisotropic implants, according to one embodiment of the present disclosure.

FIG. 4A shows an exemplary isotropic implant 400A. According to one embodiment, the implant 400A includes TPMS portions 401A. In at least one embodiment, the TPMS portions 401A are formed from one or more unit cells 200A (FIG. 2A) or other unit cells described herein, the unit cells 200A being formed from gyroid lattices 100A (or other lattices described herein). In at least one embodiment, the TPMS portions 401A demonstrate a substantially equal material density in all directions, resulting in a substantially equal stiffness in all directions and, thus, providing an isotropic quality to the implant 400A. According to one embodiment, the unit cells 200A of the implant 400A include an x-length 403A, z-length 405A, and y-side (not shown) of equal magnitude. In at least one embodiment, because of the equal magnitude, the implant 400A is iso-tropic and demonstrates substantially identical mechanical performance in all directions.

Figure 4B:
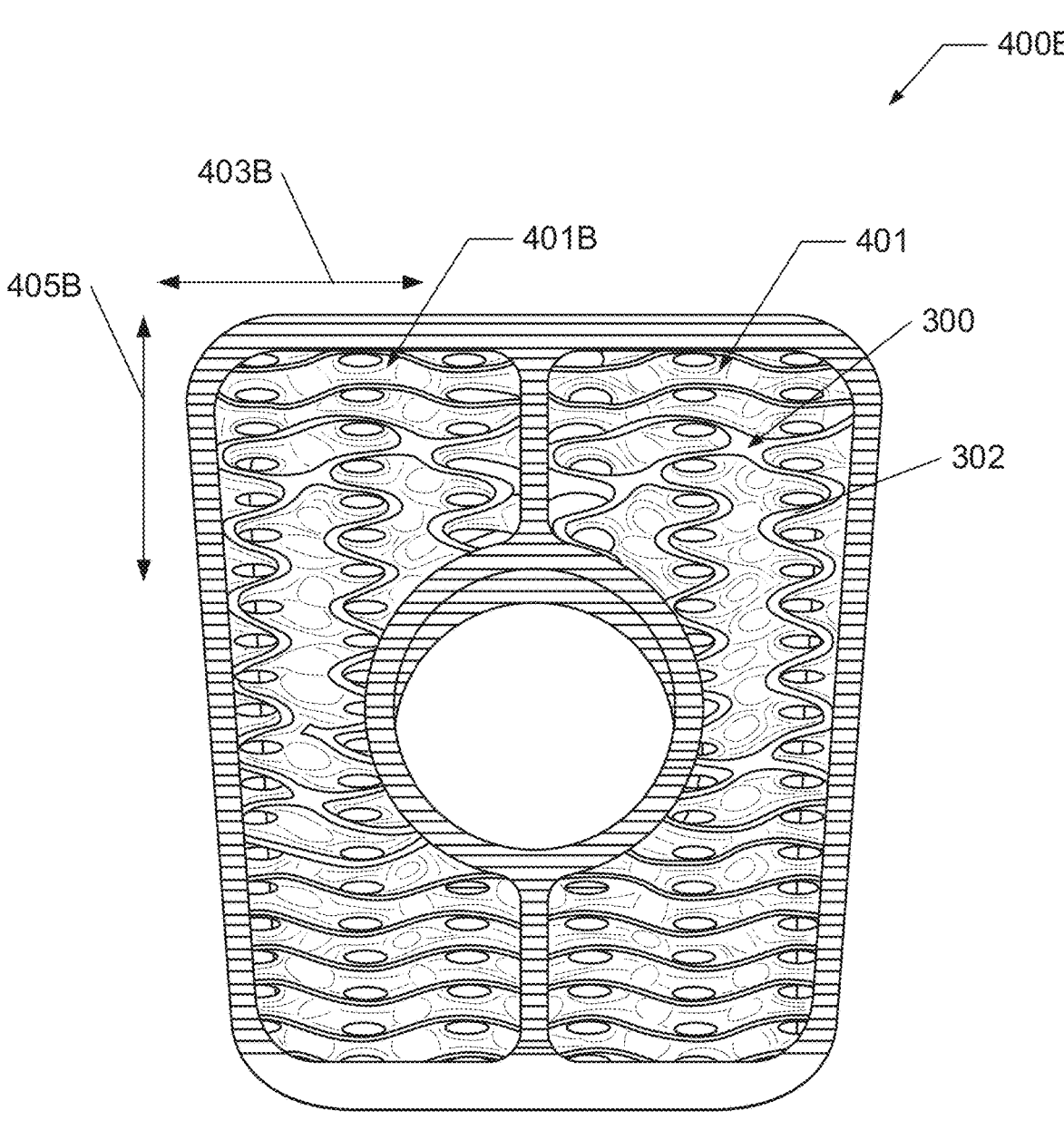

FIG. 4B shows an exemplary anisotropic implant 400B. In at least one embodiment, the implant 400B includes TPMS portions 401B. In various embodiments, the TPMS portions 401B are formed from one or more unit cells 200A-C (FIGS. 2A-C), for example, arranged into one or more TPMS structures 300 (FIG. 3). In one or more embodi-ments, the TPMS portions 401B demonstrate a greater material density in the insertion direction along the insertion axis 302 and a decreased material density in the loading direction along the loading axis 304. In one or more embodi-ments, the disparity in material density results in the implant 400B demonstrating an increased stiffness along the inser-tion direction and a decreased stiffness along the loading direction (e.g., the implant 400B is anisotropic).

According to one embodiment, each of the one or more TPMS structures 300 include an x-length 403B. In one or more embodiments, each of the one or more TPMS struc-tures 300 include a z-length 405B measuring less than the x-length 407B, thereby causing high material density of the TPMS structures 300 along in a direction along the z-length 405B. In one or more embodiments, the high material density in an insertion direction (e.g., the direction along the z-length 405B) causes the implant 400B to demonstrate high compression strength and/or stiffness in the insertion direc-tion.

In one or more embodiments, the increased stiffness in the insertion direction allows the implant 400B to withstand increased loads upon impaction and/or insertion in a target site. According to one embodiment, the lower stiffness in the loading direction allows the implant 400B to demonstrate improved (e.g., more equitable and biologically accurate) load sharing between the implant 400B and bone at the target site. In at least one embodiment, the improved load sharing advantageously increases osseointegration into the implant 400B.

Figure 5:
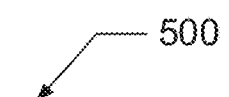
FIG. 5 is a graph relating porosity and compressive strength of various structures, according to one embodiment of the present disclosure.
Figure 5:
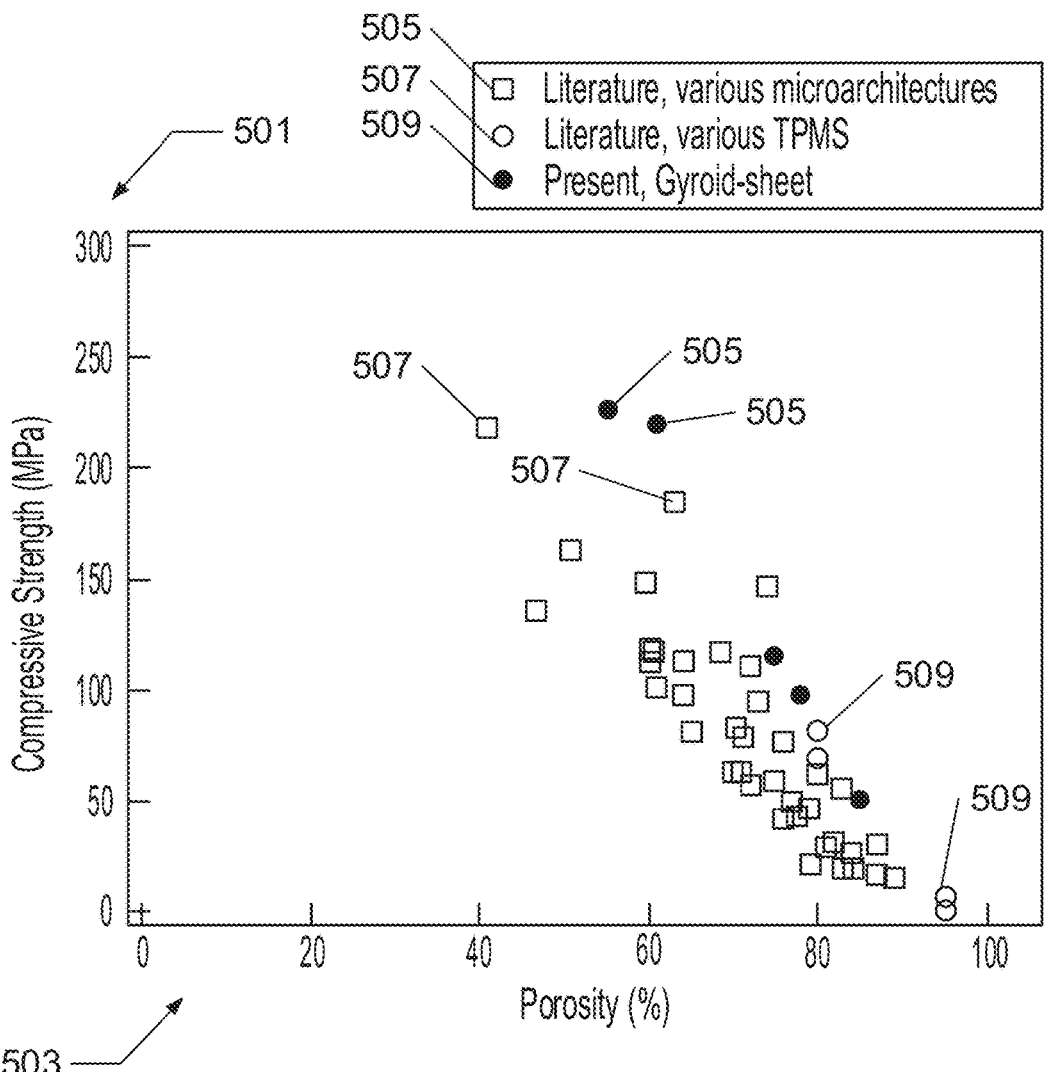

FIG. 5 shows a chart 500 showing compressive strength 501 and porosity 503. In at least one embodiment, the chart 500 compares data points 505 (dark circles) of exemplary sheet-based, TPMS gyroid structures described herein to data points 507 (white squares) of a first set of previous structures and data points 509 (white circles) of a second set of previous structures. According to one embodiment, the data points 509 are associated with TPMS structures pro-duced according to previous implant approaches. In one or more embodiments, the data points 507 are associated with previous microarchitectures discussed in literature. It will be understood that the data shown in chart 500 is exemplary in nature, and properties of exemplary TPMS gyroid structures described herein are not limited to only the data shown in the chart 500.

In one or more embodiments, as shown in the chart 500, the data points 505 demonstrate ratios of porosity 503 to compressive strength 501 greater than any ratio of porosity 503 to compressive strength 501 demonstrated by the data points 507 or the data points 509.

In at least one embodiment, the chart 500 demonstrates that the sheet-based, TPMS gyroid structures described herein demonstrate novel porosity-compressive strength ratios unachievable by previous architectures and structures. In one or more embodiments, the novel porosity-compres-sive strength ratios allow implants produced from the TPMS gyroid structures to demonstrate advantages over previous implants including, but not limited to: 1) increased osseoin-tegration due to increased porosity and stiffness matching;

and 2) reduced weight due to increased porosity that does not result in reduced compressive strength.

Exemplary Processes

Figure 6:
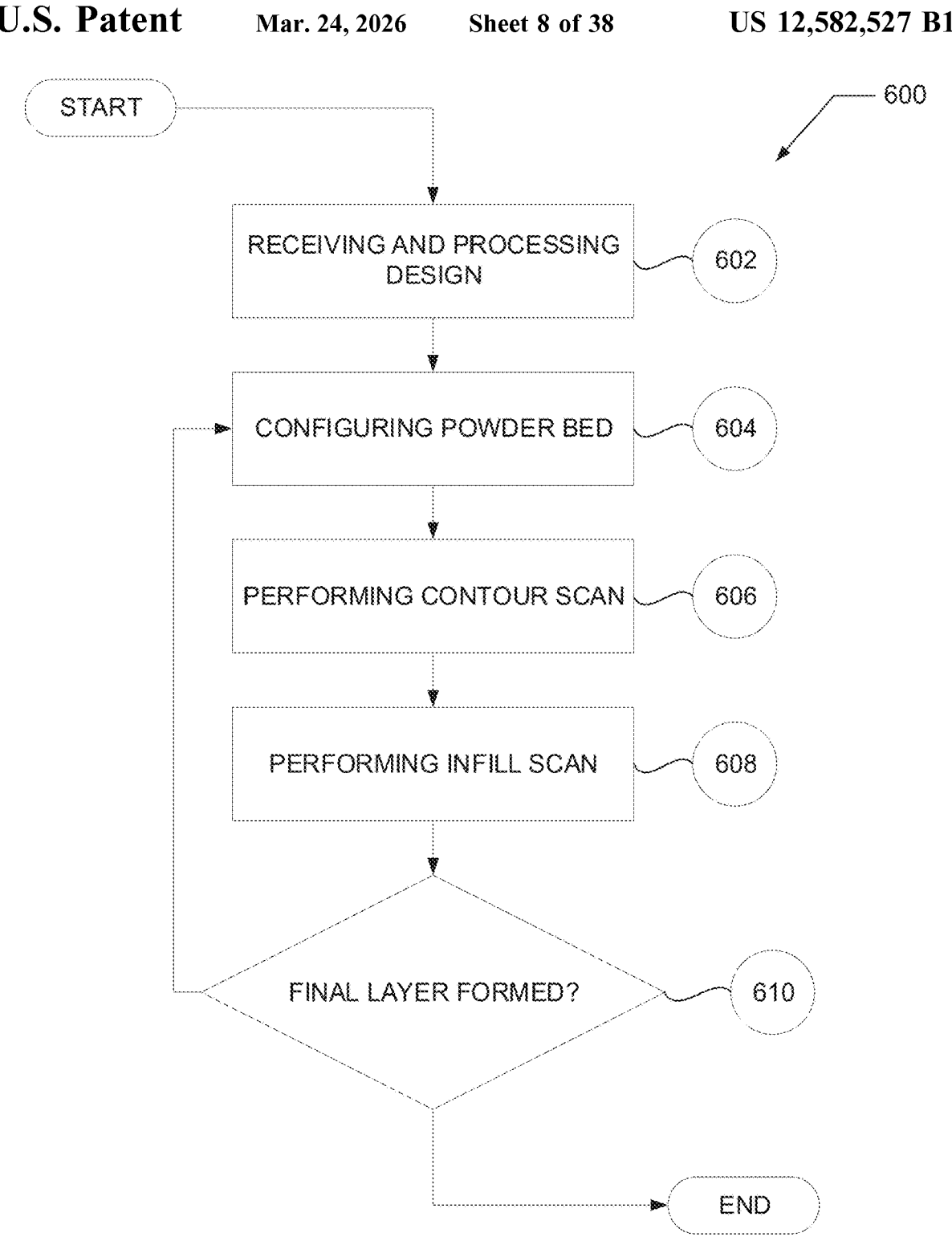
FIG. 6 is a flowchart of an exemplary selective laser melting process, according to one embodiment of the present disclosure.

In various embodiments, FIG. 6 shows a flowchart of an exemplary laser powder bed fusion process (e.g., selective laser melting (SLM) process) 600.

At step 602, the process 600 includes receiving and processing a design for a sheet-based TPMS implant at a computing environment, such as, for example, a computer operating SLM processing and control software. In at least one embodiment, the design may be a computer aided design (CAD) file of various formats including, but not limited to, .STL, .STEP, .PRT, and other CAD formats. In various embodiments, processing the design includes, but is not limited, dividing or slicing the design into a plurality of (effectively) two-dimensional layers. According to one embodiment, each of the plurality of layers include a contour region defining a perimeter of the layer and an infill region defining an interior of the layer. In one or more embodiment, a software tool automatically detects the perimeter of each layer and, using a preselected wall thickness, programmatically defines the contour and infill regions (e.g., and the intersection thereof).

According to one embodiment, step 602 includes determining and assigning a build orientation. In at least one embodiment, the build orientation refers generally to an orientation of a design in the XYZ coordinate system of the build volume during formation within an SLM machine. In various embodiments, the build orientation is an orientation that results in a minimization of contacting surface area between the design and a build platform of the SLM machine. In one or more embodiments, the minimization of contacting surface area via build orientation selection reduces a force and time period required to dislodge a fabricated design (or multiple units thereof) from an SLM machine. According to one embodiment, the build orientation is an orientation wherein a distal end or portion of a design is the portion of the design that contacts the build platform of the SLM machine. In various embodiments, the scanning orientation is a vertical orientation wherein a back or bottom surface (or smallest exterior surface) of a design is the portion of the design that contacts the build platform of the SLM machine.

In one example, the design is for a cervical cage that includes a first side, a second side opposite and parallel to the first side, a third side substantially perpendicular to the first side, and a fourth side opposite and parallel to the third side. In the same example, the first side includes a hole (or other inserter feature) for receiving an inserter. Continuing the same example, at step 602, a scanning orientation for the design includes the second side in contact the build platform of an SLM machine such that, when formed, the hole of the first side is vertically oriented. In the same example, the vertical orientation of the hole allows the hole to be easily and rapidly tapped with threads for the inserter.

In one or more embodiments, the implants described herein can be fabricated (according to the process 600 or other suitable manufacturing processes, such as electron beam melting) such that a hole or void for receiving an inserter is vertically oriented with respect to a surface upon which the implants are formed. In one or more embodiments, because the implants are manufactured in quantities of 100 or more units, the vertical hole orientation of each implant allows for rapid threading of the holes at scale. For example, 100 units of an implant are manufactured on a platform and an inserter feature of each unit is located in a z-axis. In the same example, each unit is manufactured on the platform in an orientation such that the z-axis and the inserter feature are vertically oriented. Continuing the same example, a milling tool passes over the build platform containing the 100 units and rapidly forms threads in the inserter feature of each unit due to all units being properly oriented as a function of their manufactured orientation.

At step 604, the process 600 includes configuring a powder bed, or the like, of an SLM machine that performs SLM fabrication steps to iteratively melt powder into a physical, 3-D rendering of the design received at step 602. In one or more embodiments, a spreading mechanism introduces and evenly distributes powder across a top surface of the powder bed. In at least one embodiment, a laser mechanism is oriented over the powder bed and is operative to move across the powder bed (e.g., in a programmed and electromechanically controlled manner) in any two-dimensional pattern.

In at least one embodiment, configuring the powder bed includes lowering the powder bed by a predetermined increment. In one or more embodiments, the powder bed is lowered each time a contour region and an infill region of a layer of the design is melted into the top surface of the powder bed (e.g., until the final layer thereof is melted into the top surface). In various embodiments, the powder bed is lowered prior to activation of the spreading mechanism.

According to one embodiment, the powder in the powdered bed includes materials including, but not limited to, titanium, cobalt chromium, or a mixture of materials. In one or more embodiments, the powder includes only pre-alloyed materials in powdered form to ensure homogenous melting profiles during steps 606 and 608. In at least one embodiment, particles of the powder include a particle size of about 5.0-75.0 microns, or about 15.0-45.0 microns, or about 5.0-15.0 microns, or about 15.0-25.0 microns, or about 25.0-35.0 microns, or about 35.0-45.0 microns, or about 45.0-55.0 microns, or about 55.0-65.0 microns, or about 65.0-75.0 microns, or about 75.0-85.0 microns. In one or more embodiments, the powder is obtained commercially at the particle size and/or obtained in one or more other forms and modified (e.g., milled, machined, etc.) to create the powder and/or achieve the particle size. According to one embodiment, the particles of the powder can include a spherical shape.

In various embodiments, the powder bed process is performed in an inert atmosphere, such as, for example, an inert argon atmosphere. In at least one embodiment, the atmosphere of the powder bed includes less 10 ppm of oxygen to advantageously limit oxidation of the powder.

At step 606, the process 600 includes performing a contour scan based on a layer of the design received and prepared at step 602. According to one embodiment, the layer is of a thickness of about 10.0-30 microns, or about 5.0-10.0 microns, or about 10.0-15.0 microns, or about 15.0-20.0 microns, or about 20.0-30.0 microns, or about 30.0-40.0 microns. In various embodiments, the design includes layers of different thicknesses.

In at least one embodiment, to perform the contour scan, the SLM machine initiates the laser mechanism according to a predetermined set of contour scan parameters including, but not limited to: 1) a power level; 2) a scanning speed (e.g., a speed with which the laser mechanism moves across the powder bed); 3) laser focus size (e.g., a diameter of a focus point of light emitted by the laser mechanism); 4) hatch angle; 5) hatch spacing; 6) lasing pattern (e.g., such as a hatched pattern, island pattern, etc.); and 7) other lasing parameters, such as, for example, laser pulsing parameters, laser mode, and laser wavelength. In one example, the SLM machine initiates the laser mechanism with contour scan parameters of 125 W, 2800 mm/s scanning speed, and 50 μm laser focus.

According to one embodiment, the SLM machine activates and directs the laser mechanism to melt, into the top layer of the powder bed, a contour of a current layer of the design. In one example, if the current layer of the design is a circle pattern, the SLM machine causes the laser mechanism to melt a circumference of the circle pattern into the top layer of the powder bed. In one or more embodiments, the computing environment and/or SLM machine generates a path and control solution based on the contour of the current layer, and activates electromechanical controllers based on the control solution to guide the laser mechanism along the path and produce the contour region of the current layer.

At step 608, the process 600 includes performing an infill scan within the contour of the contour scan. In at least one embodiment, to perform the infill scan, the SLM machine initiates the laser mechanism according to a predetermined set of infill scan parameters distinct from the contour scan parameters. In one example, the SLM machine initiates the laser mechanism with infill scan parameters of 145 W, 1000 mm/s, and 50 μm laser focus. In one or more embodiments, the infill scan parameters include one or more of a hatch patterning parameter, a hatch spacing parameter, and a hatch spacing parameter. In various embodiments, the hatch patterning parameter generally refers to a path traced by the laser mechanism while performing the infill and/or contour scan, the hatch spacing parameter refers to a distance between lines (e.g., hatches) of melted powder in the infill regions, and the hatch angle parameter refers to a horizontal angle of rotation (e.g., with respect to an origin rotational angle of 0 degrees) at which the infill region (e.g., hatching thereof) is formed.

According to one embodiment, the SLM machine activates and directs the laser mechanism to melt an infill region defined by the area of the top surface of the powder bed contained within the contour region. In one example, if the current layer of the design is a circle pattern, an executed contour scan generates a circular contour and the circular area within the contour defines the infill region.

At step 610, the process 600 includes determining that a final layer of the design has been formed. According to one embodiment, the final layer determination is automatically provided by software of the SLM machine. For example, the software includes a predetermined layer threshold (e.g., equal to the total number of layers in a received and processed design) and a layer counter that is incremented following completion of both a contour and an infill region of each layer. In the same example, when incrementing causes the current value of the layer counter to equal the predetermined layer threshold, the SLM machine determines that the final layer of the design has been formed.

According to one embodiment, if the final layer of the design is determined not to have been formed, the process 600 returns to step 604. In at least one embodiment, the steps 604-606 are repeated to form each layer of a design. In various embodiments, during subsequent iterations of step 604 and/or 606, the laser mechanism can be initiated with an incrementally adjusted hatching angle. In one or more embodiments, during each iteration of the step 604 and/or 606 (e.g., formation of each layer of a design), the hatching angle can be adjusted by about 0.1-90.0 degrees, about 0.1-5.0 degrees, about 5.0-10.0 degrees, about 10.0-15.0 degrees, about 15.0-20.0 degrees, about 20.0-25.0 degrees, about 25.0-30.0 degrees, about 30.0-35.0 degrees, about 35.0-40.0 degrees, about 40.0-45.0 degrees, about 45.0-50.0 degrees, about 50.0-55.0 degrees, about 55.0-60.0 degrees, about 60.0-65.0 degrees, about 65.0-70.0 degrees, about 67.0 degrees, about 70.0-75.0 degrees, or about 75.0-80.0 degrees, about 80.0-85.0 degrees, or about 85.0-90.0 degrees. According to one embodiment, incremental adjustment of the hatching angle at each layer of the design results in an output lacking a seam that, if present, may undesirably create a region of stress concentration that may provide a crack or deformation initiation and propagation site.

In one or more embodiments, after determining that the final layer has been formed, the process 600 concludes and powder may be expelled from the powder bed, allowing for collection of the sheet-based TPMS implant therefrom. In at least one embodiment, if the SLM machine determines that the final layer has not been formed, the process 600 returns to step 604 and the SLM machine re-configures the powder bed and proceeds to steps 606-608 to melt the next layer of the design into the powder bed (e.g., atop previously formed layers).

In at least one embodiment, the process 600 includes scanning and melting multiple layers simultaneously to form multiples of a design. In one or more embodiments, the process 600 is performed on a batch basis to produce a design in quantities ranging from about 2-10,000 units. In various embodiments, in batch-based iterations of the process 600, layers of each unit in a batch are formed simultaneously.

For example, a first contour scan is performed at step 606 to form a contour of a first layer each unit in a batch. In the same example, a first infill scan is performed at step 608 to form an infill region of each unit in the batch. Thus, in the same example, following the first iteration of step 608, the first layer of each unit in the batch is formed, followed by a second layer of the units, until a final layer is reached (e.g., and determined at step 610).

Figures 7A, 7B:
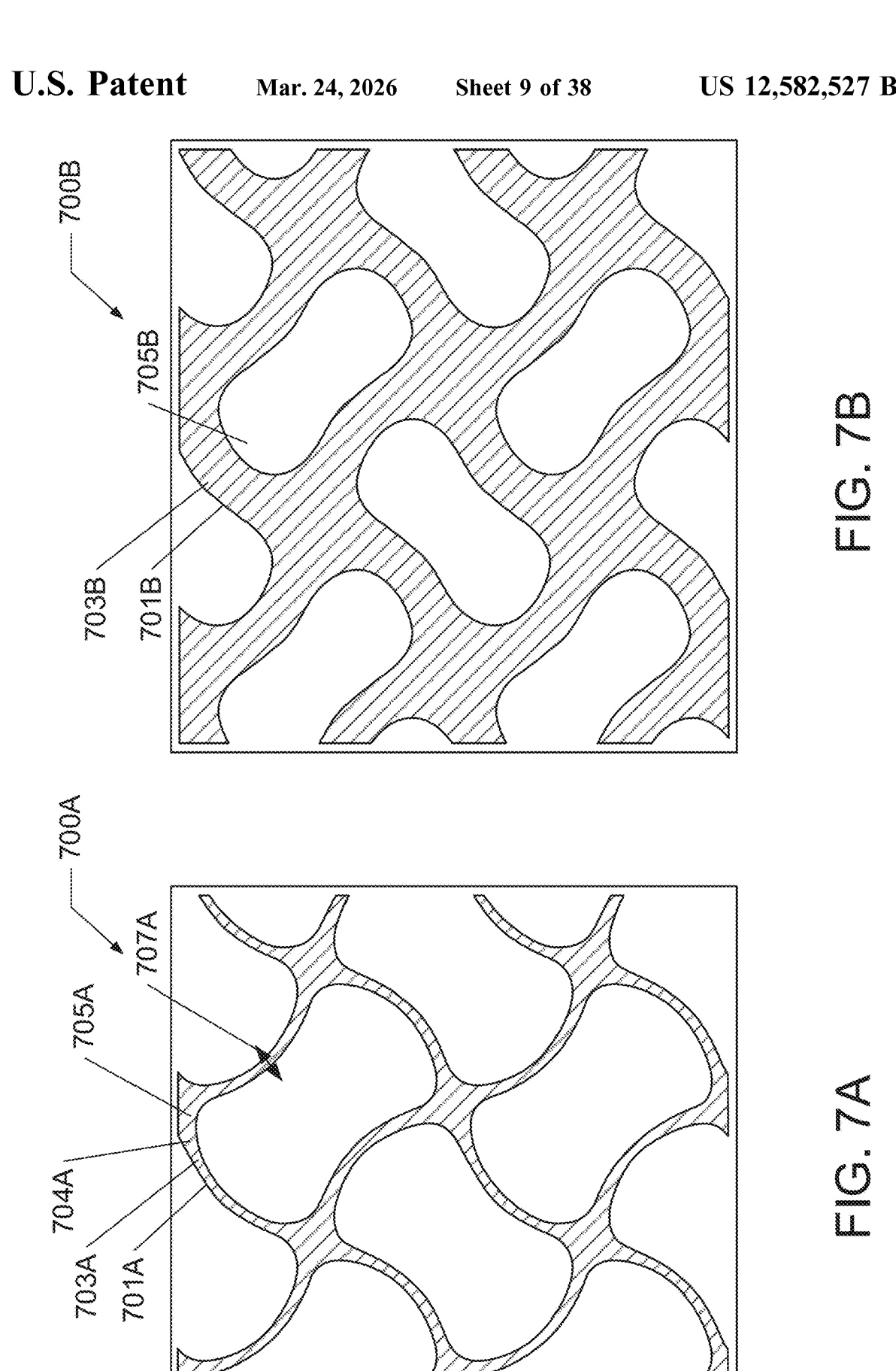
FIGS. 7A-B illustrate exemplary scanning techniques, according to one embodiment of the present disclosure.

FIG. 7A shows an illustration of an exemplary SLM scanning cross-section 700A. In at least one embodiment, the cross-section 700A includes one or more contour regions 701A and one or more infill regions 703A that form walls 705A. In various embodiments, the walls 705A include a wall thickness 707A of about 0.25 mm.

In at least one embodiment, the contour regions 701A are formed by performing step 606 of the process 600 described herein (or by another process, such as an electron beam melting process). In one or more embodiments, the infill regions 703A are formed (e.g., after all of the contour regions 701A are formed) by performing step 608 of the process 600 described herein. In one or more embodiments, the infill regions 703A include hatching 704A of melted powder. In at least one embodiment, a density the hatching 704A determines a density of the walls 705A, and the density of the walls 705A determines at least some mechanical performance parameters of a TPMS structure formed from the walls 705A. For example, a first set of walls 705A with hatching 704A of a first density demonstrates increased compressive strength and stiffness compared to a second set of walls 705A with hatching of a second density less than the first density.

FIG. 7B shows an illustration of an exemplary SLM scanning cross-section 700B. In at least one embodiment, the cross-section 700B includes one or more contour regions 701B and one or more infill regions 703B that form walls 705B. In various embodiments, the walls 705B include a wall thickness 707B of about 1.0 mm.

In one or more embodiments, the cross-section 700B is substantially similar to the cross-section 700A, but includes thicker walls 705B as compared to the walls 705A. In at least one embodiment, the increased wall thickness 707B is achieved by increasing dimensions of the contour regions 701B and forming additional hatching 704B in the infill regions 703B. According to one embodiment, a density of the additional hatching 704B is configured to be greater than, less than, or equal to a density of the hatching 704A depending on desired mechanical properties, an increased density resulting in increased mechanical properties such as compression strength and/or stiffness.

Figures 8A, 8B:
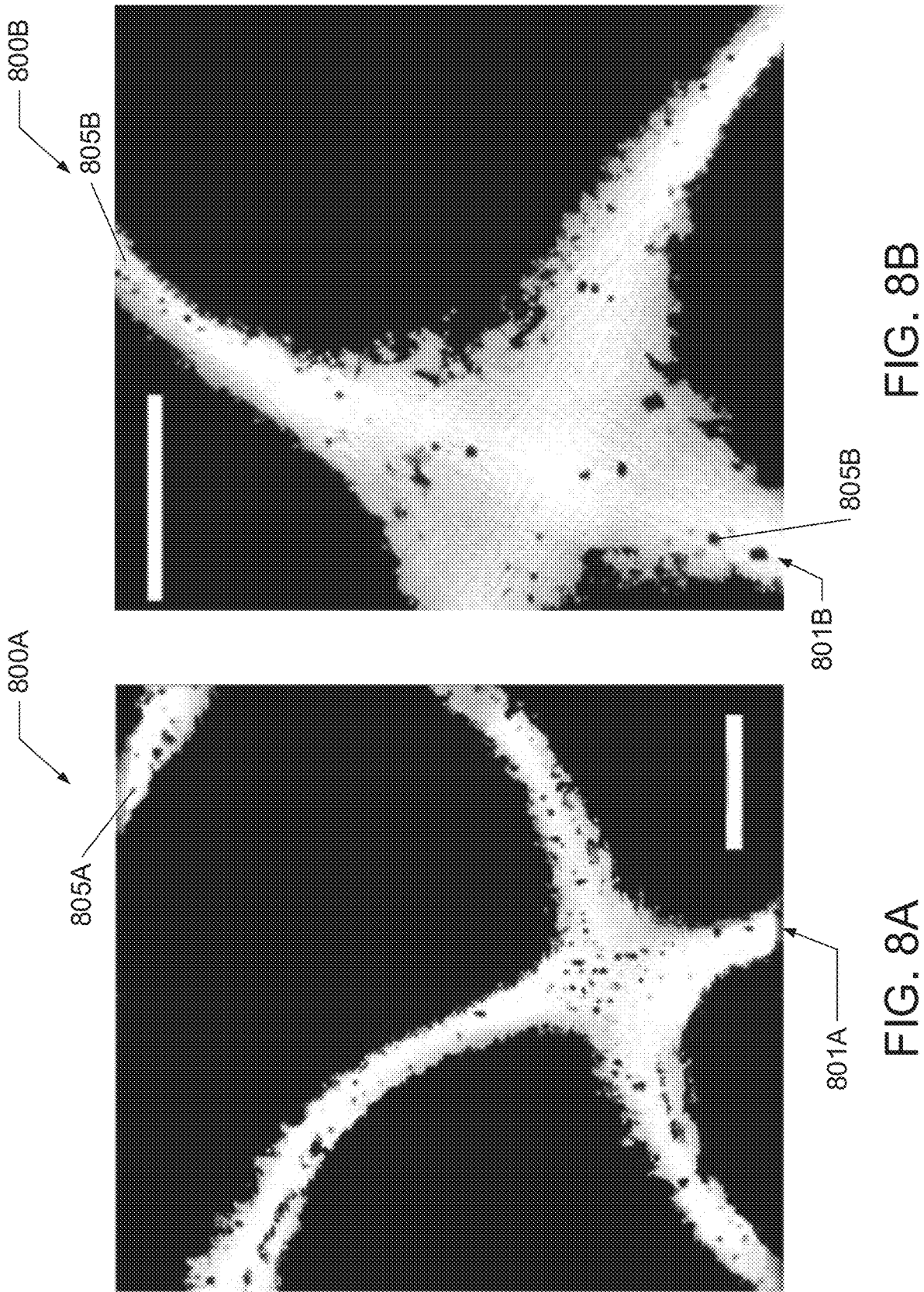
FIGS. 8A-D illustrate exemplary TPMS structure fabrication results, according to one embodiment of the present disclosure.

FIG. 8A shows an exemplary microscopy image of a single laser-scanned layer 800A of a sheet-based TPMS structure. According to one embodiment, the layer 800A includes walls 801A formed according to: 1) contour scan parameters of 100 W laser power, scanning speed of 2800 mm/s, and 50 μm laser focus; and 2) infill scan parameters of 125 W laser power, scanning speed of 2800 mm/s, and 50 μm laser focus. As described herein, the use of an insufficiently low infill laser power and use of identical contour and infill scanning speed parameters can result in formation of large portions of defects in walls of a TPMS structure output from the scanning process. As used herein, defect refers generally to internal void defects and other defects that serve as sites for crack initiation (e.g., leading to structural and/or mechanical failure). In one or more embodiments, the defects include, but are not limited to, internal void defects, concentric wrinkled defects, lack-of-fusion defects (e.g., unmelted particles of powder described herein), and other defects. According to one embodiment, the presence of defects prevents the TPMS structure from demonstrating sufficient wall density, thereby potentially weakening the structure and increasing a likelihood of mechanical underperformance and structural failure.

According to one embodiment, the walls 801A include numerous defects 805A (e.g., observable as black-colored dots) that undesirably reduce a density of the walls 801A from a desired density of above 99% to a suboptimal density of about 96.2%. In one or more embodiments, the density of the walls 801A directly influences a compressive strength and stiffness of a structure, such as a medical implant, formed from a plurality of the layers 800A.

In at least one embodiment, because the walls 801A include the suboptimal density, a medical implant produced therefrom may demonstrate a suboptimal compression strength and stiffness. In one or more embodiments, such a medical implant poses a potential risk when implanted in a patient, because the medical implant may perform in a suboptimal or otherwise unpredictable manner as a result of the suboptimal mechanical parameters.

In one example, a medical implant is fabricated by performing the process 600 according to previous parameters that, as described herein, result in large internal defect formation in walls that form a TPMS structure of the medical implant. In the same example, the large proportion of internal defects reduce a desired wall density to a suboptimal wall density, thereby reducing a desired compression strength and stiffness modulus to suboptimal levels. Continuing the same example, following implantation into a human patient, the medical implant experiences a compressive force of a magnitude that would be tolerable in a medical implant with the desired compression strength and stiffness modulus. In the same example, because the previous approach caused the suboptimal compression strength and stiffness modulus, the medical implant compressively fails (e.g., internally collapses) within the patient, thereby posing potential harm and other complications thereto.

FIG. 8B shows an exemplary microscopy image of a single laser-scanned layer 800B of a sheet-based TPMS structure. According to one embodiment, the layer 800B includes walls 801B formed by performing the process 600 (or another suitable process, such as electron beam melting) according to one or more parameters described herein including, but not limited to: 1) contour scan parameters of 100 W laser power, scanning speed of 2800 mm/s, and 50 μm laser focus; and 2) infill scan parameters of 145 W laser power, scanning speed of 1000 mm/s, and 50 μm laser focus. As described herein, the use of a higher laser power and reduced scanning speed in the infill scan results in a reduction of defect formation and prevalence in an output of the scanning process (e.g., as compared to an output of processes utilizing previous, un-refined scanning parameters).

According to one embodiment, the walls 801B demonstrate defects 805B in a reduced proportion as compared to the proportion of the defects 805A in the walls 801A. In one or more embodiments, due to the reduced proportion of defects, the walls 801B demonstrate a desired wall density of about 99.2%, thereby providing for a desired compression strength and stiffness modulus in a TPMS structure formed from the walls 802B.

In at least one embodiment, the layer 800B demonstrates that the use of parameters discussed herein may result in formation of walls 801B with a reduced proportion of defects 805B. In one or more embodiments, the layer 800B demonstrates that the use of parameters discussed herein may provide for desired mechanical and spatial parameters in a TPMS structure formed therefrom.

Figures 8C, 8D:
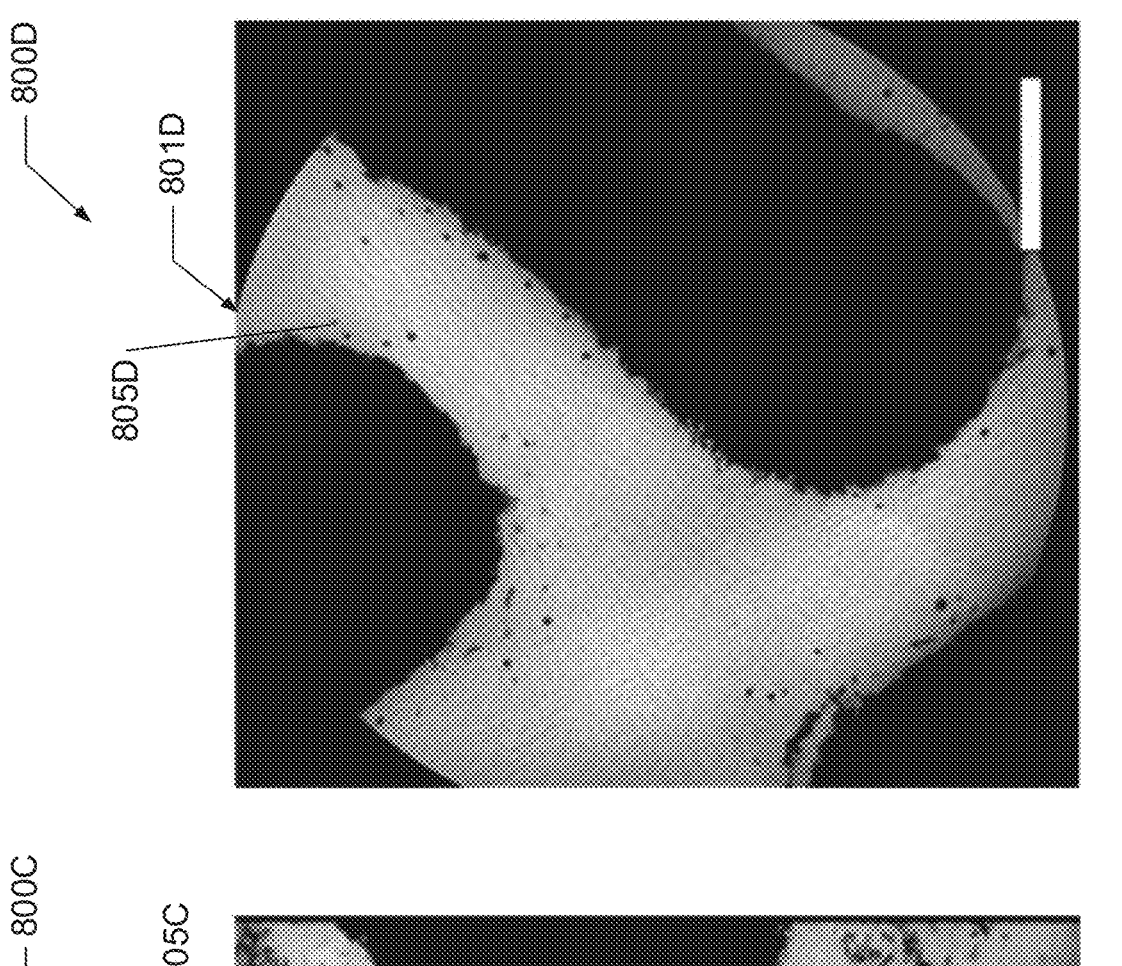

FIG. 8C shows an exemplary microscopy image of a single laser-scanned layer 800C of a sheet-based TPMS structure. According to one embodiment, the layer 800C includes walls 801C formed according to: 1) contour scan parameters of 100 W laser power, scanning speed of 2800 mm/s, and 50 μm laser focus; and 2) infill scan parameters of 125 W laser power, scanning speed of 2800 mm/s, and 50 μm laser focus.

In one or more embodiments, the walls 801C include a large proportion of defects 805C (e.g., similar to the walls 801A and defects 805A). In various embodiments, the defects 805C reduce a density of the walls 801C from a desired density of about 99% or greater to a suboptimal density of about 96.2%. In one or more embodiments, because of the suboptimal density, a TPMS structure formed from a plurality of the layer 800C may demonstrate suboptimal mechanical parameters including, but not limited to, compression strength and stiffness modulus. Thus, according to one embodiment, the above-described parameters results in the formation of the layer 800C in a suboptimal manner that (similar to the layer 800A) demonstrates suboptimal or otherwise unpredictable performance in a medical implant formed from a plurality of the layer 800C.

FIG. 8D shows an exemplary microscopy image of a single laser-scanned layer 800D of a sheet-based TPMS structure. According to one embodiment, the layer 800D includes walls 801D formed according to one or more parameters described herein including, but not limited to: 1) contour scan parameters of 100 W laser power, scanning speed of 2800 mm/s, and 50 μm laser focus; and 2) infill scan parameters of 145 W laser power, scanning speed of 1000 mm/s, and 50 μm laser focus. In various embodiments, the layer 800D includes a contour region 801D and an infill region 800D that form walls 802D.

According to one embodiment, the walls 801D demonstrate defects 805D in a reduced proportion as compared to the proportion of the defects 805C in the walls 801C. In one or more embodiments, due to the reduced proportion of defects, the walls 802D demonstrate a desired wall density of about 99.2%, thereby providing for a desired compression strength and stiffness modulus in a TPMS structure formed from the layers 800D.

In various embodiments, the layers 800B and 800D demonstrate the efficacy of refined parameters described herein in producing walls 802B and 802D with reduced defects 805B and 805D. In at least one embodiment, the defect reduction is a result of increased energy density (e.g., caused by the increased laser power) in the infill scan under the refined parameters (e.g., as compared to the previous, un-refined parameters). According to one embodiment, the increased energy density reduces a prevalence of lack-of-fusion defects, unmelted particles, and other defects in the walls 801B and 801D, thereby providing for precise and accurate wall densities that yield desired mechanical properties in TPMS structures formed therefrom.

Exemplary Implants

According to one or more embodiments, the process 600 (or another suitable process, such as electron beam melting) is performed to create implants with sheet-based, triply-periodic, minimal surface (TPMS) structures described herein (implants discussed herein may also be produced by different or alternative processes). In at least one embodiment, implants discussed herein include at least one portion into which bone and/or soft tissue is desired to grow. In various embodiments, the implants include, but are not limited to: 1) spinal implants, such as, for example, spinal cages; 2) foot implants, such as, for example, osteotomy wedges and other wedge implants; 3) prosthetic implants, such as, for example, a hip prosthesis and 4) custom implants, such as, for example, spherical implants for ankle reconstruction surgeries; 5) implants associated with hemi-arthroplasty of small joints (e.g., first metatarsal-phalangeal (MTP) replacement, radial head replacement, etc.); 6) arthrodesis-related implants; 7) craniomaxillofacial implants; 8) sports medicine-related implants, such as, for example, suture anchors; 9) dental implants; and 10) other implants. In one or more embodiments, FIGS. 9-33 illustrate various implants including TPMS structures described herein. It will be understood by one of ordinary skill in the art that the various implants are exemplary in nature and the present disclosure contemplates inclusion of the described TPMS architectures across a spectrum of implants of varying form, function, and purpose.

Figures 9A, 9B:
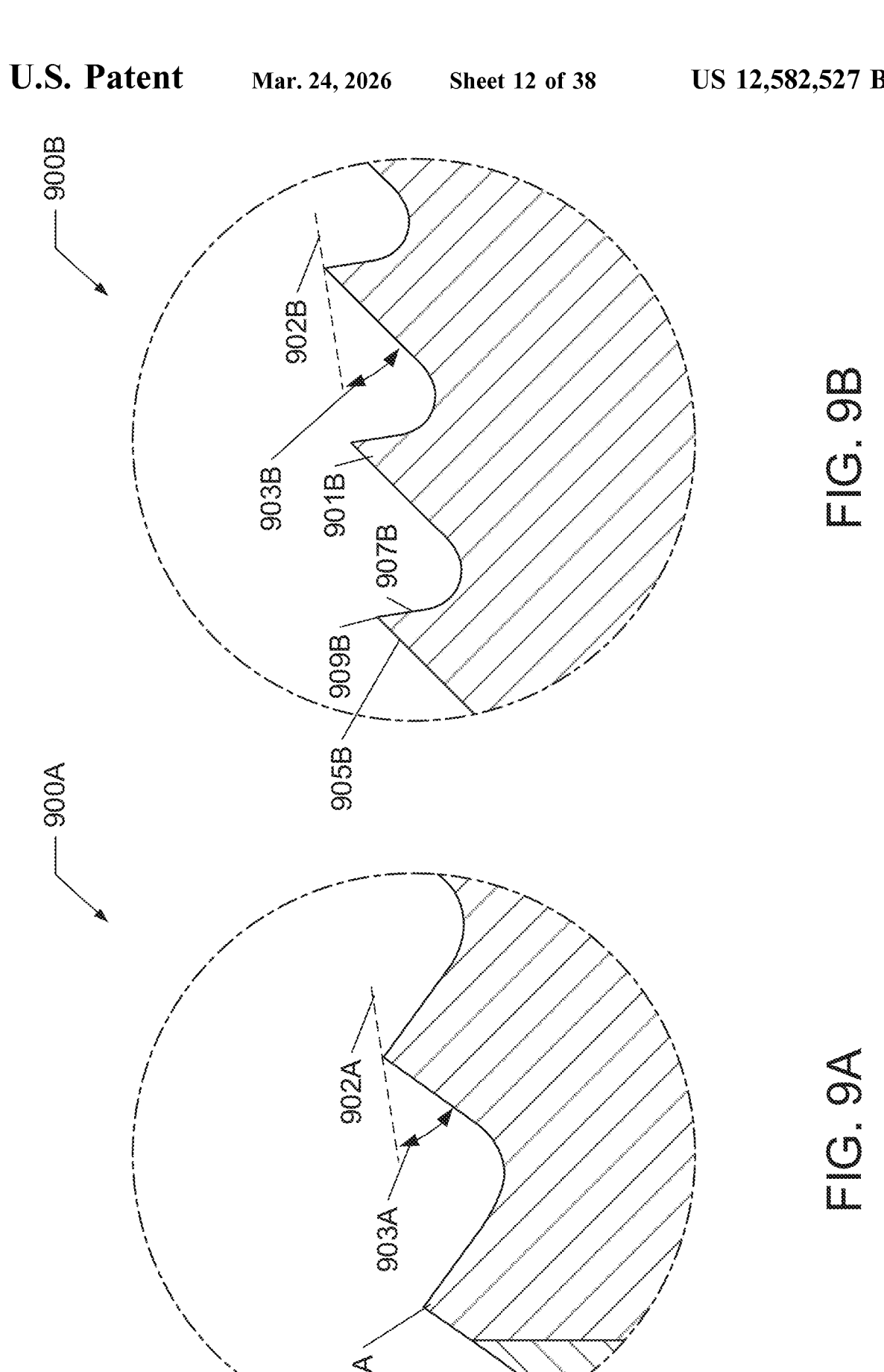
FIGS. 9A-B illustrate exemplary expulsion teeth, according to one embodiment of the present disclosure.

FIG. 9A shows a partial view of an exemplary implant 900A. According to one embodiment, the implant 900A includes one or more teeth 901A. In at least one embodiment, each tooth 901A includes a substantially triangular shape, such as, for example, an equilateral or isosceles triangular shape. In one or more embodiments, each tooth 901A includes a tooth angle 903A that measures about 30.0-60.0 degrees from a plane 902A parallel to the tooth 901A. In at least one embodiment, the tooth 901A is substantially symmetric on each pair of opposing sides thereof.

FIG. 9B shows a partial view of an exemplary implant 900B. According to one embodiment, the implant 900B includes one or more teeth 901B. In at least one embodiment, each tooth 901B includes a substantially triangular shape, such as, for example, a scalene triangular shape. In various embodiments, each tooth 901B includes a saw-tooth shape. In one or more embodiments, each tooth 901B includes a tooth angle 903B that measures about 15.0-60.0 degrees from a plane 902B parallel to the tooth 901B. In at least one embodiment, the tooth 901B includes a first tooth surface 905B oriented at the tooth angle 903B and a second tooth surface 907B, connected to the first tooth surface 905B at a tooth tip 909B. According to one embodiment, the second tooth surface 907B is substantially perpendicular to the plane 902B.

In various embodiments, the one or more teeth 901A or 901B increase resistances of the implants 900A-B to forces that could (otherwise) dislodge the implants 900A-B from a target site. For example, the one or more teeth 901A or 901B increase a pullout force and a pushing force (in a direction opposite the pullout force) required to remove the implants 900A-B from a target site. According to one embodiment, the one or more teeth 901A and 901B are similar to other teeth described herein, such as for example the one or more teeth 1607 and one or more teeth 2307.

Figures 10A, 10B:
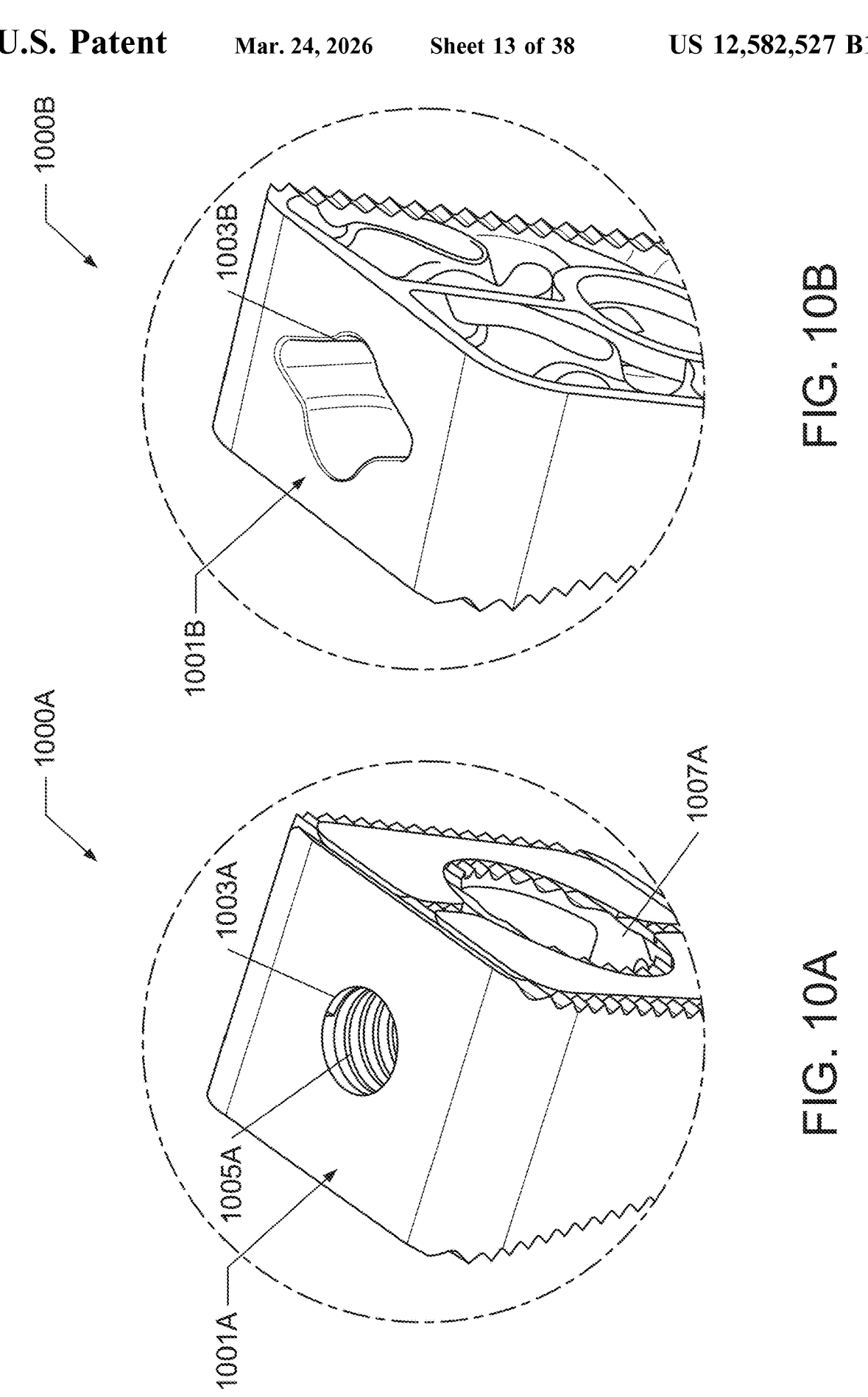
FIGS. 10A-D illustrate exemplary insertion elements, according to one embodiment of the present disclosure.

FIG. 10A shows an exemplary implant 1000A. According to one embodiment, the implant 1000A is similar to one or more implants described herein, such as, for example, the implant 1300, implant 2000, and/or implant 2700. In one or more embodiments, the implant 1000A includes a front portion 1001A. In various embodiments, the front portion 1001A defines or includes a void 1003A that receives, for example, an instrument for inserting the implant 1000A to a target site, or a fixture for securing the implant 1000A within a target site. In at least one embodiment, the void 1003A is centrally located on the front portion 1001A. According to one embodiment, the front portion 1001A defines or includes a plurality of voids 1003A, and, in some embodiments, diameters of the each of the plurality of voids 1003A may be varied. In one or more embodiments, the void 1003A is formed to a particular depth within the front portion 1001A or may penetrate through the front portion 1003A and a central region 1007A therebeneath.

FIG. 10B shows an exemplary implant 1000B. According to one embodiment, the implant 1000B is similar to one or more implants described herein, such as, for example, the implant 1300, implant 2000, and/or implant 2700. In one or more embodiments, the implant 1000B includes a front portion 1001B. In various embodiments, the front portion 1001B includes a keyhole 1003B that accommodates one or more instruments and/or fixtures for inserting or securing the implant 1000B into a target site. In at least one embodiment, the keyhole 1003B includes one or more side walls 1005B. According to one embodiment, the one or more side walls 1005B taper, curve, or otherwise converge towards a central point at a base (not shown) of the keyhole 1003B.

Figures 10C, 10D:
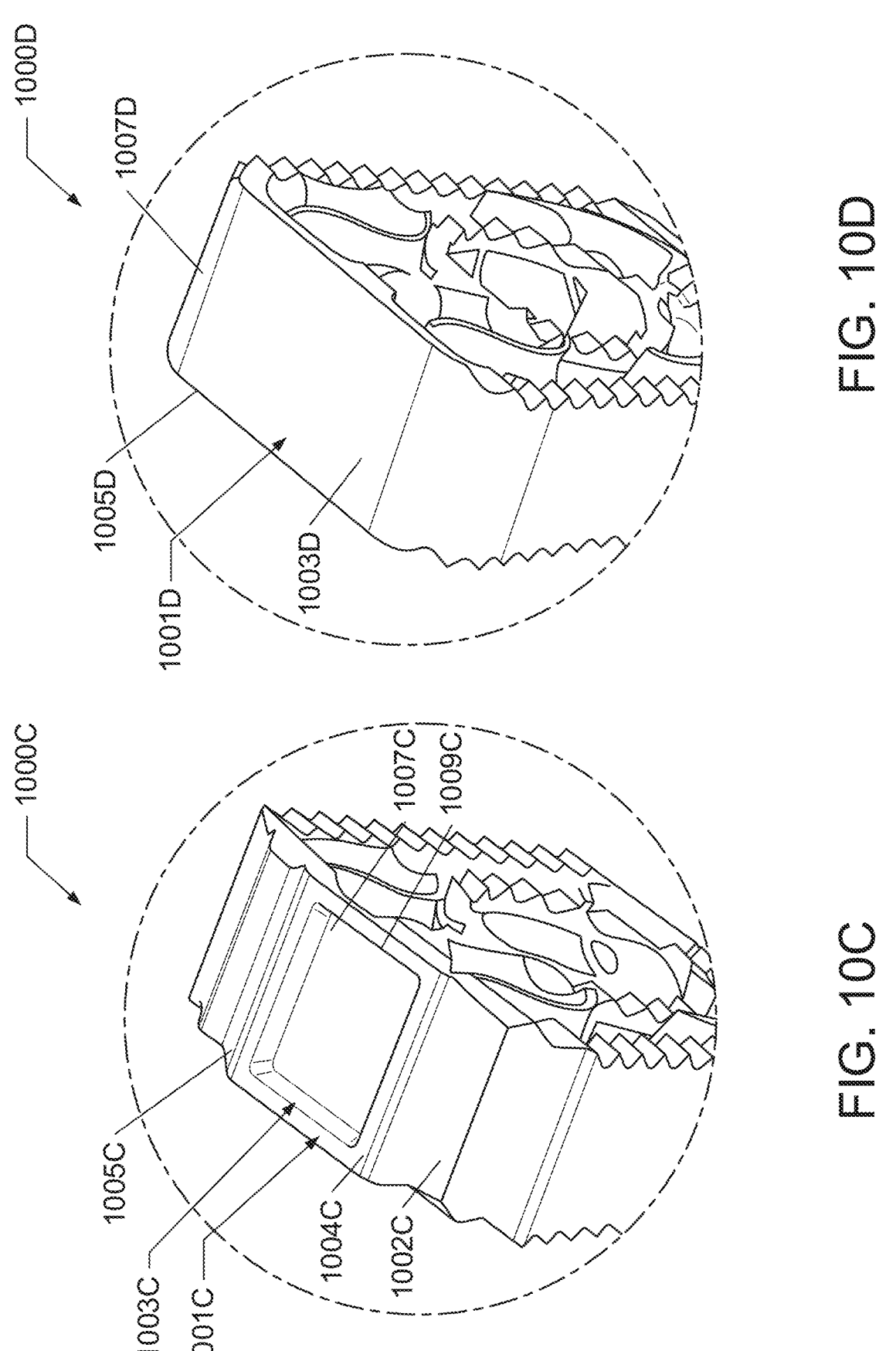

FIG. 10C shows an exemplary implant 1000C. According to one embodiment, the implant 1000C is similar to one or more implants described herein, such as, for example, the implant 1300, implant 2000, and/or implant 2700. In one or more embodiments, the implant 1000C includes a front portion 1001C. In various embodiments, the front portion 1001C includes a divot 1003C that accommodates or interfaces with one or more instruments and/or fixture for inserting or securing the implant 1000C into a target site. In at least one embodiment, the divot 1003C includes one or more shapes including, but not limited to, a substantially quadrilateral shape, a circular shape, an elliptical shape, and other polygon-based shapes.

In various embodiments, the front portion 1001C includes one or more sloped portions 1005C that transition the front portion 1001C from a first plane 1002C to a second plane 1004C. According to one embodiment, a bottom surface 1007C of the divot 1003C is coplanar with the first plane 1002C and a top edge 1009C of the divot 1003C is coplanar with the second plane 1004C.

FIG. 10D shows an exemplary implant 1000D. According to one embodiment, the implant 1000D is similar to one or more implants described herein, such as, for example, the implant 1300, implant 2000, and/or implant 2700. In one or more embodiments, the implant 1000D includes a front portion 1001D. In various embodiments, the front portion 1001D includes a substantially quadrilateral shape. In at least one embodiment, a surface 1003D of the front portion 1001D is substantially flat and includes one or more straight edges 1005D and one or more rounded edges 1007D.

As will be understood, features discussed above in regards to FIGS. 10A-10D may be used in a variety of implants and not just those shown herein.

Figures 11A, 11B:
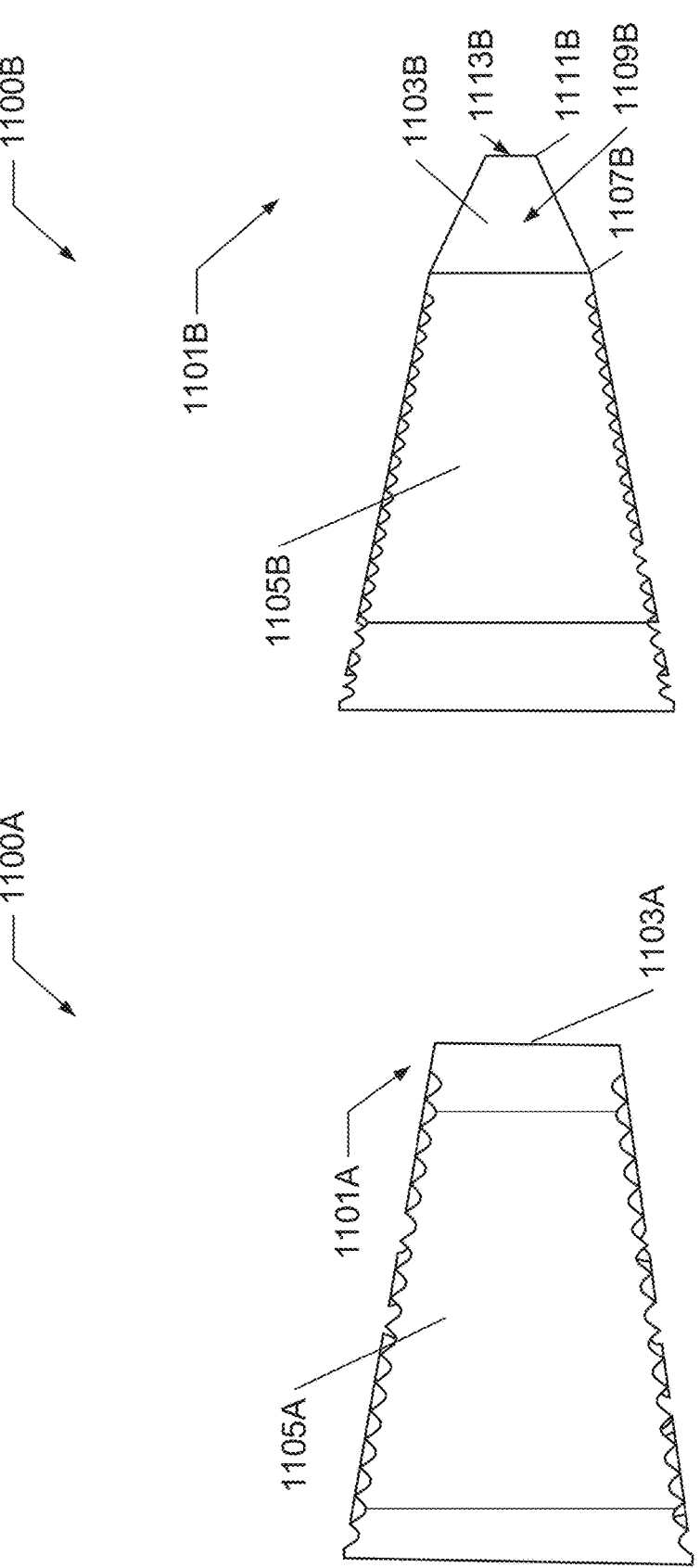
FIGS. 11A-B illustrate exemplary implant profiles, according to one embodiment of the present disclosure.

FIG. 11A shows an exemplary implant 1100A. According to one embodiment, the implant 1100A is similar to one or more implants described herein, such as, for example, the implant 1300, implant 2000, and/or implant 2700. In one or more embodiments, the implant 1100A includes a distal end 1101A. In at least one embodiment, the distal end 1101A includes a tip 1103A to which side surfaces 1105A connect and taper. In various embodiments, the tip 1103A is substantially rounded according to a predetermined radius of curvature. In at least one embodiment, the tip 1103A includes a substantially rounded triangular prism shape. In one or more embodiments, the substantially rounded tip 1103A reduces a risk of the implant 1100A becoming caught on or causing damage to tissue during insertion of the implant 1100A to a target site. According to one embodiment, the side surfaces 1105A taper at a taper angle (not shown) of about 0.5-20.0 degrees, 0.25-2.0 degrees, about 2.0-4.0 degrees, about 4.0-6.0 degrees, about 6.0-8.0 degrees, about 8.0-10.0 degrees, about 10.0-12.0 degrees, about 12.0-14.0 degrees, about 14.0-16.0 degrees, about 16.0-18.0 degrees, or about 18.0-20.0 degrees.

FIG. 11B shows an exemplary implant 1100B. According to one embodiment, the implant 1100B is similar to one or more implants described herein, such as, for example, the implant 1300, implant 2000, and/or implant 2700. In one or more embodiments, the implant 1100B includes a distal end 1101B. In at least one embodiment, the distal end 1101B includes a tip 1103B to which side surfaces 1105B connect and taper. According to one embodiment, the tip 1103 includes a substantially trapezoidal prismatic or pyramidal shape. In various embodiments, the tip 1103B tapers inwards between a proximal point 1107B and a distal point 1111B. According to one embodiment, the taper forms tapered side surfaces 1109B between the proximal point 1107B and distal point 1111B. In at least one embodiment, the tip 1103B includes a substantially flat terminating surface 1113B to which the tapered side surfaces 1109B converge. According to one embodiment, the taper occurs at a predetermined taper angle (not shown) measuring about 3.0-30.0 degrees.

Figures 12A, 12B:
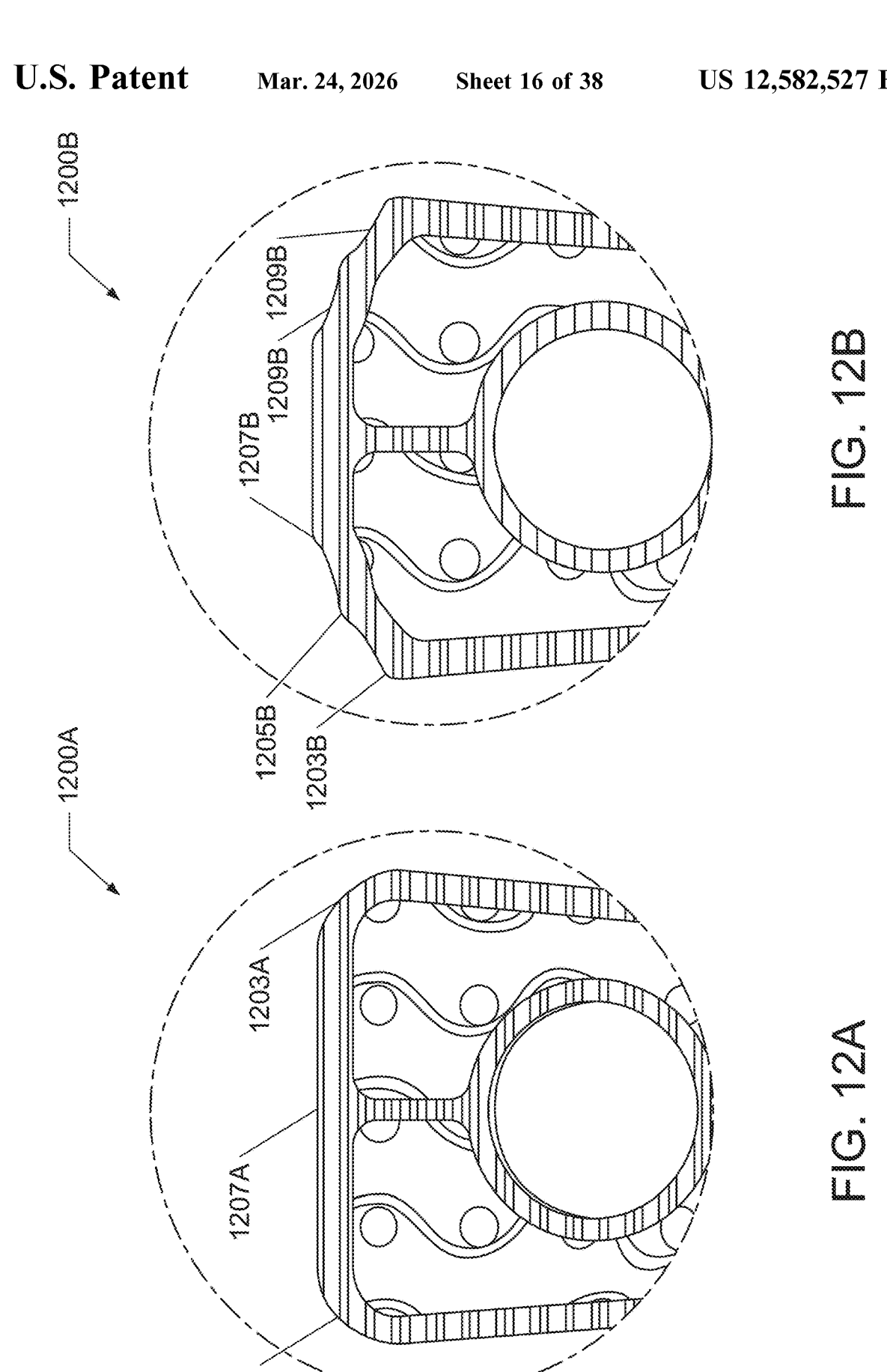
FIGS. 12A-D illustrate exemplary implant profiles, according to one embodiment of the present disclosure.

FIG. 12A shows an exemplary implant 1200A. In various embodiments, the implant 1200A includes corners 1203A that are rounded. According to one embodiment, an implant including non-rounded, pointed corners may demonstrate a sharpened, piercing shape that is more likely than a rounded shape to become caught on tissue and cause piercing or laceration damage during implant insertion and implantation. In at least one embodiment, the corners 1203A include a substantially rounded shape. In various embodiments, the substantially rounded shape reduces the risk of the corners 1203A becoming caught on and causing damage to tissue during insertion and implantation. In various embodiments, a face 1207A connects the corners 1203A, and the face 1207A includes a substantially flat surface (not shown).

FIG. 12B shows an exemplary implant 1200B. In various embodiments, the implant 1200B includes corners 1203B that may be substantially rounded. In at least one embodiment, the implant 1200B includes intermediary corners 1205B and terminating corners 1207B that are each substantially rounded. According to one embodiment, regions between the substantially rounded corners 1203B, intermediary corners 1205B, and terminating corners 1207B include faceted surfaces 1209B crowned on either end by the rounded corners 1203B, intermediary corners 1205B, and/or terminating corners 1207B. According to one embodiment, the faceted surfaces 1209B (or faceted surfaces 1209C, or 1207D discussed herein) allow for minute adjustments of positioning of the implant 1200B during insertion thereof to a target site (e.g., while positioning the implant 1200B at the target site with a tamping and/or inserter instrument). In one example, a surgeon performs a minute position adjustment to an insertion angle of an implant 1200B at a target site by aligning one or more faceted surfaces 1209B thereof to one or more bony structures at a target site.

Figures 12C, 12D:
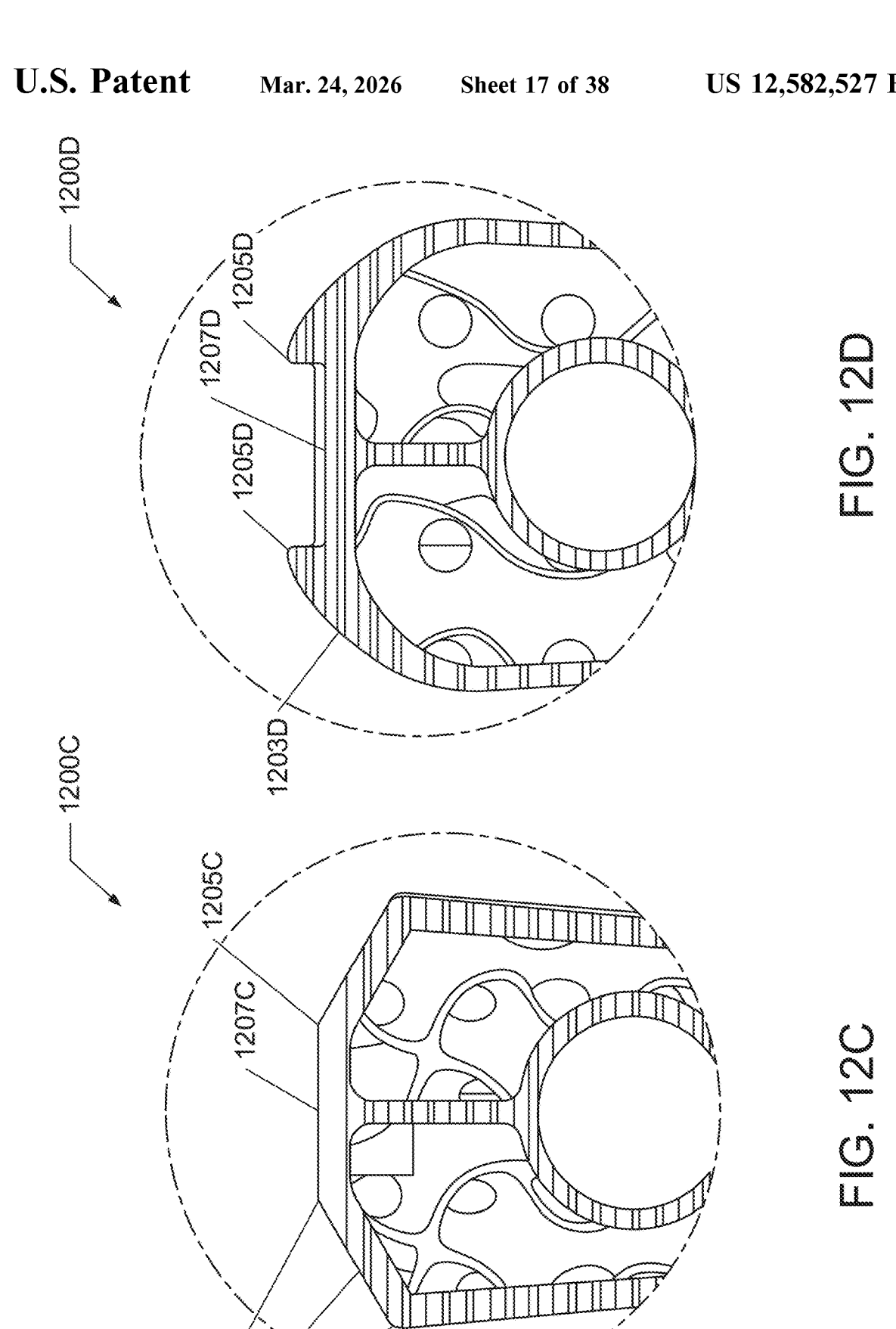

FIG. 12C shows an exemplary implant 1200C. In one or more embodiments, the implant 1200C includes corners 1203C and terminating corners 1205C. According to one embodiment, one or more of the corners 1203C and/or terminating corners 1205C are substantially rounded. In at least one embodiment, regions between the corners 1203C and terminating corners 1205C include substantially flat, faceted surfaces 1207C. FIG. 12D shows an exemplary implant 1200D. In various embodiments, the implant 1200D includes one or more curved surfaces 1203D. In one or more embodiments, the one or more curved surfaces 1203D reduce a risk of the implant 1200D becoming caught on and/or damaging tissue during insertion into a target site.

In at least one embodiment, each of the curved surfaces 1203D terminates at a substantially rounded corner 1205D. According to one embodiment, a region inferior to and between the rounded corners 1205D include a faceted surface 1207D.

FIG. 13 shows a perspective view of an exemplary implant 1300. In various embodiments, the implant 1300 includes one or more materials including, but not limited to: 1) one or more metals, such as titanium; 2) one or more alloys, such as, for example Ti6Al4V ELI alloy; 3) polymers, such as, for example polyether ether ketone (PEEK); and 4) other materials. According to one embodiment, the implant 1300 is a wedge implant, such as, for example, an osteotomy wedge. According to some embodiments, the implant 1300 is a spinal implant, such as, for example, a cervical cage.

In at least one embodiment, the implant 1300 includes a prismatic shape, such as, for example, a wedge shape. In one or more embodiments, the implant 1300 includes one or more shapes including, but not limited to, rectangular prismatic shapes, spherical shapes, ovoid shapes, pyramidal shapes, and solids of revolution, among other shapes. According to one embodiment, the implant 1300 includes one or more shapes that are of an irregular geometry and/or are designed to conform to anatomical structures (for example, bones).

In one or more embodiments, the implant 1300 includes a proximal surface 1301 and a distal surface 1303 connected by side surfaces 1305 at corners 1327 A-D. In at least one embodiment, the proximal surface 1301, distal surface 1303, and side surfaces 1305 form a frame 1307. In one or more embodiments, the frame 1307 includes a perimeter portion 1309 and an interior portion 1311. In various embodiments, the perimeter portion 1309 defines a generally quadrilateral shape and includes the proximal surface 1301, distal surface 1303, and side surfaces 1305. In one or more embodiments, the interior portion 1311 bisects the generally quadrilateral shape, the bisection forming a first void area 1313 and a second void area 1315. In at least one embodiment, the interior portion 1311 includes a central region 1317 that may be substantially circular in shape.

In one or more embodiments, the first void area 1313 and second void area 1315 extends from a top surface 1319 to a bottom surface 1501 (FIG. 15) of the implant 1300. In various embodiments, the implant 1300 includes a sheet-based triply period minimal surface (TPMS) portion 1323 that extends from the top surface 1319, through the first void area 1313 and second void area 1315, to the bottom surface 1501. In one or more embodiments, the TPMS portion 1323 is integrally formed with the frame 1307. In at least one embodiment, the TPMS portion 1323 fills the first void area 1313 and second void area 1315, the TPMS portion 1323 being bisected by the interior portion 1311. According to one embodiment, the interior portion 1311 forms a central region 1317 defining a third void that is devoid of the TPMS portion 1323 (and other TPMS structures). In one or more embodiments, the central region 1317 includes one or more voids 1318 that increase a surface area of the TPMS portion 1323 that is exposed to bone following insertion into a target site.

In one or more embodiments, the TPMS portion 1323B includes a gyroid architecture 1325 formed of gyroid lattice structures described herein, such as, for example, gyroid lattices 100A (FIG. 1A) formed into a plurality of unit cells 200A (FIG. 2A). In one or more embodiments, the TPMS portion 1323B may be an architecture formed of Schwarz-P or Schwarz-D lattice structures described herein, such as, for example, the lattices 100B or 100C (FIGS. 1B-C).

In various embodiments, the TPMS portion 1323B includes mechanical parameters including, but not limited to, a stiffness modulus of about 3.0-14.0 GPA and an ultimate compression strength of about 50.0-230.0 MPa. In one or more embodiments, the TPMS portion 1323 includes a wall density greater than about 99% and a porosity of about 55-85%.

In at least one embodiment, the implant 1300 includes corners 1327 A-D that connect the side surfaces 1305 to the proximal surface 1301 and bottom surface 1303. In one or more embodiments, one or more of the corners 1327 A-D are rounded or may include one or more shapes described herein, such as, for example, one or more shapes of the corners 1203A-D shown in FIGS. 12A-D and described herein.

Figure 14:
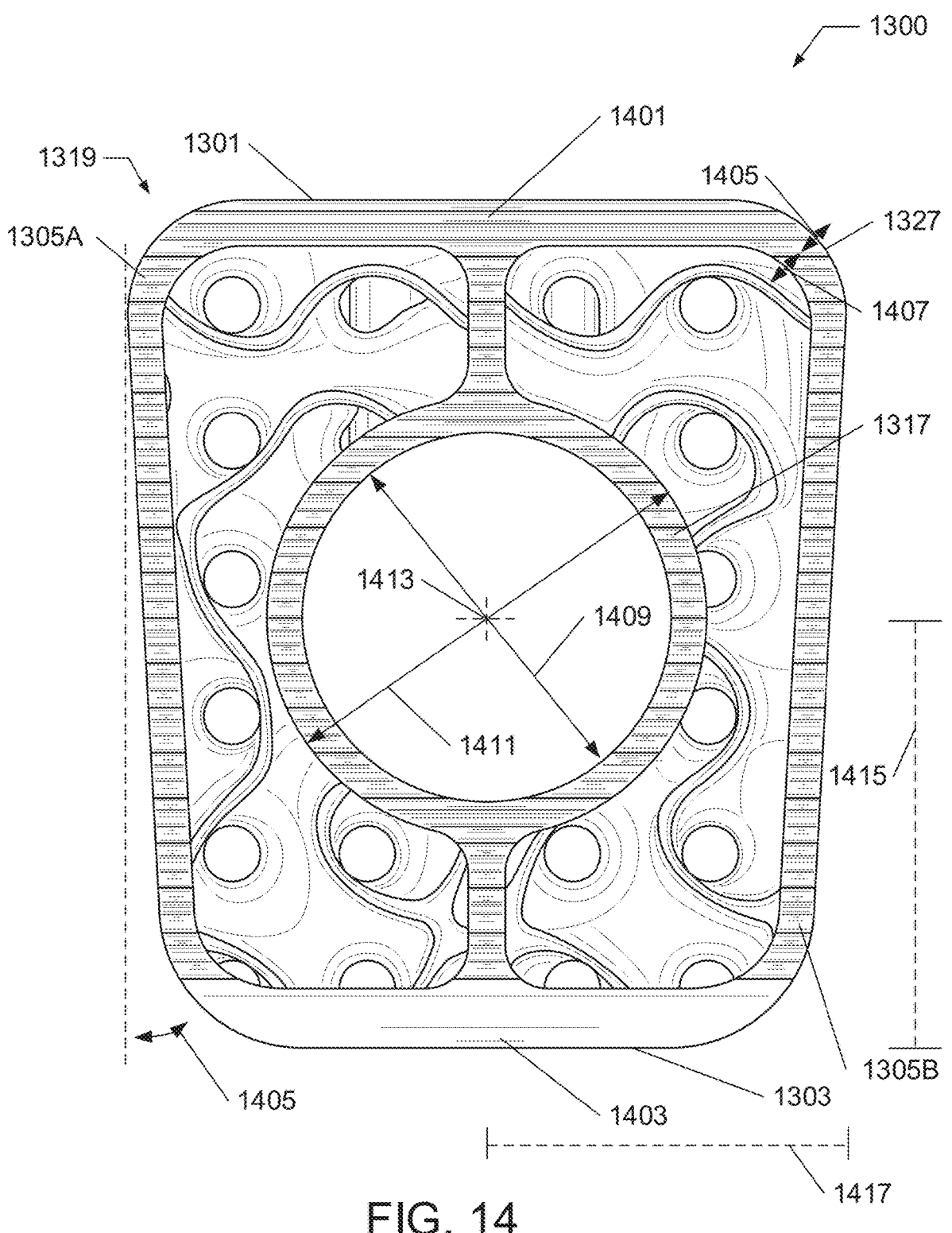
FIG. 14 illustrates a top view of a TPMS implant, according to one embodiment of the present disclosure.

FIG. 14 shows a top view of the implant 1300. In various embodiments, the implant 1300 includes a proximal end 1401 at the proximal surface 1301 and a distal end 1403 at the distal surface 1303. In one or more embodiments, the proximal end 1401 includes one or more profile shapes, such as, for example, the profiles 1201A-D shown in FIGS. 12A-D and described herein.

In at least one embodiment, the side surfaces 1305 taper towards each other in a direction from the proximal end 1401 to the distal end 1403. In one or more embodiments, the taper occurs at a taper angle 1405 of about 0.0-20.0 degrees, about 0.25-2.0 degrees, about 2.0-4.0 degrees, about 4.0-6.0 degrees, about 6.0-8.0 degrees, about 8.0-10.0 degrees, about 10.0-12.0 degrees, about 12.0-14.0 degrees, about 14.0-16.0 degrees, about 16.0-18.0 degrees, or about 18.0-20.0 degrees.

In various embodiments, one or more of the corners 1327 A-D of the implant 1300 include an outer radius 1405 of about 1.0-3.0 mm, or about 1.0 mm, or about 1.5-2.0 mm, or about 2.0-2.5 mm, or about 2.5 mm, or about 2.5-3.0 mm, or about 3.0-3.5 mm. According to one embodiment, one or more of the corners 1327 A-D include an inner radius 1407 of about 1.0-4.0 mm, or about 1.5-2.0 mm, or about 2.0-2.5 mm, or about 2.5 mm, or about 2.5-3.0 mm, or about 3.0-3.5 mm, or about 3.5-4.0 mm, or about 4.0-4.5 mm.

In one or more embodiments, the central region 1317 includes an inner diameter 1409 of about 5.0-9.0 mm, or about 4.5-5.0 mm, or about 5.0-5.5 mm, or about 5.5-6.0 mm, or about 6.5-7.0 mm, or about 7.0-7.5 mm, or about 7.25 mm, or about 7.5-8.0 mm, or about 7.75 mm, or about 8.0-8.5 mm, or about 8.1 mm, or about 8.5-9.0 mm. In various embodiments, the central region 1317 includes an outer diameter 1411 of about 6.5-12.5 mm, or about 6.5-7.0 mm, or about 7.0-7.5 mm, or about 7.25 mm, or about 7.5-8.0 mm, or about 8.0-8.5 mm, or about 8.5-9.0 mm, or about 8.85 mm, or about 9.0-9.5 mm, or about 9.5-10.0 mm, or about 9.75 mm, or about 10.0-10.5 mm, or about 11.0-11.5 mm, or about 12.0-12.5 mm.

In at least one embodiment, a center point 1413 of the central region 1317 is oriented at a height 1415 of about 6.0-9.0 mm, or about 5.5-6.0 mm, or about 6.0-6.5 mm, or about 6.5-7.0 mm, or about 7.0-7.5 mm, or about 7.5 mm, or about 7.5-8.0 mm, or about 8.0-8.5, or about 8.5 mm, or about 8.5-9.0 mm, or about 8.87 mm, or about 9.5-10.0 mm from the distal surface 1303. According to one embodiment, the center point 1413 is oriented at a distance 1417 of about 6.0-8.0 mm, or about 5.5-6.0 mm, or about 6.0-6.5 mm, or about 6.5-7.0 mm, or about 7.0 mm, or about 7.0-7.5 mm, or about 7.5-8.0 mm, or about 8.0-8.5 mm from each of the side surfaces 1305 (e.g., from an outer point thereon nearest to the corners 1327 at the proximal end 1401).

Figure 15:
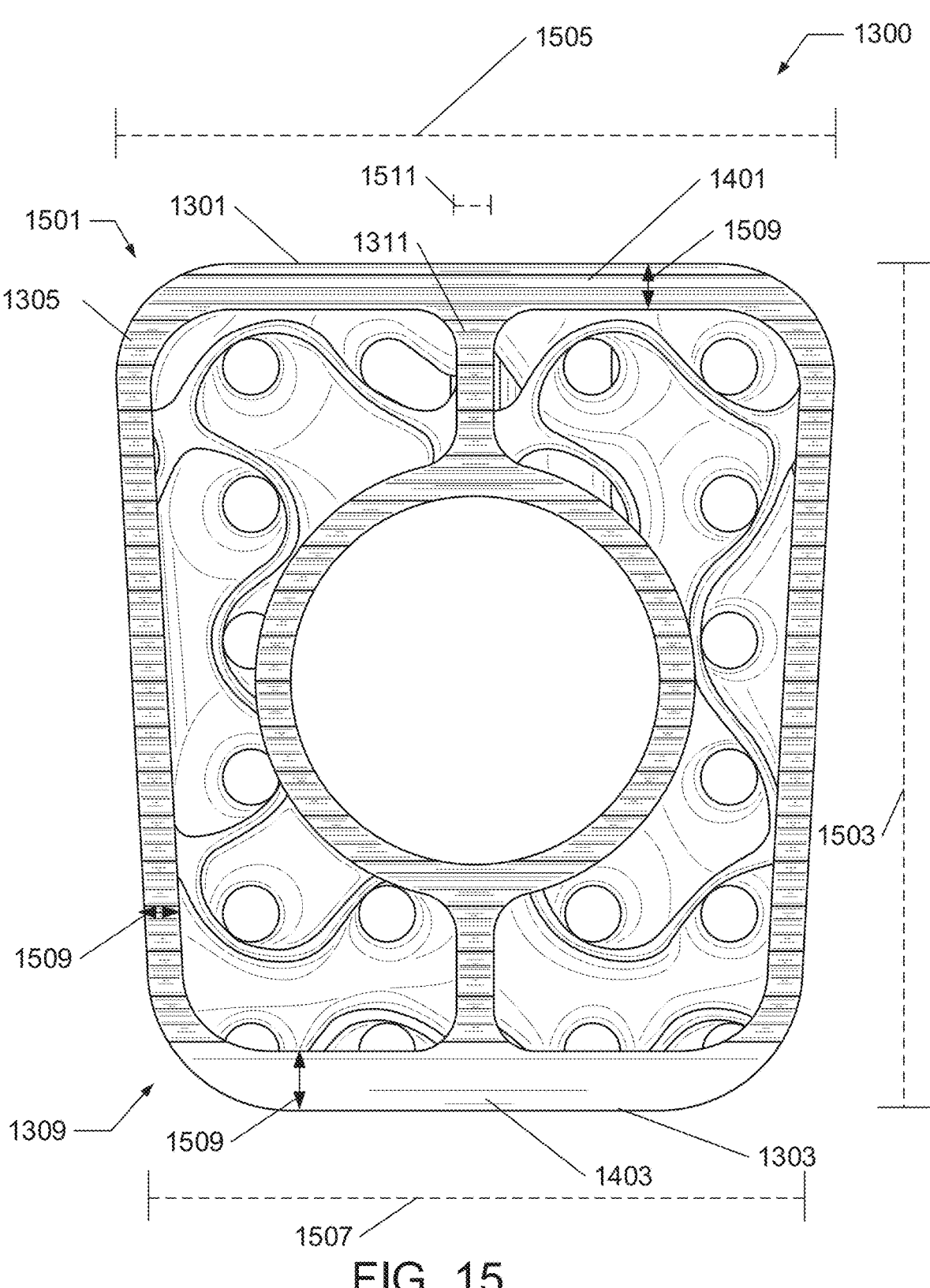
FIG. 15 illustrates a bottom view of a TPMS implant, according to one embodiment of the present disclosure.

FIG. 15 shows a bottom view of the implant 1300. In one or more embodiments, as described herein, the implant 1300 includes the bottom surface 1501. In various embodiments, the implant 1300 includes a total height 1503 of about 16.0-20.0 mm, or about 15.0-16.0 mm, or about 16.0-17.0 mm, or about 17.0-18.0 mm, or about 18.0-19.0 mm, or about 18.0 mm, or about 19.0-20.0 mm, or about 20.0-21.0 mm.

In one or more embodiments, at the proximal end 1401, the implant 1300 includes a proximal width 1505 of about 12.0-17.0 mm, or about 11.5-12.0 mm, or about 12.0-12.5 mm, or about 12.5-13.0 mm, or about 13.0-13.5 mm, or about 13.5-14.0 mm, or about 14.0-14.5 mm, or about 14.5-15.0 mm, or about 15.0-15.5 mm, or about 15.5-16.0 mm, or about 16.0 mm, or about 16.0-16.5 mm, or about 16.5-17.0 mm, or about 17.0-17.5 mm. According to one embodiment, at the distal end 1403, the implant 1300 includes a distal width 1507 of about 10.0-16.0 mm, or about 9.5.0-10.0 mm, or about 10.0-10.5 mm, or about 10.5-11.0 mm, or about 11.5-12.0 mm, or about 12.5-13.0 mm, or about 13.5-14.0 mm, or about 14.0 mm, or about 14.5-15.0 mm, or about 15.5-16.0 mm, or about 16.0-16.5 mm.

In at least one embodiment, the perimeter portion 1309 includes perimeter widths 1509 of about 0.5-2.0 mm, or about 0.5-1.0 mm, or about 1.0 mm, or about 1.0-1.5 mm, or about 1.5-2.0 mm, or about 2.0-2.5 mm. According to one embodiment, the proximal end 1401 includes a first perimeter width 1509, the distal end 1403 includes a second perimeter width 1509, and the side surfaces 1305 includes a third perimeter width 1509, each of the first, second, and third perimeter widths 1509 being a distinct, disparate magnitude. In one or more embodiments, the interior portion 1311 includes a width 1511 of about 0.25-1.5 mm, or about 0.25-0.5 mm, or about 0.5-0.75 mm, or about 0.75 mm, or about 0.75-1.0 mm, or about 1.0-1.25 mm, or about 1.25-1.5 mm, or about 1.5-1.75 mm.

Figure 16:
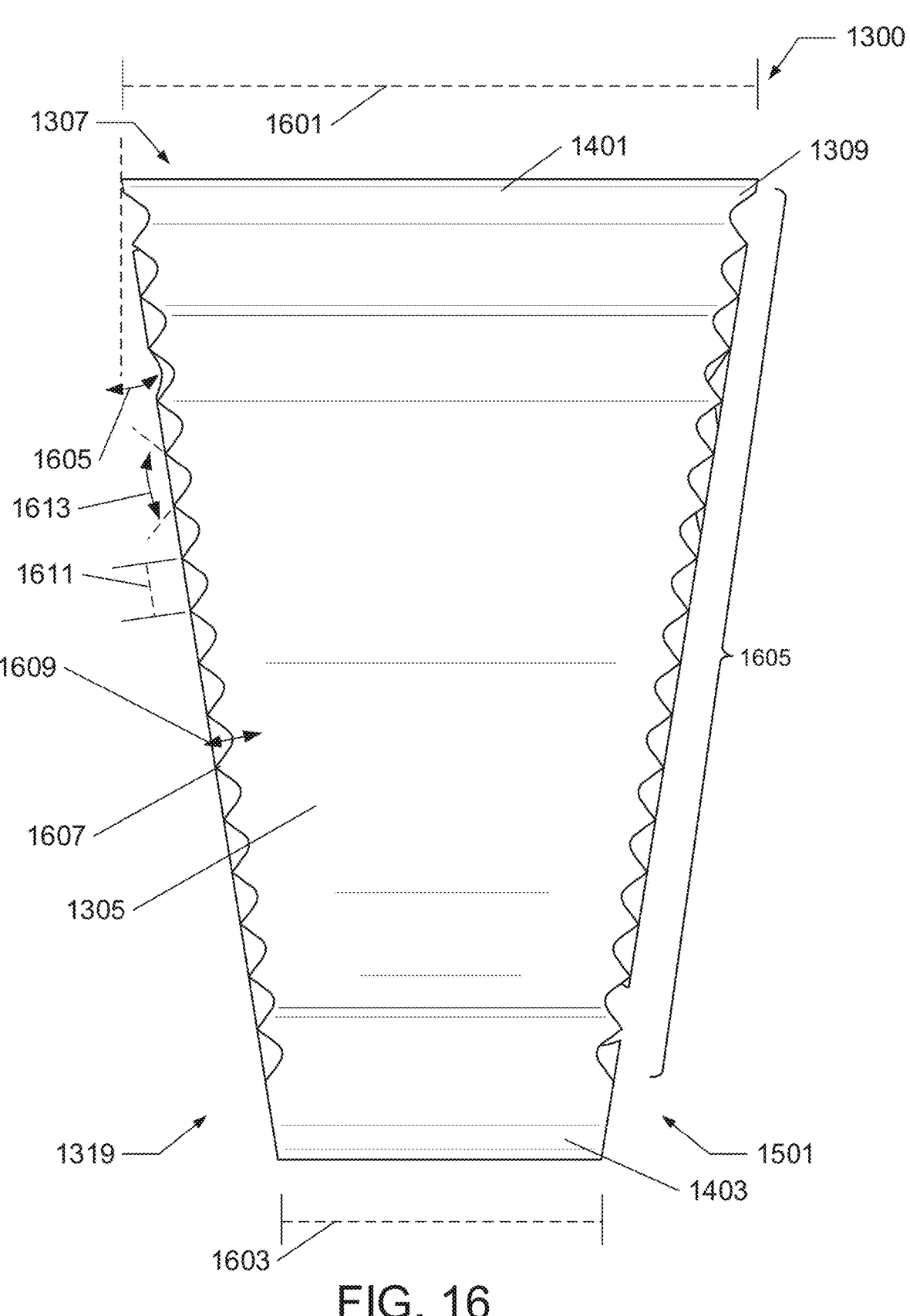
FIG. 16 illustrates a side view of a TPMS implant, according to one embodiment of the present disclosure.

With reference to FIG. 16, shown is a side view of the implant 1300. In various embodiments, the side surfaces 1305 includes a proximal depth 1601 at the proximal end 1401 and a distal depth 1603 at the distal end 1403. In one or more embodiments, the proximal depth 1601 is about 4.0-12.0 mm, or about 3.5-4.0 mm, or about 4.0-4.5 mm, or about 5.0-5.5 mm, or about 5.5-6.0 mm, or about 6.0-6.5 mm, or about 6.5-7.0 mm, or about 7.0-7.5 mm, or about 7.5-8.0 mm, or about 8.0-8.5 mm, or about 8.5-9.0 mm, or about 9.0-9.5 mm, or about 9.5-10.0 mm, or about 10.5-11.0 mm, or about 11.5-12.0 mm, or about 12.0 mm, or about 12.0-12.5 mm. In at least one embodiment, the distal depth 1603 is about 2.0-8.0 mm, or about 2.0-2.5 mm, or about 2.5-3.0 mm, or about 3.5-4.0 mm, or about 4.0-4.5 mm, or about 4.5-5.0 mm, or about 5.0-5.5 mm, or about 5.5-6.0 mm, or about 6.0-6.5 mm, or about 7.0-7.5 mm, or about 7.5-8.0 mm, or about 8.0-8.5 mm. In at least one embodiment, the implant 1300 tapers in depth between the proximal end 1401 and the distal end 1403. In one or more embodiments, the taper is at a taper angle 1605 of about 3.5-18.0 degrees.

In various embodiments, the implant 1300 includes one or more teeth sections 1605. In one or more embodiments, the one or more teeth sections 1605 extend outward from the top surface 1319 and/or bottom surface 1501 along the perimeter portion 1309. In at least one embodiment, the one or more teeth sections are integrally formed with the frame 1307. In one or more embodiments, each of the teeth sections 1605 includes a plurality of teeth 1607 in a number ranging from about 10-40. In various embodiments, the teeth 1607 include one or more of a sawtooth shape, an equilateral triangular shape, and other shapes. In one or more embodiments, the teeth 1607 are similar to the teeth 901A or teeth 901B (FIGS. 901A-B) described herein. According to some embodiments, the implant 1300 includes no teeth sections 1605, resulting, in at least one embodiment, in all external surfaces of the sides 1305 being substantially flat (e.g., all of the frame portions being substantially flat).

In various embodiments, each tooth 1607 includes a tooth radius 1609 that measures about 0.1-1.0 mm, about 0.1-0.25 mm, about 0.25 mm, about 0.25-0.5 mm, about 0.5-0.75 mm, or about 0.75-1.0 mm. In one or more embodiments, each tooth 1607 includes a tooth width 1611 that measures about 0.5-2.0 mm, about 0.5-1.0 mm, about 1.0 mm, about 1.0-1.5 mm, about 1.5 mm, about 1.5-2.0 mm, or about 2.5 mm. In at least one embodiment, each tooth 1607 includes a tooth angle 1613 that measures about 30.0-90.0 degrees, about 30.0-40.0 degrees, about 40.0-50.0 degrees, about 50.0-60.0 degrees, about 60.0-70.0 degrees, about 70.0-80.0 degrees, about 80.0-90.0 degrees, or about 90.0 degrees. According to one embodiment, the teeth section 1605 includes one or more proximal teeth 1615 that include a substantially flat surface. In at least one embodiment, the one or more proximal teeth 1615 include a width 1617 that measures about 0.1-1.0 mm, about 0.1-0.25 mm, about 0.25 mm, about 0.25-0.5 mm, about 0.5-0.75 mm, or about 0.75-1.0 mm.

Figure 17:
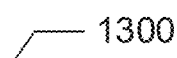
FIG. 17 illustrates a front view of a TPMS implant, according to one embodiment of the present disclosure.
Figure 17:
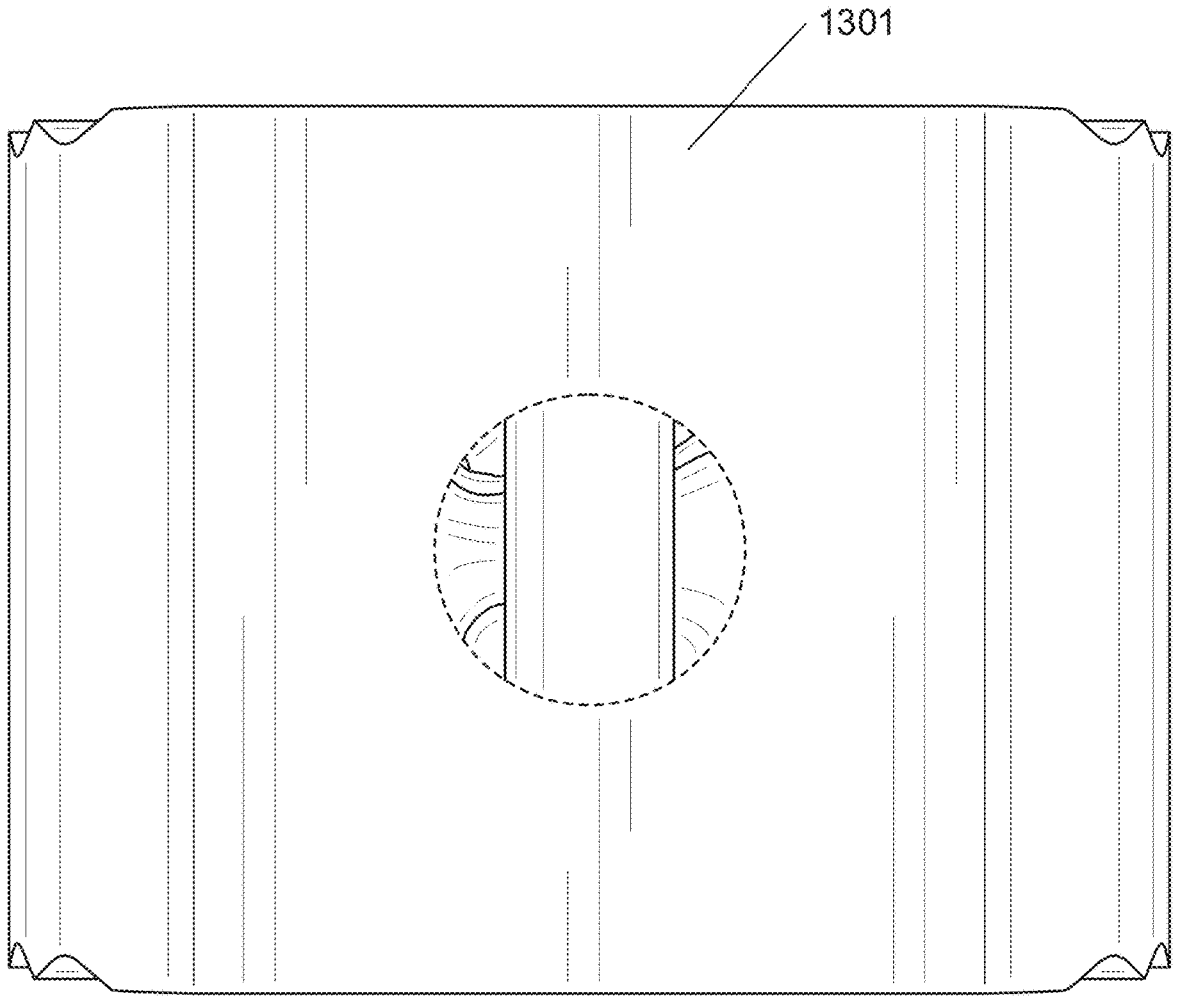

FIG. 17 shows a front view of the implant 1300. In at least one embodiment, the proximal surface 1301 includes one or more features (not illustrated) for receiving insertion instruments used to deploy the implant 1300 to a target site. According to one embodiment, the one or more features are similar to the void 1003A, keyhole 1003B, and/or divot 1003C shown in FIGS. 10A-C and described herein. In one or more embodiments, the proximal surface 1301 includes a substantially quadrilateral shape similar to, for example, a shape of the front portion 1001D (FIG. 1000D). In various embodiments, the proximal surface 1301 includes a substantially flat, convex, or concave shape or profile.

Figure 18:
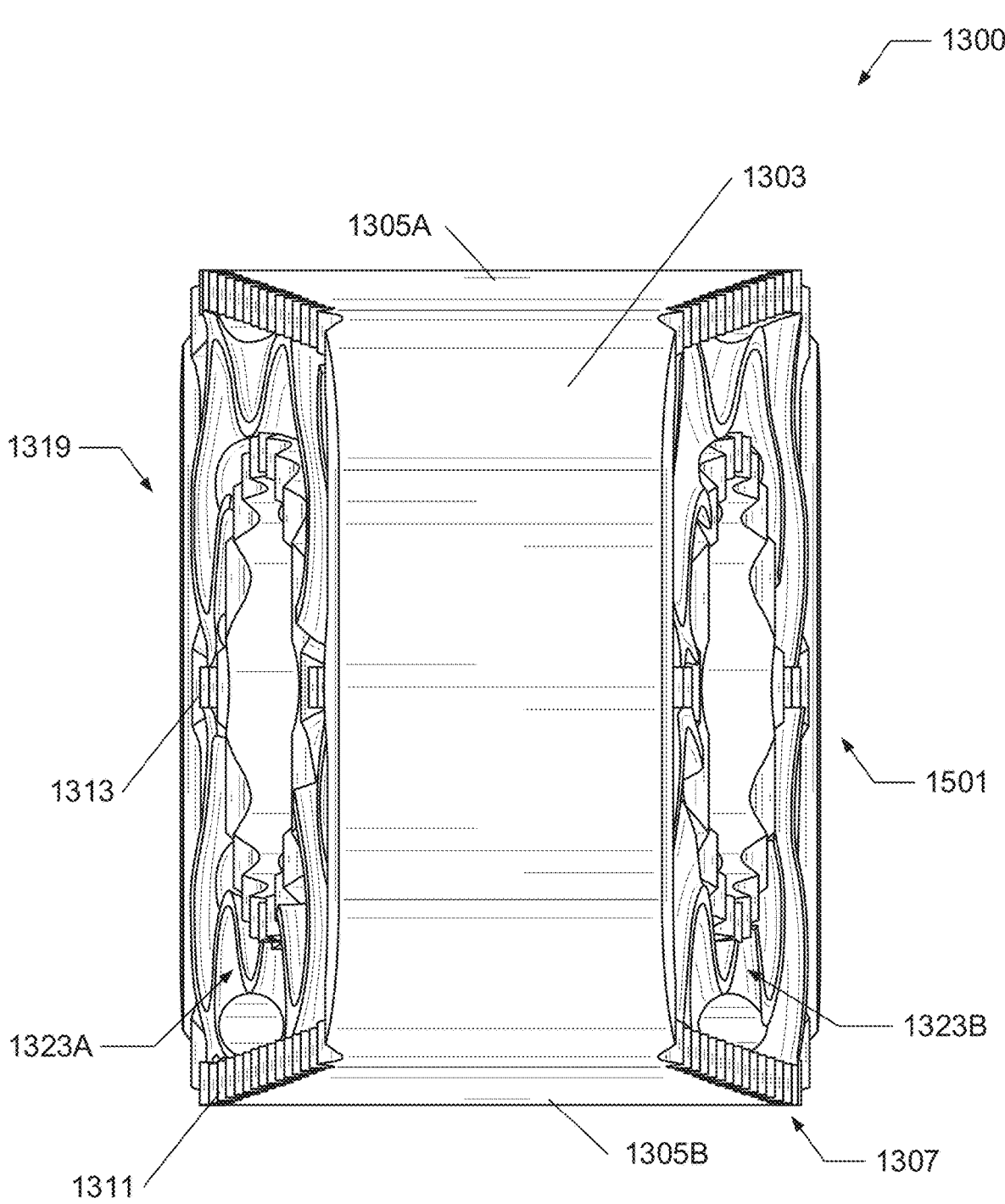
FIG. 18 illustrates a back view of a TPMS implant, according to one embodiment of the present disclosure.

FIG. 18 shows a back view of the implant 1300. In one or more embodiments, the distal surface 1303 of the implant 1300 includes one or more shapes, such as, for example, a substantially quadrilateral shape. In at least one embodiment, the distal surface 1303 includes a substantially flat, convex, or concave shape or profile. In one or more embodiments, the distal surface 1303 includes a taper, such as, for example, the taper 1105B (FIG. 11B) described herein.

Figure 19:
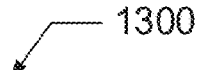
FIG. 19 illustrates a side view of a TPMS implant, according to one embodiment of the present disclosure.

FIG. 19 shows a side view of the implant 1300.

FIGS. 20-26 show various views of an exemplary implant 2000. According to one embodiment, the implant 2000 is substantially similar to one or more embodiments of the implant 1300 described herein and includes one or more shapes, elements, dimensions, and/or parameters thereof. In at least one embodiment, the implant 2000 is a spinal implant, such as, for example, a cervical cage implant.

Figure 20:
FIG. 20 illustrates a perspective view of a triply periodic, minimal surface (TPMS) implant, according to one embodiment of the present disclosure.
Figure 20:
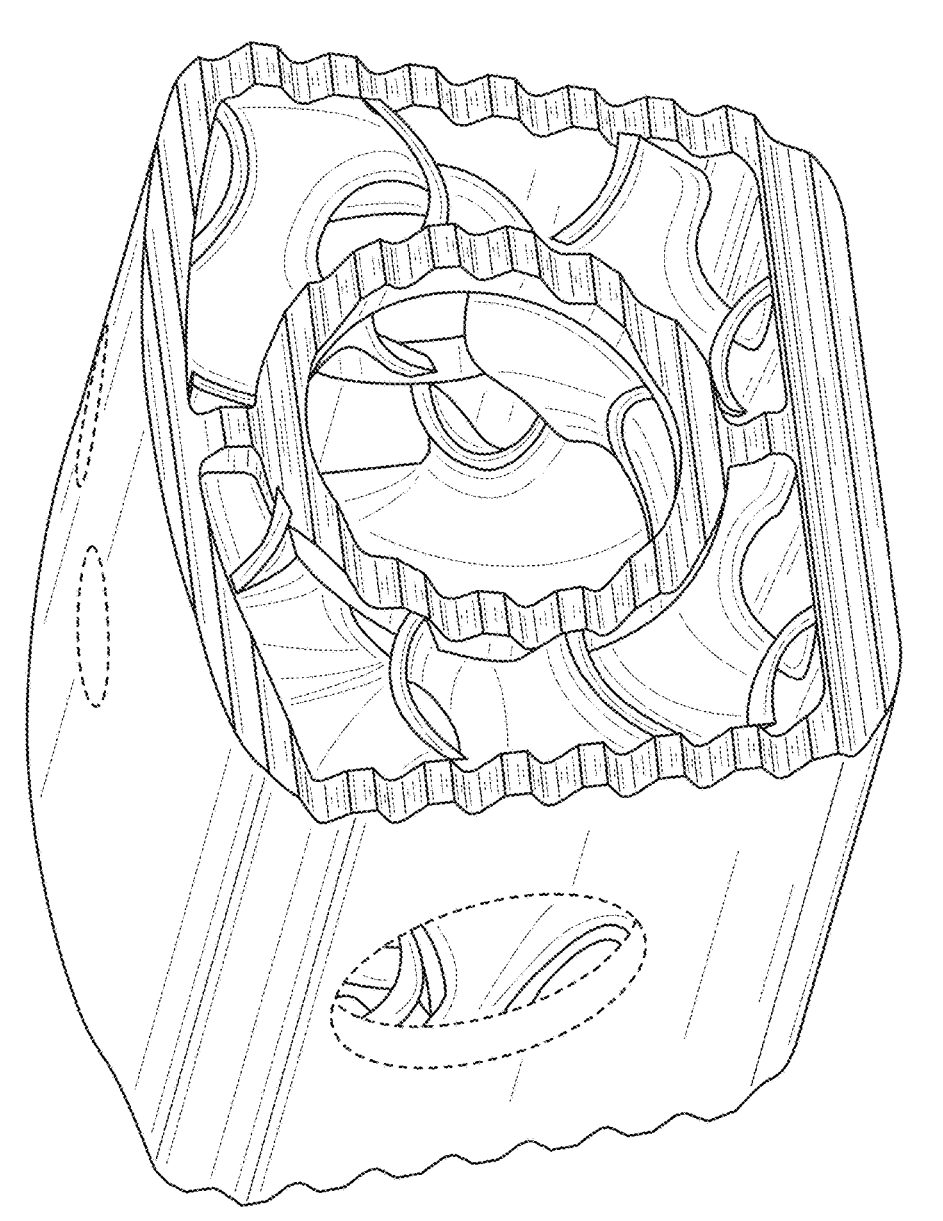

FIG. 20 shows a perspective view of the implant 2000.

Figure 21:
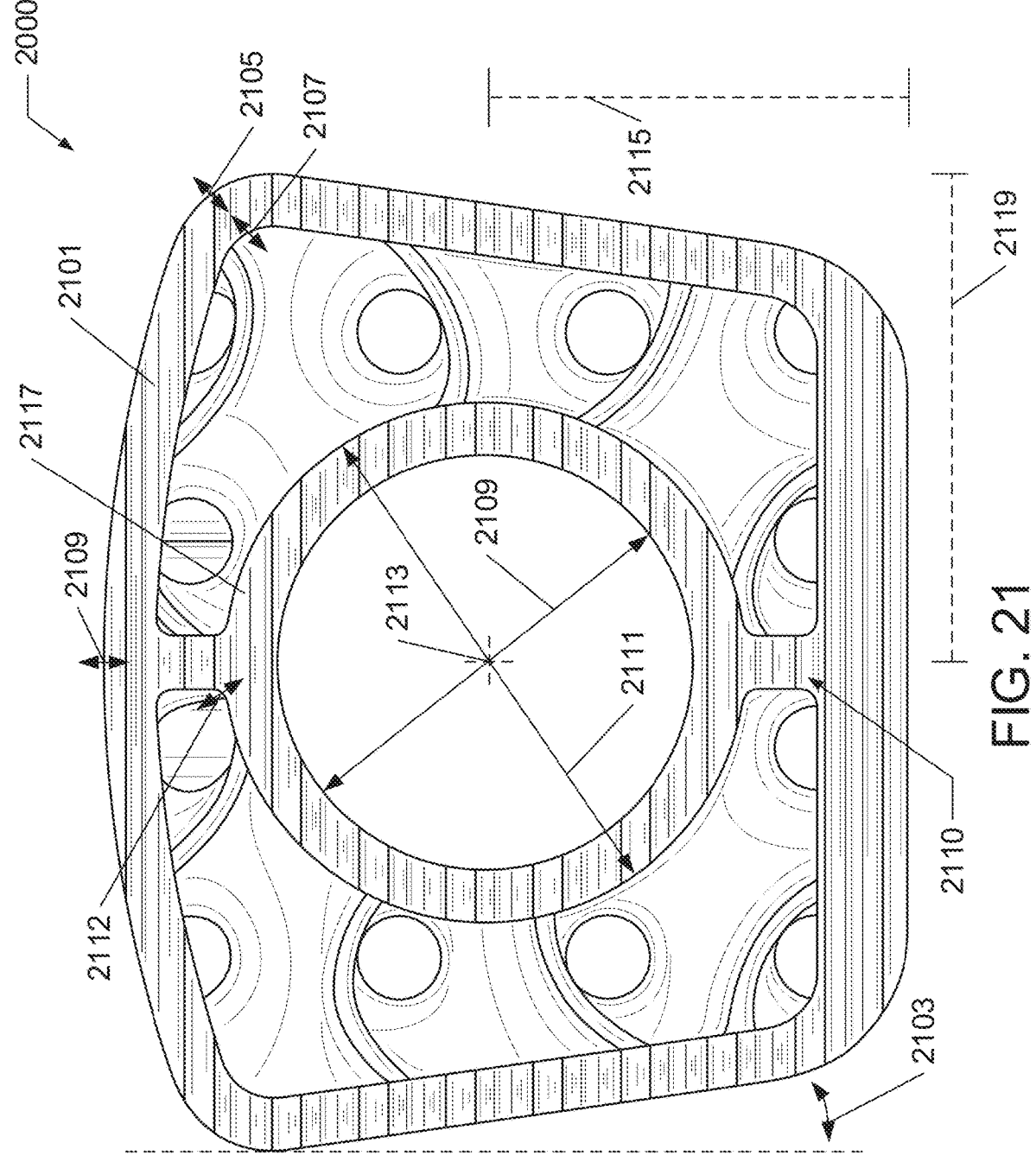
FIG. 21 illustrates a top view of a TPMS implant, according to one embodiment of the present disclosure.

FIG. 21 shows a top view of the implant 2000. In at least one embodiment, the implant 2000 includes an interior portion 2110 that is similar to the interior portion 1311 (FIG. 13) described herein. In various embodiments, the interior portion 1311 includes a central region 2117 (e.g., similar to the central region 1317 of FIG. 13) including a center point 2113 (similar to the center point 1413 of FIG. 14). In one or more embodiments, the central region 2117 includes an outer diameter 2111 that measures about 7.5 mm, or is sized similar to the outer diameter 1411. In various embodiments, the central region 2117 includes an inner diameter 2109 that measures about 6.0 mm, or is sized similar to the inner diameter 1409. In one or more embodiments, the central region 2117 includes a radius 2112 transitioning that transitions the central region 2117 to portions of the interior portion 2110 outside of the central region 2117. According to one embodiment, the radius 2112 measures about 0.1-1.0 mm, or about 0.1-0.2 mm, or about 0.25 mm, or about 0.2-0.3 mm, or about 0.3-0.4 mm, or about 0.4-0.5 mm, or about 0.5-0.6 mm, or about 0.6-0.7 mm, or about 0.7-0.8 mm, or about 0.8-0.9 mm, or about 0.9-1.0 mm, or about 1.0-1.1 mm.

According to one embodiment, the center point 2113 is oriented at a height 2115 sized similar to the height 1415 (FIG. 14). In one or more embodiments, the height 2115 measures about 6.5 mm. In various embodiments, the center point 2014 is oriented at a distance 2119 sized similar to the distance 1417 (FIG. 14). In at least one embodiment, the distance 2119 measures about 8.0 mm.

In in at least one embodiment, the implant 2000 includes a taper angle 2103 that is similar to the taper angle 1405 (FIG. 14). According to one embodiment, the taper angle 2103 is about 8.15 degrees, or is sized similar to the taper angle 1405.

In various embodiments, the implant 2000 includes corners 2127 that are similar to the corners 1327 (FIG. 13). In at least one embodiment, the corners 2127 include an outer radius 2105 that is sized similar to the outer radius 1405 (FIG. 14) or measures about 0.75 mm. In one or more embodiments, the corners 2127 include an inner radius 2107 that is sized similar to the inner radius 1407 (FIG. 14) or measures about 0.75 mm.

In at least one embodiment, the implant 2000 includes a proximal end 2101 that is similar to the proximal end 1401 (FIG. 14) described herein. In one or more embodiments, the proximal end 2101 is curved according to a predetermined radius of curvature 2109. In at least one embodiment, the radius of curvature 2109 is about 23.0-26.0 mm, or about 22.5-23.0 mm, or about 23.0-23.5 mm, or about 23.5-24.0 mm, or about 24.0-24.5 mm, or about 24.55 mm, or about 24.5-25.0 mm, or about 25.0-25.5 mm, or about 25.5-26.0 mm, or about 26.0-26.5 mm.

Figure 22:
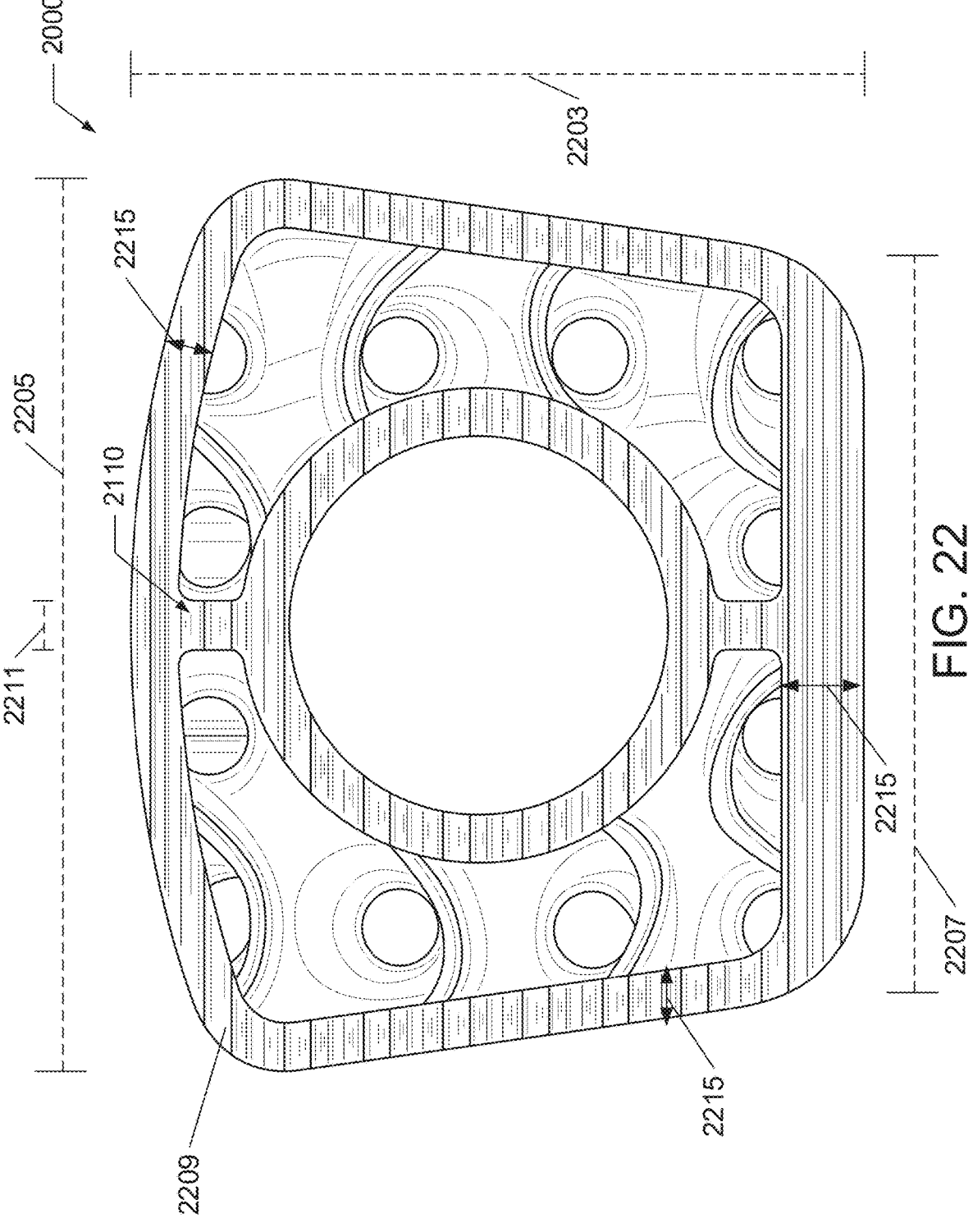
FIG. 22 illustrates a bottom view of a TPMS implant, according to one embodiment of the present disclosure.

FIG. 22 shows a bottom view of the implant 2000. In one or more embodiments, the implant 2000 includes a perimeter region 2209 (e.g., similar to the perimeter portion 1309 of FIG. 13). In at least one embodiment, the perimeter region 2209 includes one or more perimeters thicknesses 2215. According to one embodiment, the one or more perimeter thicknesses 2215 are sized similar to the one or more perimeter thicknesses 1509 (FIG. 15) described herein. In various embodiments, the one or more perimeter thicknesses 2215 measure about 0.75 mm. In one or more embodiments, the implant 2000 includes a height 2203 that is sized similar to the height 1503 (FIG. 15) described herein or measures about 13.0 mm.

In at least one embodiment, the implant 2000 includes a proximal width 2205 that is similar to the proximal width 1505 (FIG. 15) described herein. According to one embodiment, the proximal width 2205 is sized similar to the proximal width 1505 or measures about 16.0 mm. In one or more embodiments, the implant 2000 includes a distal width 2207 that is similar to the distal width 1507 (FIG. 15) described herein. In various embodiments, the distal width 2207 is sized similar to the proximal width 1507 or measures about 12.0 mm.

In one or more embodiments, the interior portion 2110 includes a width 2211. In at least one embodiment, the width 2211 is sized similar to the width 1511 (FIG. 15) described herein or measures about 0.75 mm.

Figure 23:
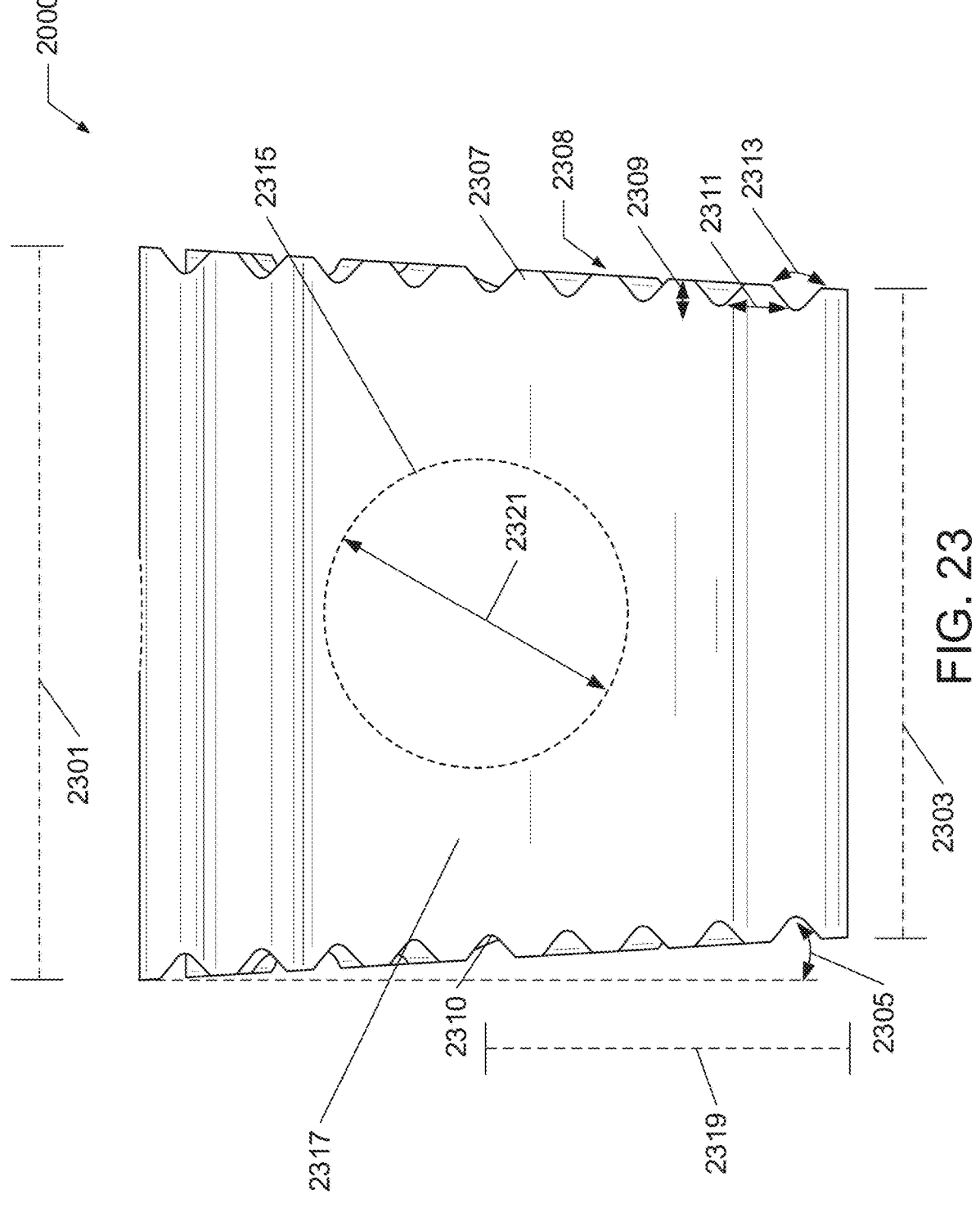
FIG. 23 illustrates a side view of a TPMS implant, according to one embodiment of the present disclosure.

FIG. 23 shows a side view of the implant 2000. In at least one embodiment, the implant 2000 includes a proximal depth 2301 that is sized similar to the proximal depth 1601 (FIG. 16) described herein or measures about 9.0 mm. In one or more embodiments, the implant 2000 includes a distal depth 2303 that is sized similar to the distal depth 1603 (FIG. 16) described herein or measures about 8.0 mm. According to one embodiment, the implant 2000 includes a taper angle 2305 that is sized similar to the taper angle 1605 (FIG. 16) described herein or measures about 3.5-18.0 degrees.

In one or more embodiments, the implant 2000 includes a plurality of teeth 2307 that are similar to the teeth 1607 (FIG. 16) described herein. In at least one embodiment, the tooth 2307 includes a substantially flat face 2308. In various embodiments, the tooth 2307 includes a tooth height 2309 measuring about 0.1-1.0 mm, or about 0.1-0.2 mm, or about 0.2-0.3 mm, or about 0.3-0.4 mm, or about 0.4-0.5 mm, or about 0.5-0.6 mm, or about 0.6-0.7 mm, or about 0.7-0.8 mm, or about 0.8-0.9 mm, or about 0.9-1.0 mm, or about 1.0-1.1 mm. According to one embodiment, a separation length 2311 separates each of the plurality of teeth 2307. In at least one embodiment, the separation length 2311 measures about 0.5-2.0 mm, or about 0.5-1.0 mm, or about 1.0-1.5 mm, or about 1.5 mm, or about 1.5-2.0 mm, or about 2.5 mm. In at least one embodiment, a trough region 2310 separates each of the plurality of teeth 2307. According to one embodiment the trough region 2310 includes a trough angle 2313 of about 70.0-80.0 degrees, or about 69.0-71.0 degrees, or about 71.0-73.0 degrees, or about 73.0-75.0 degrees, or about 75.0-77.0 degrees, or about 77.0-79.0 degrees, or about 79.72 degrees, or about 79.0-81.0 degrees.

In at least one embodiment, the implant 2000 includes one or more side holes 2315. In one or more embodiments, the side hole 2315 is centrally located on a side surface 2317 (e.g., that is similar to the side surface 1305, FIG. 13, described herein). According to one embodiment, the side hole 2315 is oriented at a height 2319 of about 6.5 mm and includes a diameter 2321 of about 5.0 mm.

Figure 24:
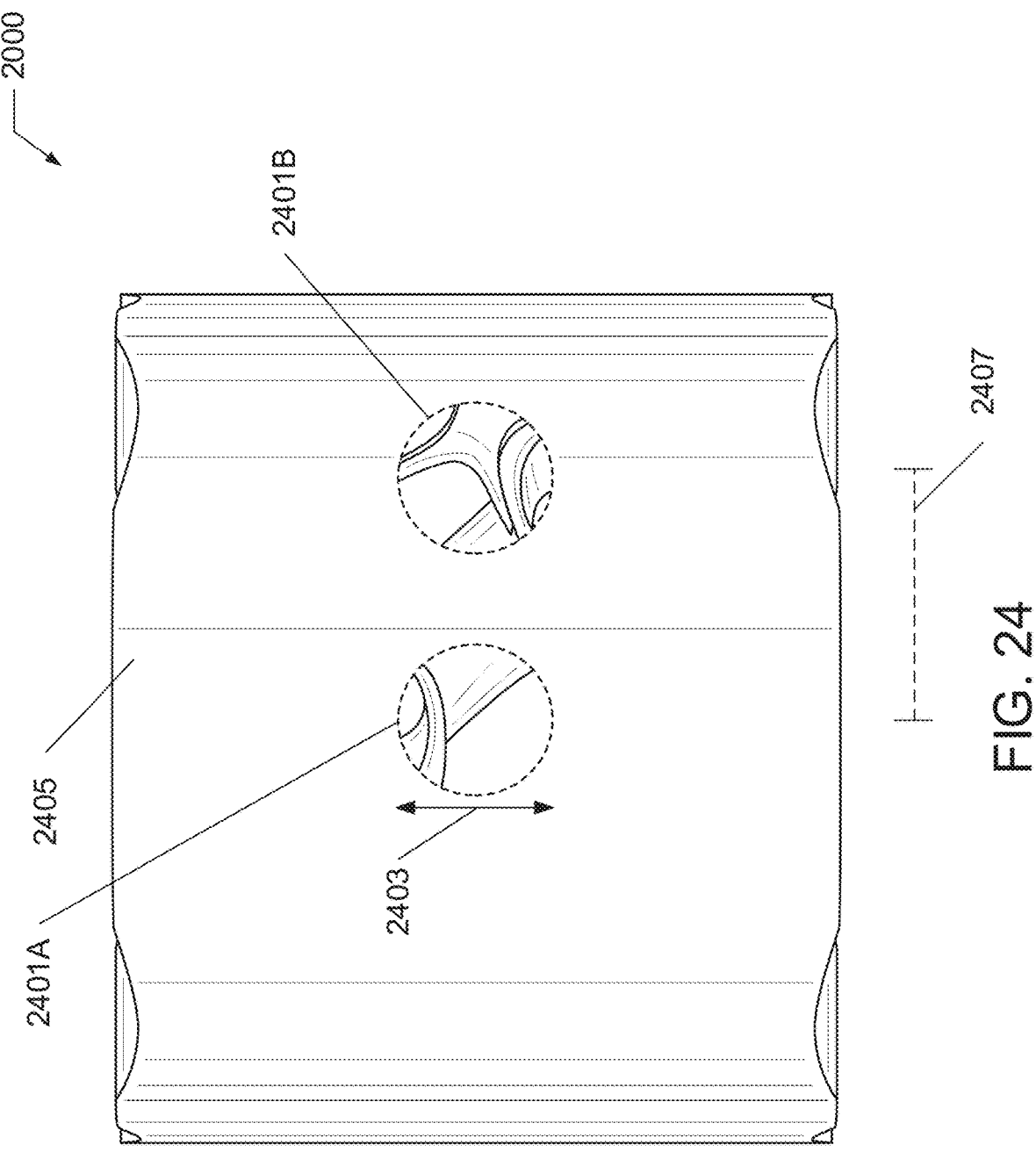
FIG. 24 illustrates a front view of a TPMS implant, according to one embodiment of the present disclosure.

FIG. 24 shows a front view of the implant 2000. According to one embodiment, the implant 2000 includes one or more top holes 2401. In at least one embodiment, the one or more top holes 2401 are configured to receive one or more instruments utilized during insertion of the implant 2000 into a target site. In various embodiments, the top hole 2401 includes a diameter 2303 measuring about 1.5-3.5 mm, or about 1.5-2.0 mm, or about 2.0-2.5 mm, or about 2.5 mm, or about 2.5-3.0 mm, or about 3.0-3.5 mm. In at least one embodiment, the diameter 2303 is selected such that the top hole 2401 receives a particular insertion instrument. According to one embodiment, a top hole 2401 of the one or more top holes 2401 are centrally located on a proximal surface 2405 (e.g., that is similar to the proximal surface 1301, FIG. 13, described herein). In one or more embodiments, a second top hole 2401 of the one or more top holes 2401 is oriented at a particular distance 2407 from a center point of the proximal surface 2405. In at least one embodiment, the particular distance 2407 is about 3.0-5.0 mm or about 4.0 mm.

Figure 25:
FIG. 25 illustrates a back view of a TPMS implant, according to one embodiment of the present disclosure.
Figure 25:
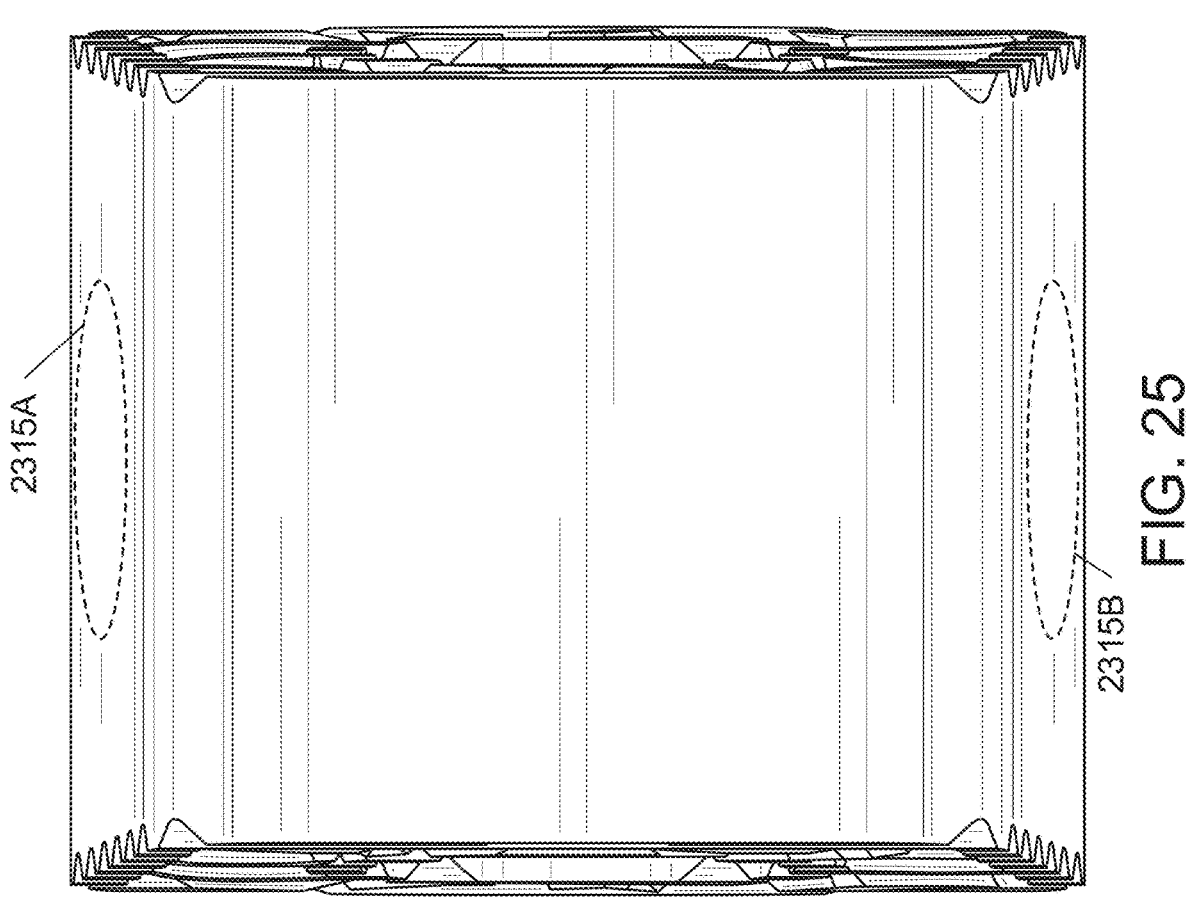

FIG. 25 shows a back view of the implant 2000.

Figure 26:
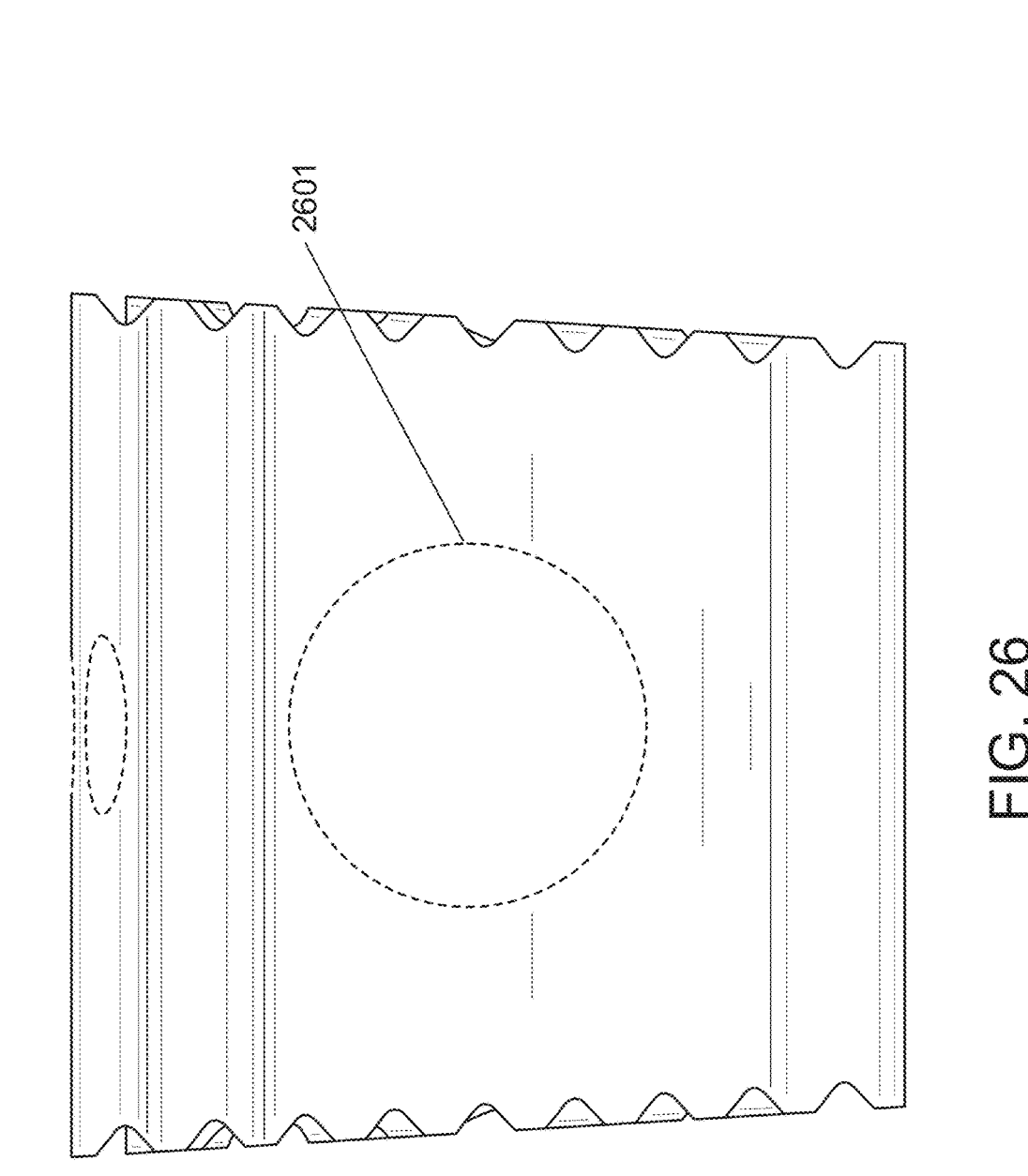
FIG. 26 illustrates a side view of a TPMS implant, according to one embodiment of the present disclosure.

FIG. 26 shows a side view of the implant 2000.

FIGS. 27-33 show various views of an exemplary implant 2700. According to one embodiment, the implant 2700 is substantially similar to one or more embodiments of the implant 1300 and implant 2000 described herein and includes one or more shapes, elements, dimensions, and/or parameters thereof each. In at least one embodiment, the implant 2000 is a foot implant, such as, for example, an osteotomy wedge implant.

Figure 27:
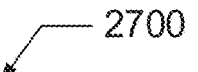
FIG. 27 illustrates a perspective view of a triply periodic, minimal surface (TPMS) implant, according to one embodiment of the present disclosure.

FIG. 27 shows a perspective view of the implant 2700.

Figure 28:
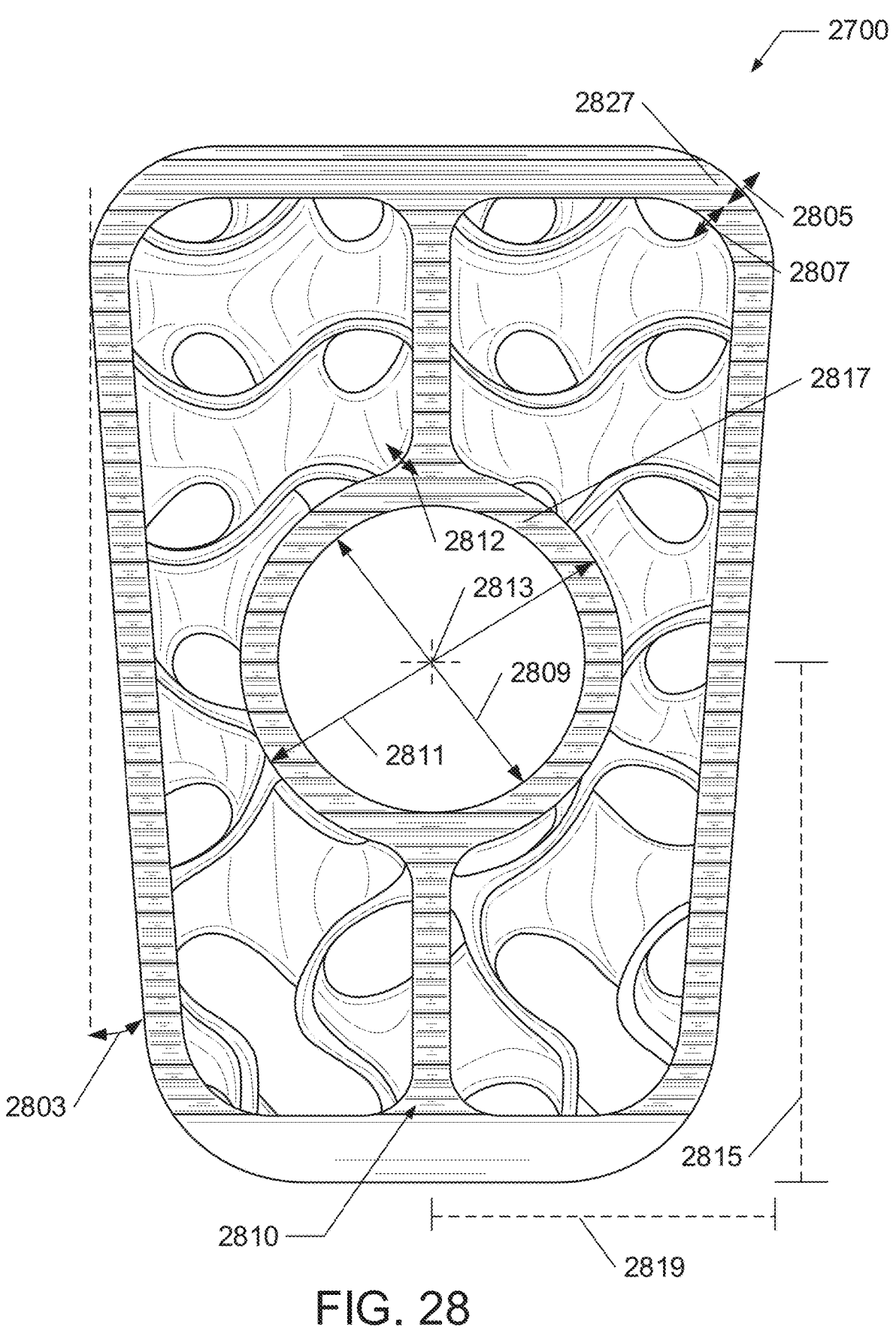
FIG. 28 illustrates a top view of a TPMS implant, according to one embodiment of the present disclosure.

FIG. 28 shows a top view of the implant 2700. In at least one embodiment, the implant 2700 includes an interior portion 2810 that is similar to the interior portion 1311 (FIG. 13) described herein. In various embodiments, the interior portion 1311 includes a central region 2817 (e.g., similar to the central region 1317 of FIG. 13) including a center point 2813 (e.g., similar to the center point 1413 of FIG. 14). In one or more embodiments, the central region 2817 includes an outer diameter 2811 that measures about 7.25 mm or is sized similar to the outer diameter 1411. In various embodiments, the central region 2817 includes an inner diameter 2809 that measures about 5.75 mm or is sized similar to the inner diameter 1409.

According to one embodiment, the center point 2113 is oriented at a height 2815 sized similar to the height 1415 (FIG. 14). In one or more embodiments, the height 2815 measures about 4.0-6.0 mm, about 4.0-4.5 mm, about 4.5-5.0 mm, about 5.0 mm, about 5.0-5.5 mm, or about 5.5-6.0 mm, or about 6.0-6.5 mm. In various embodiments, the center point 2813 is oriented at a distance 2819 sized similar to the distance 1417 (FIG. 14). In at least one embodiment, the distance 2819 measures about 6.0-9.0 mm, or about 6.0-6.5 mm, or about 6.5-7.0 mm, or about 7.0 mm, or about 7.0-7.5 mm, or about 7.5-8.0 mm, or about 8.0-8.5 mm, or about 8.5-9.0 mm.

In in at least one embodiment, the implant 2700 includes a taper angle 2803 that is similar to the taper angle 1405 (FIG. 14). According to one embodiment, the taper angle 2803 is about 0.0-10.0 degrees, about 0.5-2.0 degrees, about 2.0-4.0 degrees, about 4.0-6.0 degrees, about 6.0-8.0 degrees, about 8.0-10.0 degrees, or is sized similar to the taper angle 1405.

In various embodiments, the implant 2700 includes corners 2827 that are similar to the corners 1327 (FIG. 13). In at least one embodiment, the corners 2827 include an outer radius 2805 that is sized similar to the outer radius 1405 (FIG. 14) or measures about 2.5 mm. In one or more embodiments, the corners 2827 include an inner radius 2807 that is sized similar to the inner radius 1407 (FIG. 14) or measures about 4.0 mm.

In one or more embodiments, the central region 2817 includes a radius 2812 transitioning that transitions the central region 2817 to portions of the interior portion 2810 outside of the central region 2817. According to one embodiment, the radius 2812 measures about 0.1-1.0 mm, or about 0.1-0.2 mm, or about 0.2-0.3 mm, or about 0.3-0.4 mm, or about 0.35 mm, or about 0.4-0.5 mm, or about 0.5-0.6 mm, or about 0.6-0.7 mm, or about 0.7-0.8 mm, or about 0.8-0.9 mm, or about 0.9-1.0 mm, or about 1.0-1.1 mm, or is sized similar to the radius 2112 (FIG. 21).

Figure 29:
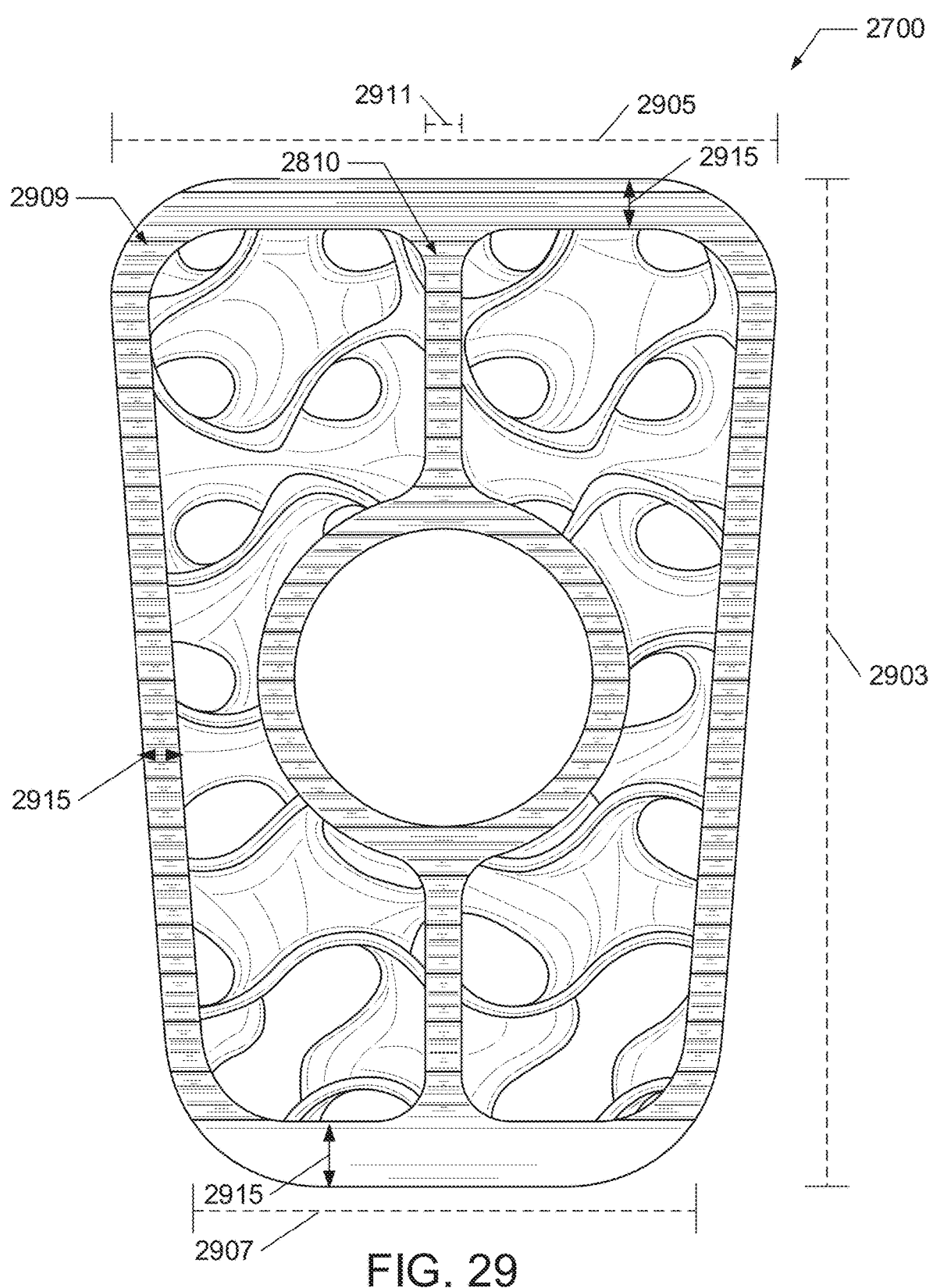
FIG. 29 illustrates a bottom view of a TPMS implant, according to one embodiment of the present disclosure.

FIG. 29 shows a bottom view of the implant 2700. In one or more embodiments, the implant 2700 includes a perimeter region 2909 (e.g., similar to the perimeter portion 1309 of FIG. 13). In at least one embodiment, the perimeter region 2909 includes one or more perimeters thicknesses 2915. According to one embodiment, the one or more perimeter thicknesses 2915 are sized similar to the one or more perimeter thicknesses 1509 (FIG. 15) described herein. In various embodiments, the one or more perimeter thicknesses measure about 1.0 mm. In one or more embodiments, the implant 2700 includes a height 2903 that is sized similar to the height 1503 (FIG. 15) described herein or measures about 16.0 mm.

In at least one embodiment, the implant 2700 includes a proximal width 2905 that is similar to the proximal width 1505 (FIG. 15) described herein. According to one embodiment, the proximal width 2905 is sized similar to the proximal width 1505 or measures about 14.0 mm. In one or more embodiments, the implant 2700 includes a distal width 2907 that is similar to the distal width 1507 (FIG. 15) described herein. In various embodiments, the distal width 2907 is sized similar to the proximal width 1507 or measures about 11.0 mm.

In one or more embodiments, the interior portion 2810 includes a width 2911. In at least one embodiment, the width 2911 is sized similar to the width 1511 (FIG. 15) described herein or measures about 0.75 mm.

Figure 30:
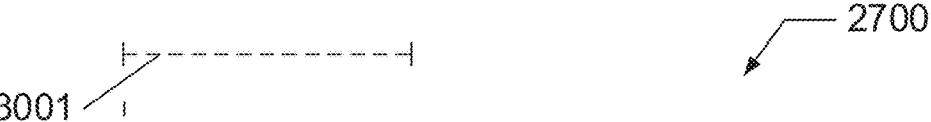
FIG. 30 illustrates a side view of a TPMS implant, according to one embodiment of the present disclosure.

FIG. 30 shows a side view of the implant 2700. In at least one embodiment, the implant 2700 includes a proximal depth 3001 that is sized similar to the proximal depth 1601 (FIG. 16) described herein or measures about 4.0 mm. In one or more embodiments, the implant 2700 includes a distal depth 3003 that is sized similar to the distal depth 1603 (FIG. 16) described herein or measures about 2.0 mm. According to one embodiment, the implant 2700 includes a taper angle 3005 that is sized similar to the taper angle 1605 (FIG. 16) described herein or measures about 3.0-18.0 degrees, or about 3.5 degrees, or about 7.0 degrees.

Figure 31:
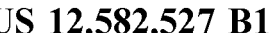
FIG. 31 illustrates a front view of a TPMS implant, according to one embodiment of the present disclosure.
Figure 31:
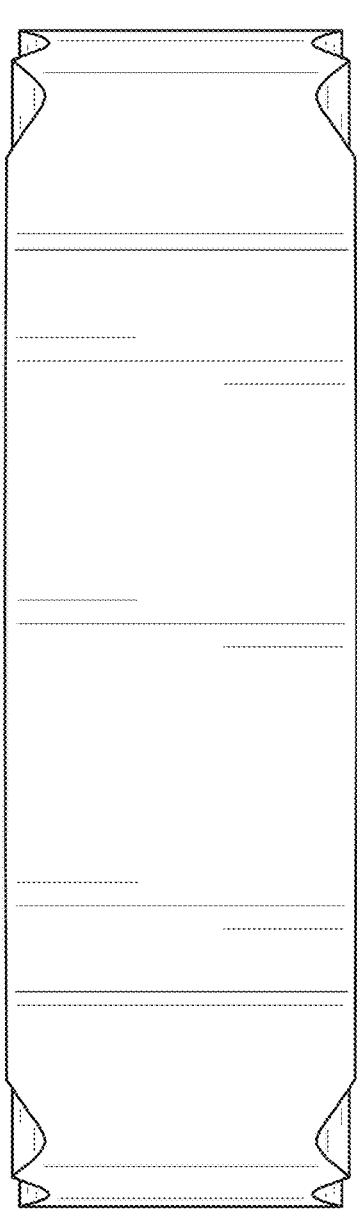
Figure 32:
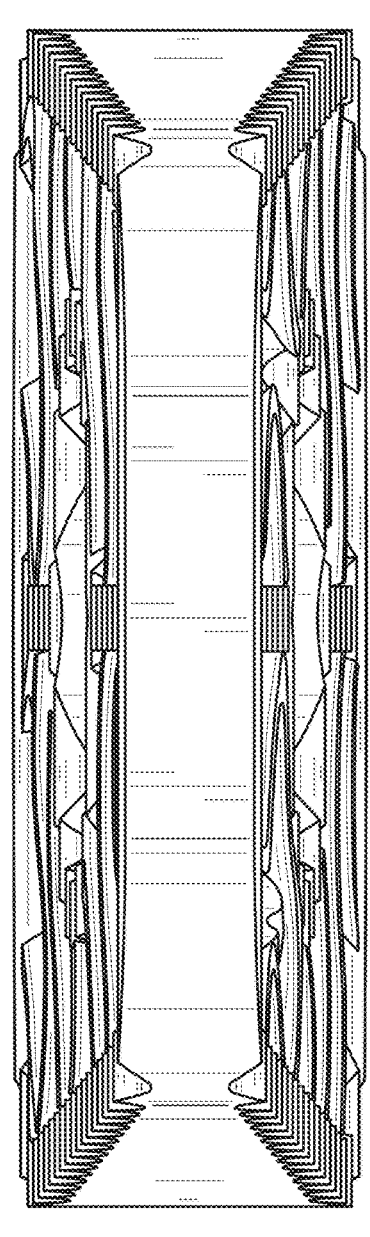
FIG. 32 illustrates a back view of a TPMS implant, according to one embodiment of the present disclosure.
Figure 33:
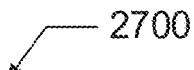
FIG. 33 illustrates a side view of a TPMS implant, according to one embodiment of the present disclosure.
Figure 33:
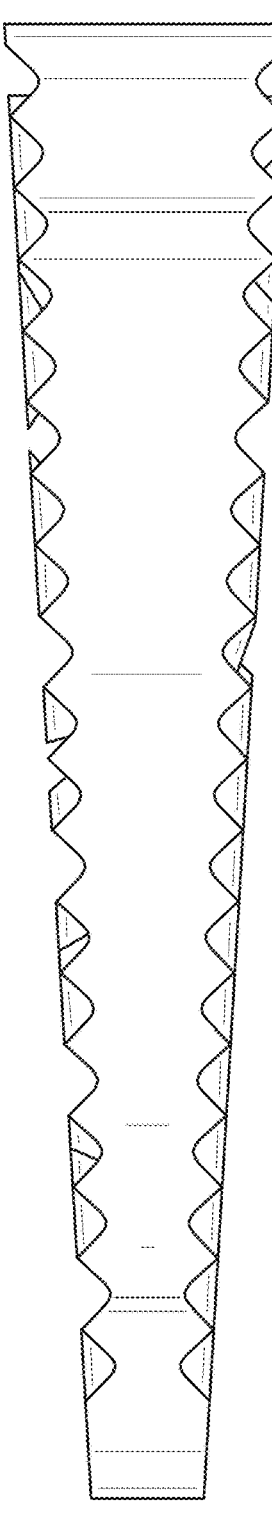

FIG. 31 shows a front view of the implant 2700.
FIG. 32 shows a back view of the implant 2700.
FIG. 33 shows a side view of the implant 2700.

CONCLUSION

While various aspects have been described in the context of a preferred embodiment, additional aspects, features, and methodologies of the claimed implants and methods will be readily discernible from the description herein, by those of ordinary skill in the art. Many embodiments and adaptations of the disclosure and claimed implants and methods other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed implants and methods. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed implants and methods. In addition, some steps may be carried out simultaneously, contemporaneously, or in synchronization with other steps.

The embodiments were chosen and described in order to explain the principles of the claimed implants and methods and their practical application so as to enable others skilled in the art to utilize the implants and methods and various embodiments and with various modifications as are suited to the particular use contemplated. Alternative embodiments will become apparent to those skilled in the art to which the claimed implants and methods pertain without departing from their spirit and scope. Accordingly, the scope of the claimed implants and methods is defined by the appended claims rather than the foregoing description and the exemplary embodiments described therein.

What is claimed is:

1. An additively manufactured implant comprising:
a volume between a top portion and a bottom portion, the volume comprising at least one porous sheet based triply periodic minimal surface (TPMS) portion comprising a wall density of at least 99%, wherein:
the volume is integrally formed with at least one non-porous structure; and
the at least one TPMS portion comprises an ultimate compression strength of about 50.0-230.0 MPa and a porosity of about 55-85%.

2. The additively manufactured implant of claim 1, wherein the at least one TPMS portion is free of nodes.

3. The additively manufactured implant of claim 2, wherein the at least one TPMS portion is free of struts.

4. The additively manufactured implant of claim 3, wherein the at least one TPMS portion is defined by a plurality of unit cells, each unit cell comprising a base geometry defined by a sinusoidal equation.

5. The 3D printed implant of claim 4, wherein the sinusoidal equation comprises:

$$\cos x \sin y + \cos y \sin z + \cos z \sin x = 0.$$

6. The additively manufactured implant of claim 5, wherein the plurality of unit cells and the at least one non-porous structure are integrally formed via powder bed fusion.

7. The additively manufactured implant of claim 6 comprising a spinal implant.

8. The additively manufactured implant of claim 6 comprising an osteotomy wedge.

9. The additively manufactured implant of claim 6 comprising a custom implant.

10. The additively manufactured implant of claim 6 comprising a custom, spherical implant for ankle reconstruction.

11. The additively manufactured implant of claim 6 comprising a prosthetic implant.

12. The additively manufactured implant of claim 6 comprising an implant associated with hemiarthroplasty.

13. The additively manufactured implant of claim 6 comprising a craniomaxillofacial implant.

14. The additively manufactured implant of claim 6 comprising a sports medicine implant.

15. The additively manufactured implant of claim 6 comprising a dental implant.

16. The additively manufactured implant of claim 6 comprising an arthrodesis-related implant.

17. The additively manufactured implant of claim 6, wherein the at least one TPMS portion comprises a wall thickness of at least 0.25 mm.

18. The additively manufactured implant of claim 6, wherein the at least one TPMS portion comprises a stiffness modulus of about 3.0-14.0 GPA.

19. The additively manufactured implant of claim 6, wherein the at least one TPMS portion comprises titanium.

20. The additively manufactured implant of claim 6, wherein the at least one TPMS portion comprises cobalt chromium.

21. An additively manufactured implant comprising:

a volume between a top portion and a bottom portion, the volume comprising at least one sheet based triply periodic minimal surface (TPMS) porous portion defined by a plurality of unit cells, wherein:

each unit cell comprises a base geometry defined by a sinusoidal equation;

the at least one TPMS porous portion comprises a wall density of at least 99%;

the volume is integrally formed with at least one non-porous structure; and the at least one TPMS porous portion comprises an ultimate compression strength of about 50.0-230.0 MPa and a porosity of about 55-85%.

22. The additively manufactured implant of claim 21, wherein the sinusoidal equation comprises:

$$\cos x \sin y + \cos y \sin z + \cos z \sin x = 0.$$

23. The additively manufactured implant of claim 22, wherein the implant is an implant of the group comprising: a spinal implant, an osteotomy wedge, a patient-specific implant, an implant for ankle reconstruction, a prosthetic implant, a hemiarthroplasty implant, a craniomaxillofacial implant, a dental implant, and an implant for arthrodesis.

\* \* \* \* \*